(12) United States Patent
Patchornik

(10) Patent No.: US 7,956,165 B2
(45) Date of Patent: Jun. 7, 2011

(54) COMPOSITIONS AND METHODS FOR PURIFYING AND CRYSTALLIZING MOLECULES OF INTEREST

(75) Inventor: Guy Patchornik, Kiryat-Ono (IL)

(73) Assignee: Affisink Biotechnology Ltd., Kiryat-Ono (IL)

( * ) Notice: Subject to any disclaimer, the term of this patent is extended or adjusted under 35 U.S.C. 154(b) by 724 days.

(21) Appl. No.: 11/826,906

(22) Filed: Jul. 19, 2007

(65) Prior Publication Data

US 2008/0108053 A1 May 8, 2008

Related U.S. Application Data

(63) Continuation-in-part of application No. PCT/IL2006/000173, filed on Feb. 9, 2006, and a continuation-in-part of application No. 11/330,112, filed on Jan. 12, 2006, which is a continuation-in-part of application No. PCT/IL2004/000669, filed on Jul. 22, 2004.

(30) Foreign Application Priority Data

Jul. 24, 2003 (IL) .......................................... 157086
Feb. 10, 2005 (IL) .......................................... 166800

(51) Int. Cl.
*A23J 1/00* (2006.01)
(52) U.S. Cl. ..................... 530/412; 530/418; 530/419
(58) Field of Classification Search ........................ None
See application file for complete search history.

(56) References Cited

U.S. PATENT DOCUMENTS

| | | | |
|---|---|---|---|
| 4,036,945 A | 7/1977 | Haber | |
| 4,331,647 A | 5/1982 | Goldenberg | |
| 4,946,778 A | 8/1990 | Ladner et al. | |
| 5,215,927 A | 6/1993 | Berenson et al. | |
| 5,831,012 A | 11/1998 | Nilsson et al. | |
| 5,968,753 A | 10/1999 | Tseng-Law et al. | |
| 6,017,719 A | 1/2000 | Tseng-Law et al. | |
| 6,534,628 B1 | 3/2003 | Nilsson et al. | |
| 6,740,734 B1 | 5/2004 | Nilsson et al. | |
| 7,198,930 B2 | 4/2007 | Kapeller-Libermann | |
| 2001/0008766 A1 | 7/2001 | Daunert et al. | |
| 2004/0265921 A1 | 12/2004 | Lesaicherre et al. | |
| 2006/0121519 A1 | 6/2006 | Patchornik | |

FOREIGN PATENT DOCUMENTS

| | | |
|---|---|---|
| WO | WO 87/04628 | 8/1987 |
| WO | WO 95/07466 | 3/1995 |
| WO | WO 00/39585 | 7/2000 |
| WO | WO 01/82975 | 11/2001 |
| WO | WO 02/085418 | 10/2002 |
| WO | WO 03/000708 | 1/2003 |
| WO | WO 2004/055213 | 7/2004 |
| WO | WO 2005/010141 | 2/2005 |
| WO | WO 2006/085321 | 8/2006 |
| WO | WO 2009/010976 | 1/2009 |

OTHER PUBLICATIONS

Barry et al. "Biotinylated Gene Therapy Vectors", Expert Opinion Biological Theory, 3(6): 925-940, 2003.
Basch et al. "Cell Separation Using Positive Immunoselective Techniques", Journal of Immunological Methods, 56(1): 269-280, 1983.
Chen et al. "Neoglycoproteins: Preparation and Properties of Complexes of Biotinylated Asparagine-Oligosaccharides With Avidin and Streptavidin", Biochemistry, 25(4): 939-944, 1986.
Fingl et al. "General Principles", The Pharmacological Basis of Therapeutics, 5th Ed., Sec.I(Chap.I): 1, 1975.
Hugues et al. "Affinity Purification of Functional Receptors for *Escherichia coli* Heat-Stable Enterotoxin From Rat Intestine", Biochemistry, 31(1): 12-16, 1992.
Lebkowski et al. "Rapid Isolation of Human CD34 Hematopoietic Stem Cells—Purging of Human Tumor Cells", Transplantation, 53(5): 1011-1019, 1992.
Parrott et al. "Metabolically Biotinylated Adenovirus for Cell Targeting, Ligand Screening, and Vector Purification", Molecular Therapy, 8(4): 688-700, 2003.
Ruby et al. "Affinity Chromatography With Biotinylated RNAs", Methods in Enzymology, 181: 97-121, 1990.
Sandgren et al. "An Immunoradiometric Assay for 1,25-Dihydroxyvitamin D3 Receptor", Analytical Biochemistry, 183(1): 57063, 1989.
Zhang et al. "Suitablility of Immobilized Metal Affinity Chromatography for Protein Purification From Canola", Biotechnology and Bioengineering, 68(1): 52-58, 2000.
Bird et al. "Single-Chain Antigen-Binding Proteins", Science, 242: 423-426, 1988.
Wilchek et al. "The Avidin-Biotin Complex: A Demonstration of the Utility of Biorecognition", IIGBT Science Newsletter, 2(2): 1-6, 1987.
Hardwick et al. "Design of Large-Scale Separation Systems for Positive and Negative Immunomagnetic Selection of Cells Using Superparamagnetic Microspheres", Journal of Hematotherapy, 1(4): 379-386, 1992. Abstract.
International Preliminary Report on Patentability Dated Jan. 28, 2010 From the International Bureau of WIPO Re.: Application No. PCT/IL2008/000988.
International Search Report and the Written Opinion Dated Jun. 25, 2008 From the International Searching Authority Re.: Application No. PCT/IL04/00669.
International Search Report Dated Jan. 27, 2009 From the International Searching Authority Re.: Application No. PCT/IL08/00988.
Response Dated Jan. 6, 2010 to Official Action of Jan. 8, 2009 From the US Patent and Trademark Office Re.: U.S. Appl. No. 11/330,112.
Mattiasson et al. "Affinity Precipitation of Proteins: Design Criteria for An Efficient Polymer", Journal of Molecular Recognition, 11: 211-216, 1998.
Poon et al. "Cell Cycle Regulation of the P34cdc/P33cdk2-Activating Kinase P40MO15", Journal of Cell Science, 107: 2789-2799, 1994.

(Continued)

*Primary Examiner* — Suzanne M Noakes
*Assistant Examiner* — Jae W Lee

(57) ABSTRACT

A composition-of-matter is provided. The composition comprising at least one antibody binding moiety capable of binding an antibody-labeled target molecule, cell or virus of interest, said at least one antibody binding moiety being attached to at least one coordinating moiety selected capable of directing the composition-of-matter to form a non-covalent complex when co-incubated with a coordinator ion or molecule.

8 Claims, 56 Drawing Sheets
(32 of 56 Drawing Sheet(s) Filed in Color)

OTHER PUBLICATIONS

Poon et al. "Reversible Immunoprecipitation Using Histidine- or Glutathione S-Transferase-Tagged Staphylococcal Protein A", Analytical Biochemistry, 218(1): 26-33, Apr. 1994.
Ramirez et al. "Purification of Caveolae by Affinity Two-Phase Partitioning Using Biotinylated Antibodies and NeutrAvidin-Dextran", Analytical Biochemistry, 331(1): 17-26, 2004.
Wikipedia "Protein L", Wikipedia, the Free Encyclopedia, http://en.wikipedia.org/wiki/Protein_L, 2 P., Apr. 24, 2008.
Communication Pursuant to Article 94(3) EPC Dated July 20, 2010 From the European Patent Office Re. Application No. 0745009.3.
Translation of Notice of Reason for Rejection Dated Jul. 9, 2010 From the Japanese Patent Office Re. Application No. 2006-520982.
Chen "Novel Affinity-Based Processes for Protein Purification", Journal of Fermentation and Bioengineering, 70(3): 199-209, 1990.
Lali et al. "Carboxymethyl Cellulose as A New Heterobifunctional Ligand Carrier for Affinity Precipitation of Proteins", Bioseparation, 7(4/5): 195-205, 1999.
International Search Report and the Written Opinion Dated Jan. 18, 2007 From the International Searching Authority Re.: Application No. PCT/IL2006/000173.
Communication Pursuant to Article 94(3) EPC Dated Dec. 13, 2007 From the European Patent Office Re.: Application No. 06711155.9.
Examination Report Dated Sep. 24, 2007 From the Government of India, Patent Office Re.: Application No. 621/CHENP/2006.
Search Report and Written Opinion Dated Dec. 1, 2006 From the Intellectual Property Office of Singapore Issued by the Australian Patent Office Re.: Application No. 200600484-0.
Basch et al. "Cell Separation Using Positive Immunoselective Techniques", Journal of Immunological Methods, 56(1): 269-280, 1983. Abstract Only.

Bradford "A Rapid and Sensitive Method for the Quantitation of Microgram Quantities of Protein Utilizing the Principle of Protein-Dye Binding", Analytical Biochemistry, 72: 248-254, 1976.
Orr "The Use of the 2-Iminobiotin-Avidin Interaction for the Selective Retrieval of Labeled Plasma Membrane Components", The Journal of Biological Chemistry, 256(2): 761-766, 1981.
Patchornik et al. "Free Nonimmobilized Ligands as A Tool for Purification of Proteins", Bioconjugate Chemistry, 16(5): 1310-1315, 2005. p. 1314, col. 2, Paragraph 3, Fig.4.
Zhong et al. "Human Blood Dendritic Cell-Like B Cells Isolated by the 5G9 Monoclonal Antibody Reactive With A Novel 220-KDa Antigen", Journal of Immunology, 163(3): 1354-1362, 1999.
Communication Relating to the Results of the Partial International Search Dated Jun. 26, 2006 From the International Searching Authority Re.: Application No. PCT/IL2006/000173.
International Preliminary Report on Patentability Dated Aug. 23, 2007 From the International Bureau of WIPO Re.: Application No. PCT/IL2006/000173.
Invitation to Pay Additional Fees Dated Mar. 26, 2008 From the International Searching Authority Re.: Application No. PCT/IL04/00669.
Official Action Dated Jan. 8, 2009 From the US Patent and Trademark Office Re.: U.S. Appl. No. 11/330,112.
Official Action Dated Jun. 10, 2008 From the US Patent and Trademark Office Re.: U.S. Appl. No. 11/330,112.
Official Action Dated Apr. 20, 2007 From the US Patent and Trademark Office Re.: U.S. Appl. No. 11/330,112.
Written Opinion Dated Jan. 27, 2009 From the International Searching Authority Re.: Application No. PCT/IL08/00988.

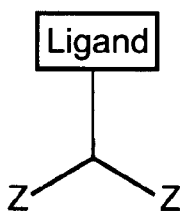
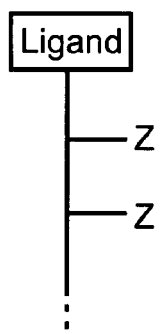
Fig. 1a          Fig. 1b          Fig. 1c
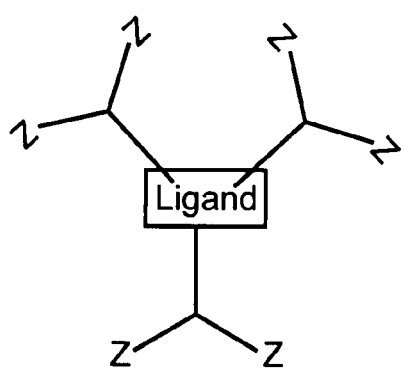
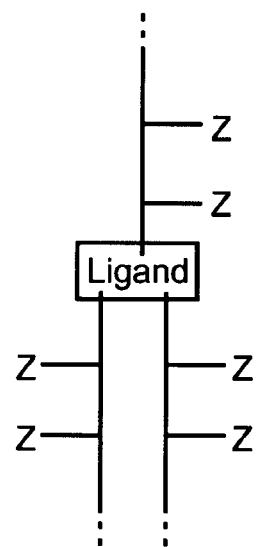
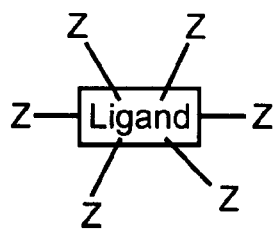
Fig. 1d          Fig. 1e          Fig. 1f
Z = chelator and/nucleotide sequence and/biotin, (and its derivatives) and/an electron rich or poor entity, etc...

addition of a competing free chelator

Ultrafiltration will remove free chelator and complexed metal

G = Guanine  C = Cytosine

"Avidin" = avidin, nitroavidin, iodoavidin, or any other avidin derivative.
Biotin = Biotin, DSB-X Biotin, or any other biotin derivative.

Z = chelator, biotin, nucleotide sequence, rich/poor entity etc.

coordinator = metal, avidin, complementary nucleotide sequence, electron rich/poor entity etc...

The same could apply for: Ligand — OH  Ligand — SH  Ligand — COOH

Formation of di-ligand in the presence of $Cu^{2+}$ ions:

Formation of tri-ligand in the presence of $Ru^{3+}$ ions:

The same could apply for: Ligand --- OH   Ligand --- SH   Ligand --- COOH

A synthetic peptide with four Trp residues

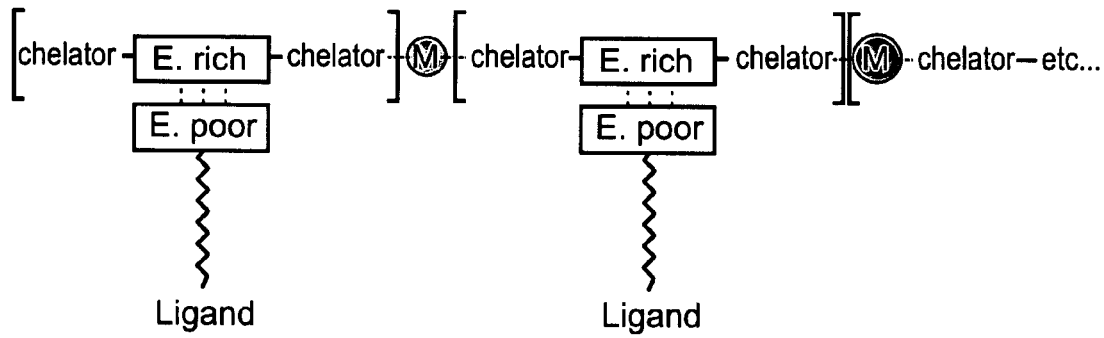
Fig. 23a
Fig. 23b
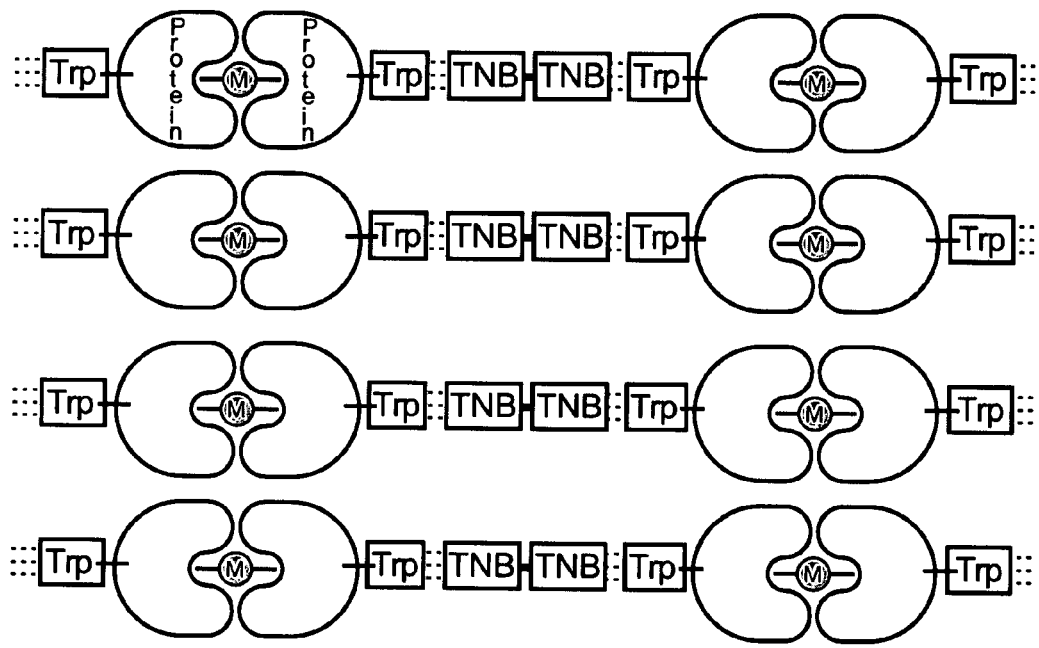
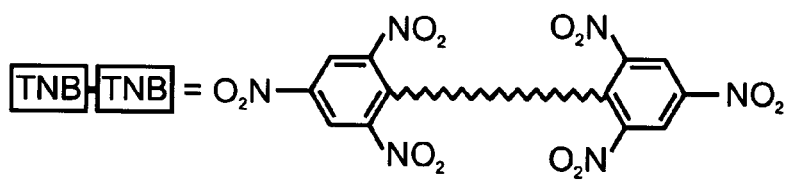
Fig. 24

Examples of chelators:
 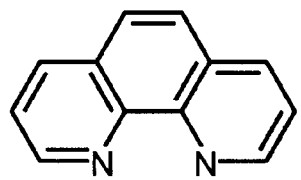 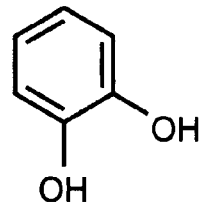
8-Hydroxyquinoline     1, 10 Phenanthroline     Catechol
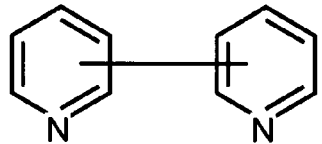 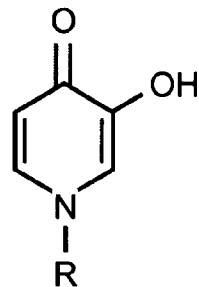 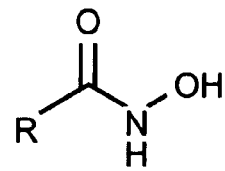
bipyridines     Pyridine-4-ones     Hydroxamaate
Examples of metals:
any $M^{2+}$, $M^{3+}$, or $M^{4+}$
such as: $Cu^{2+}$, $Fe^{3+}$, $Ru^{3+}$, $Al^{3+}$, $Co^{2+}$, $Cr^{3+}$, etc...
Fig. 25

Examples for electron poor molecules:
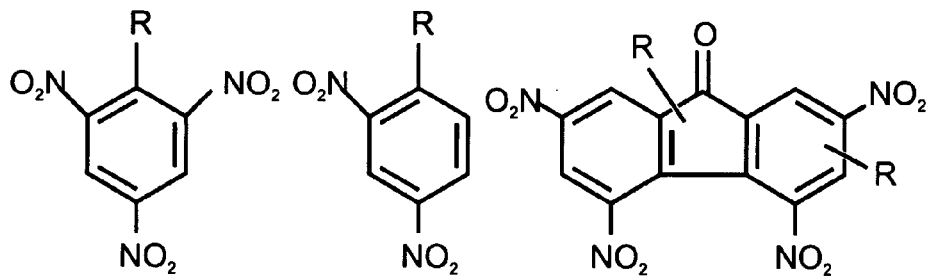
R=NHR, NR$_2$, OR, SR, NHCOR, etc...
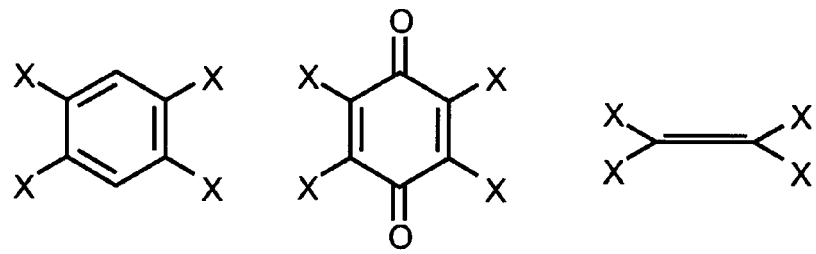
X=Cl, Br, I, F, CN, or any withdrawing group
Examples for electron rich molecules:
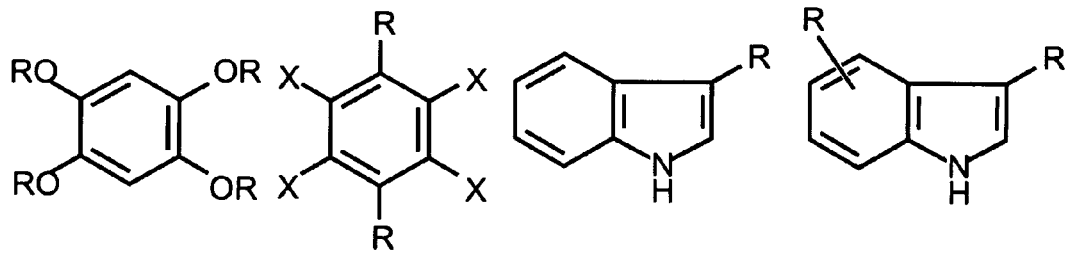
X=Cl, Br, I, F, CN, or any withdrawing group
R=NHR, NR$_2$, OR, SR, NHCOR, etc...
Fig. 26

NRK - Lysate

C2 - Lysate

E. Coli - Lysate

BSA

E. Coli - Lysate

E. Coli - Lysate

E. Coli - Lysate

Specific binding (pH 7)

Precipitation (pH 7)

Elution (pH 3)

Regeneration (pH 7)

Affinity Chromatography (AC)

Affinity Precipitation (AP)

Affinity Sinking (AS)

DB = Desthiothiobiotin   L = Ligand   NHS = N-Hydroxysuccinimidyl ester

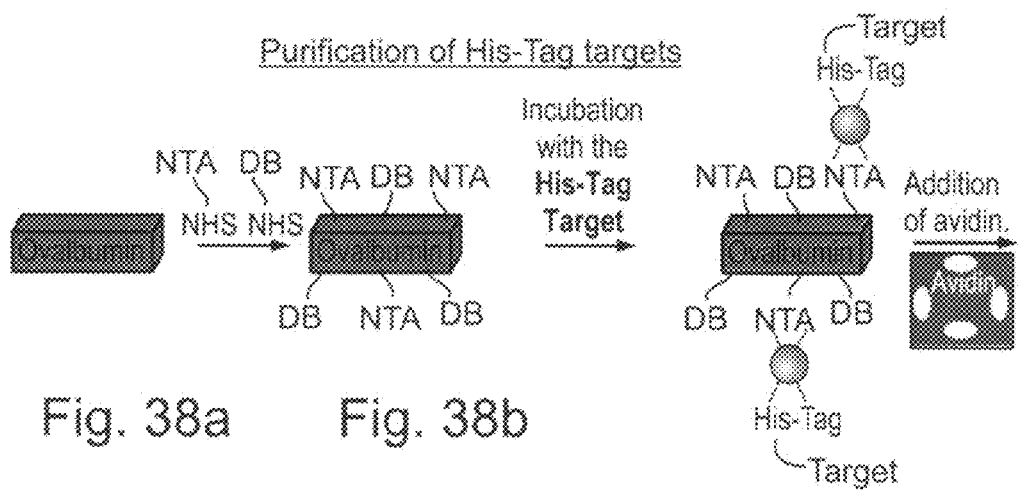
Fig. 38a  Fig. 38b  Fig. 38c
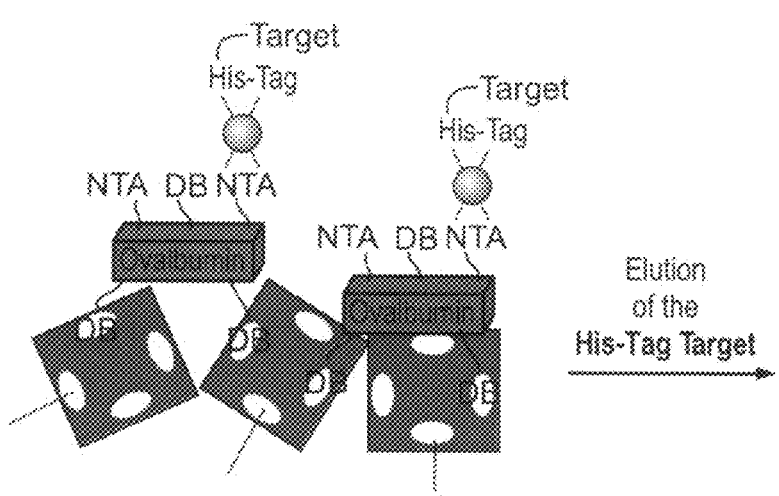
DB = Desthiothiobiotin  NTA = Nitrilotriacetic acid
NHS = N-Hydroxysuccinimidyl ester  ◯ = Metal   Fig. 38d
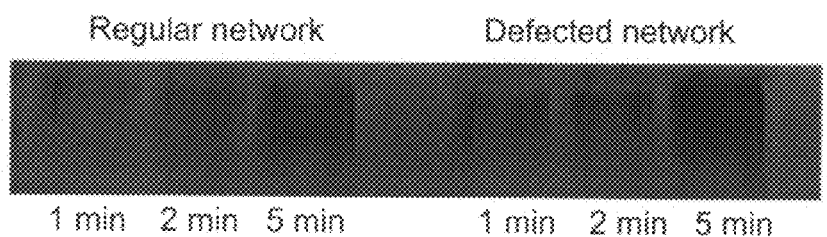
Fig. 39

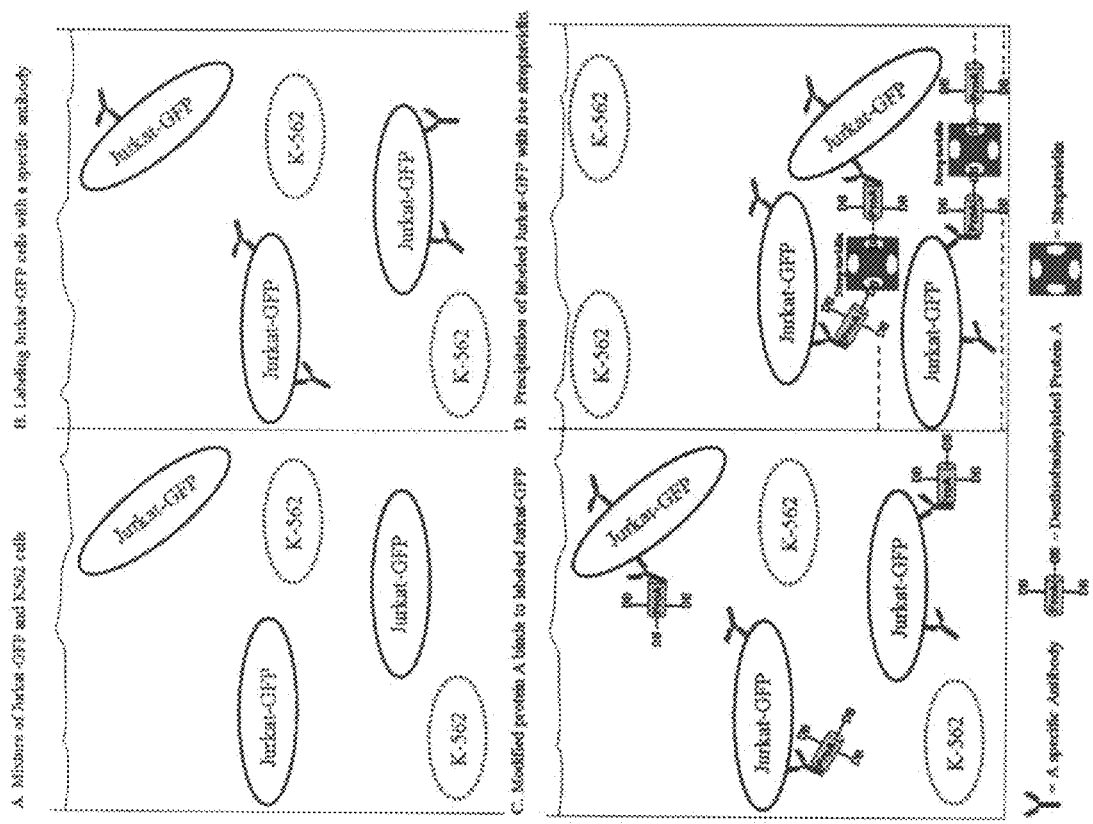

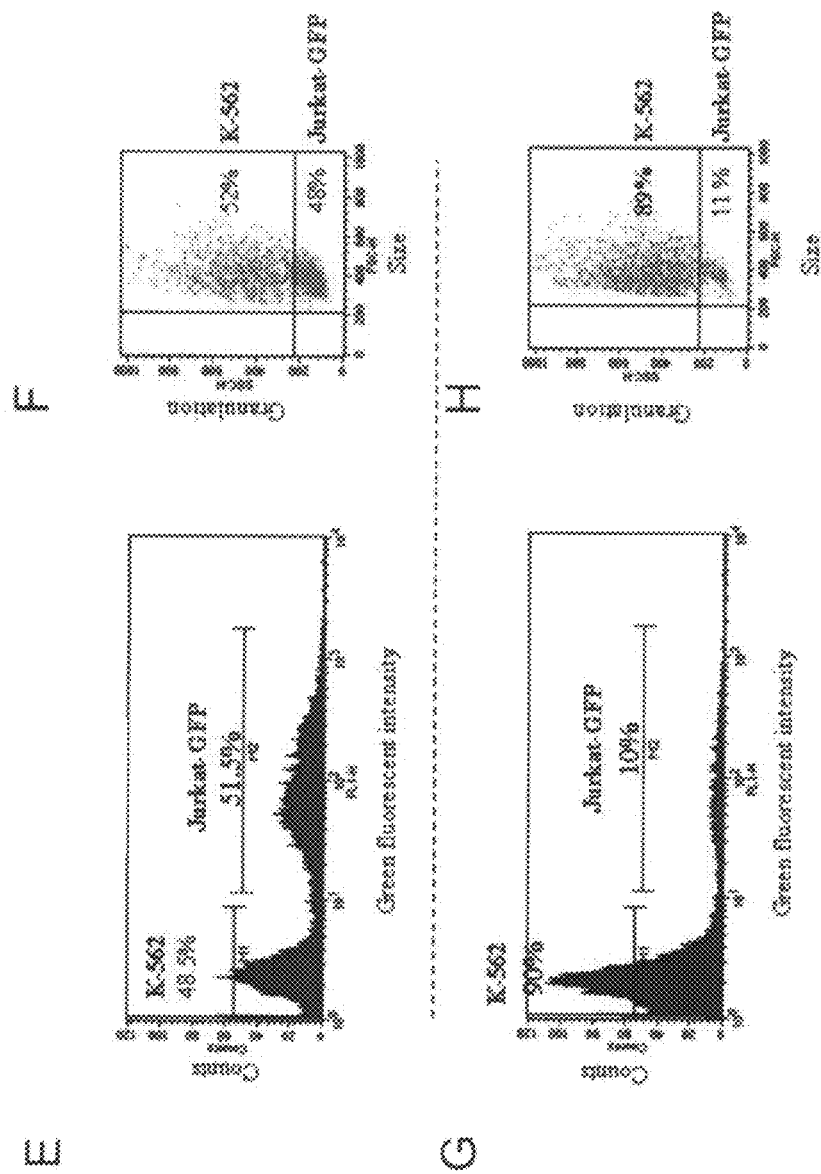
Figs. 41E-H

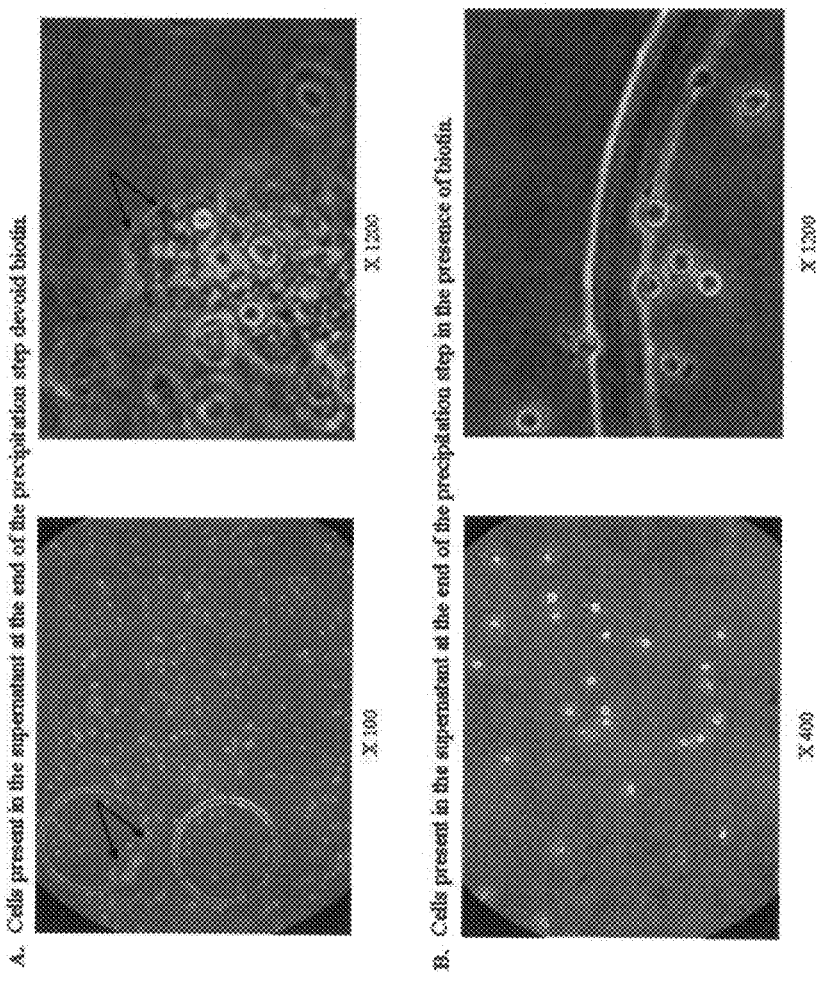
Figs. 42A-B

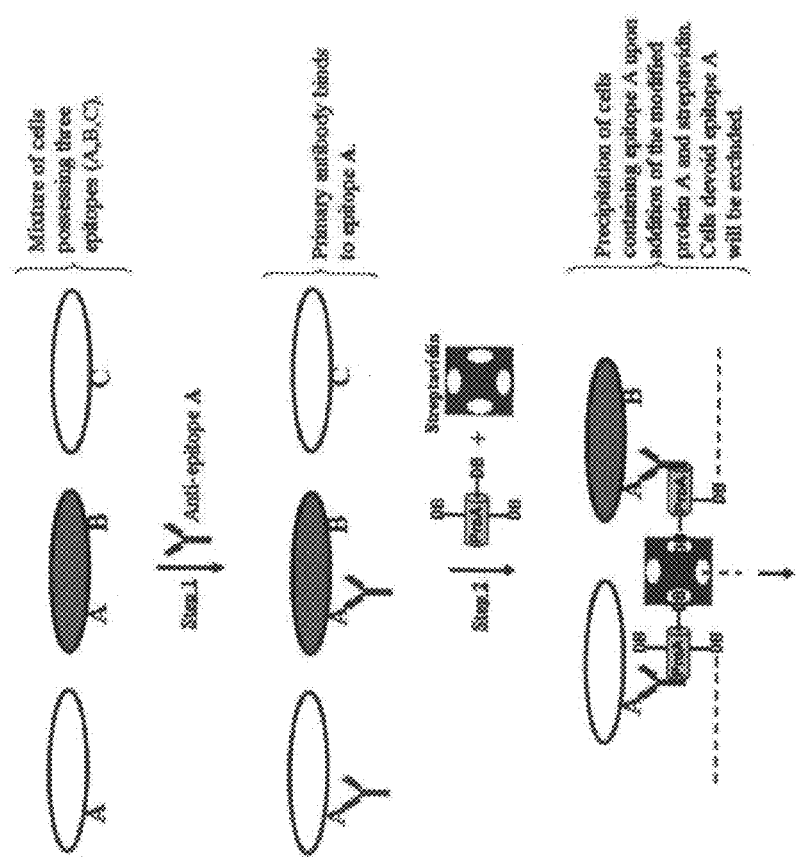
Fig. 51 (1/2)

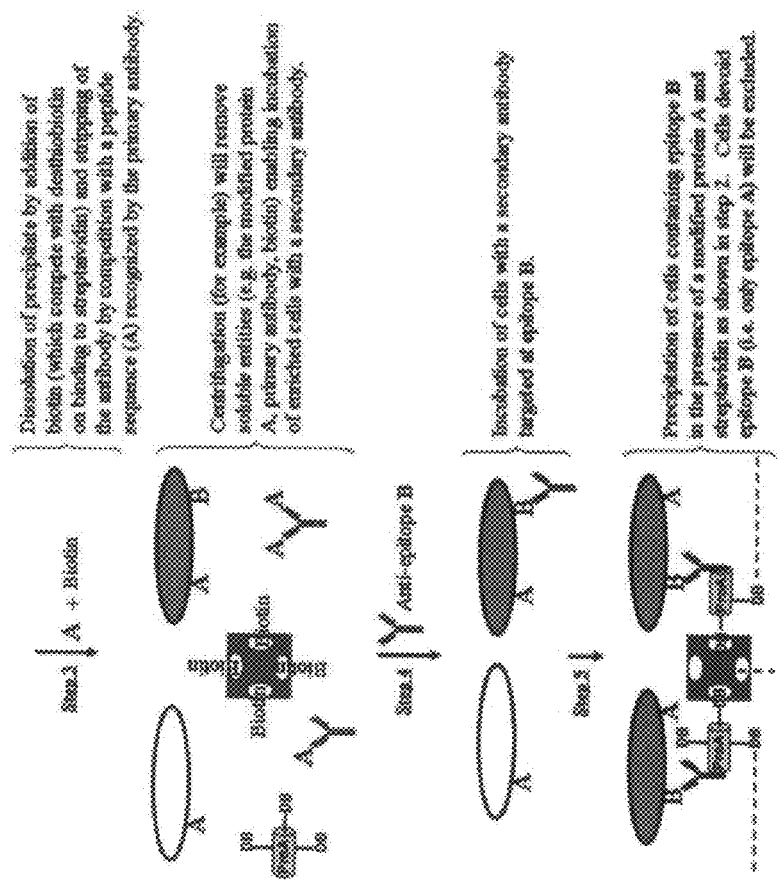
Fig. 51 (2/2)

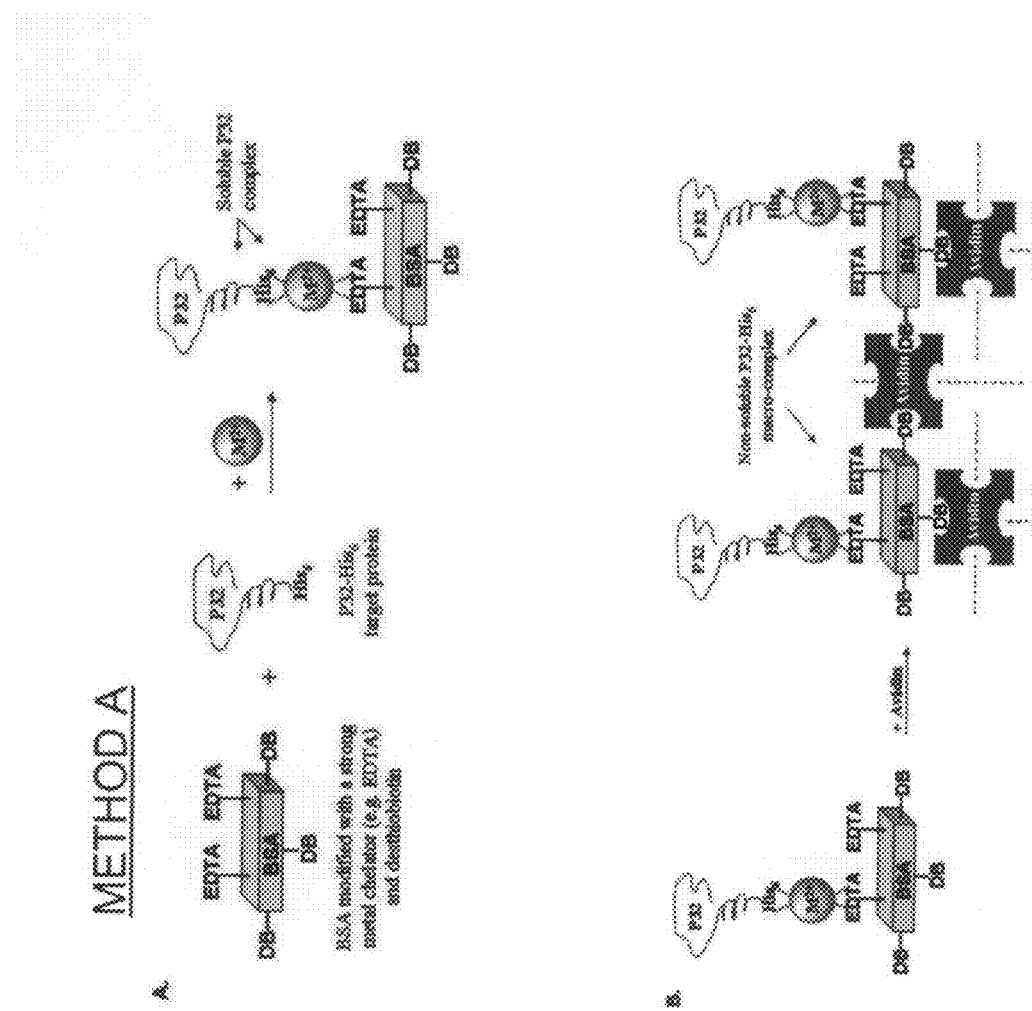
FIG. 53A-B

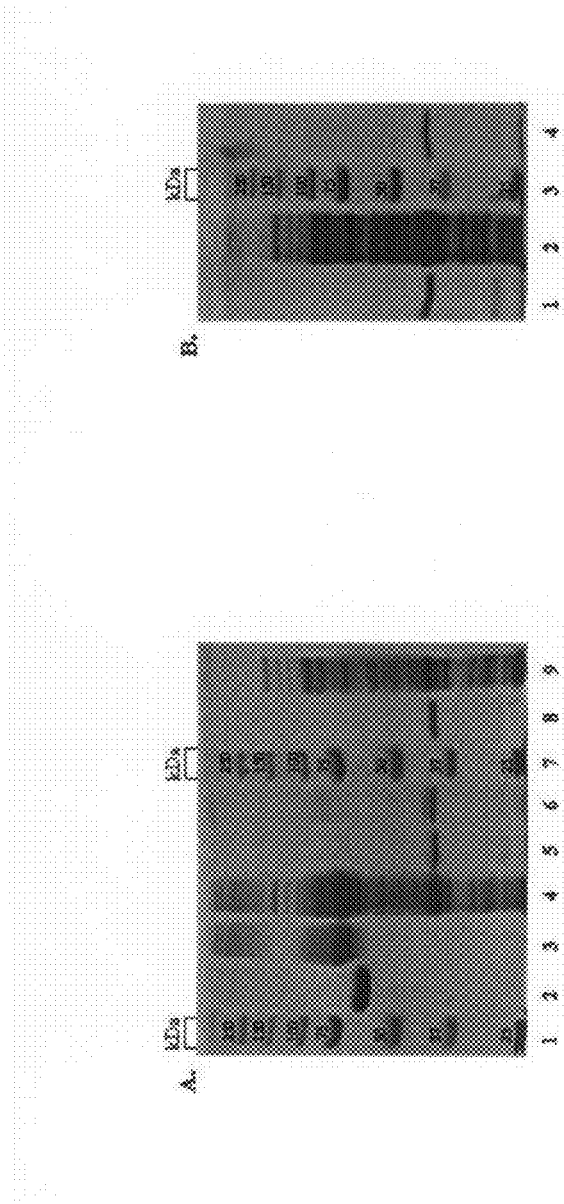
FIGs. 54A-B

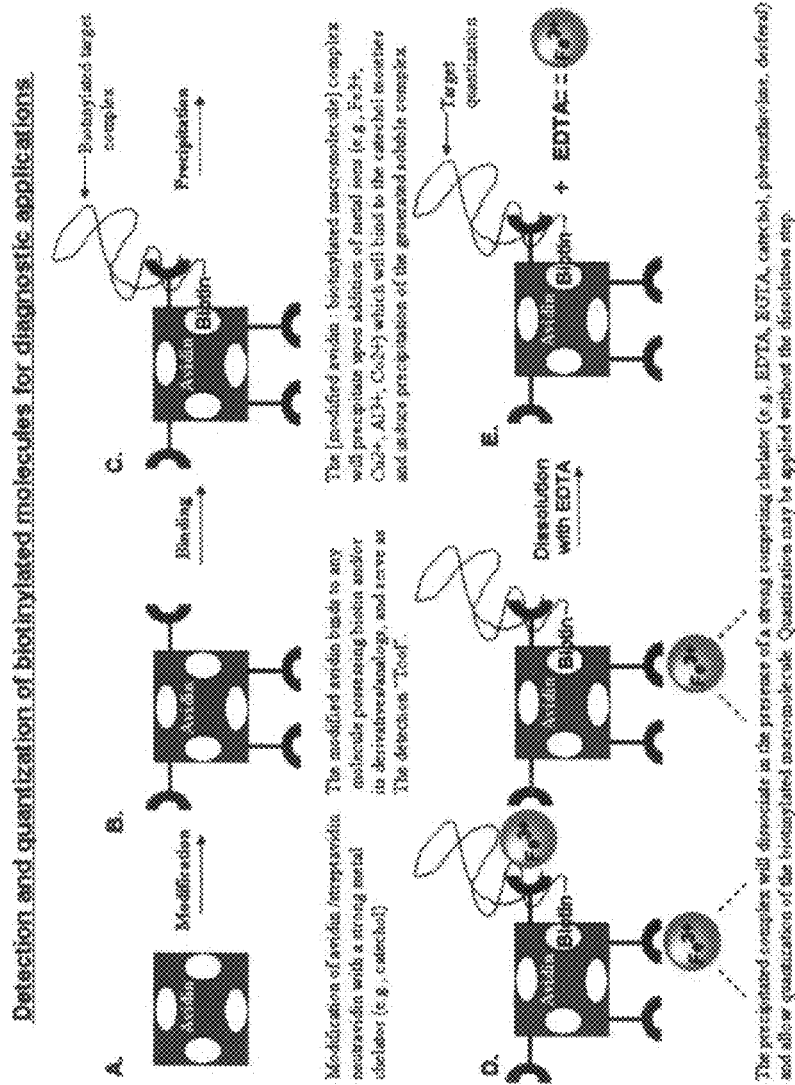
FIGs. 55A-E

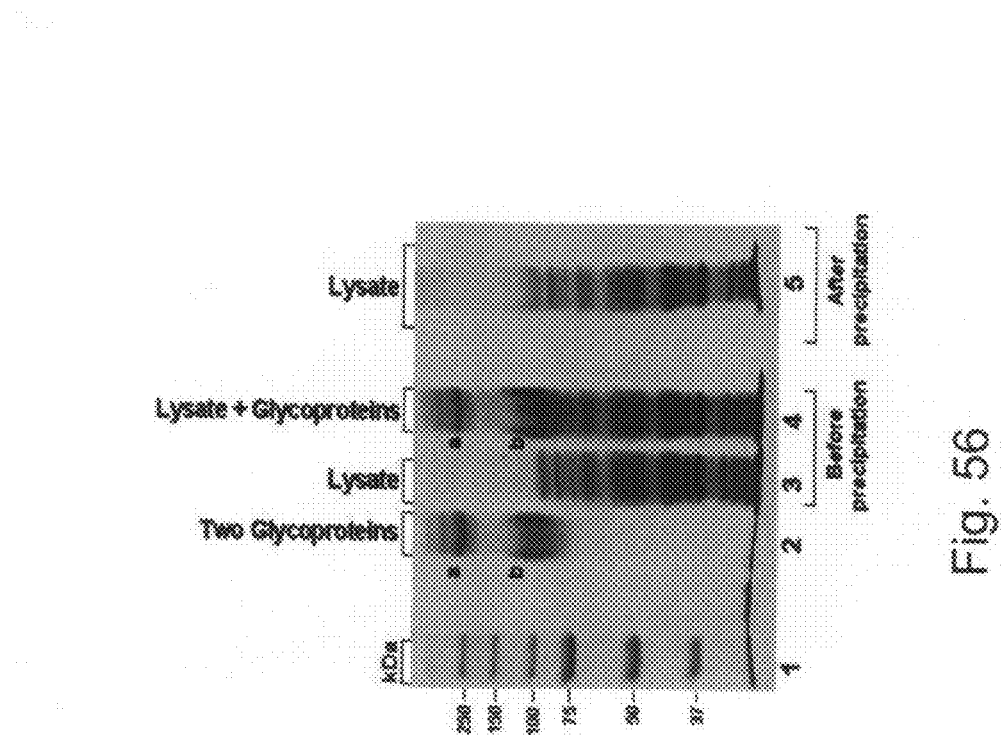

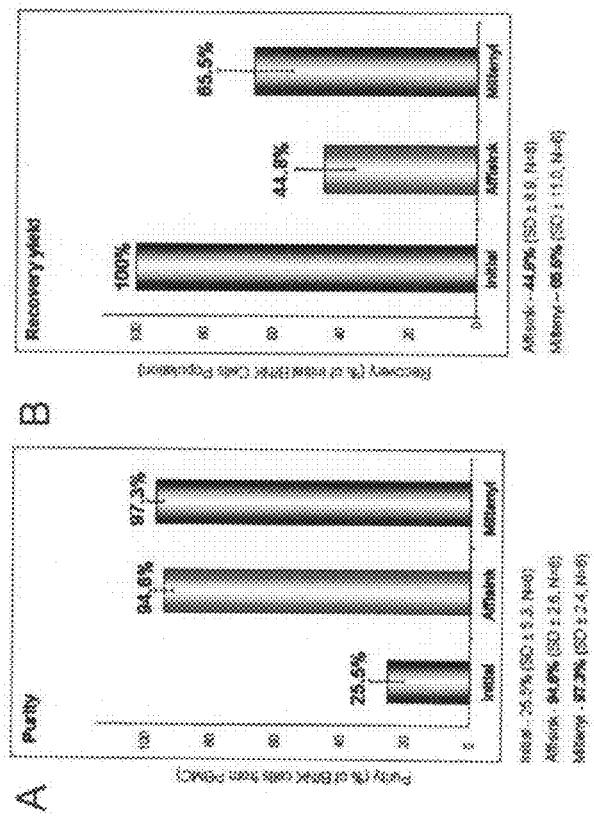
Figs. 57A-B
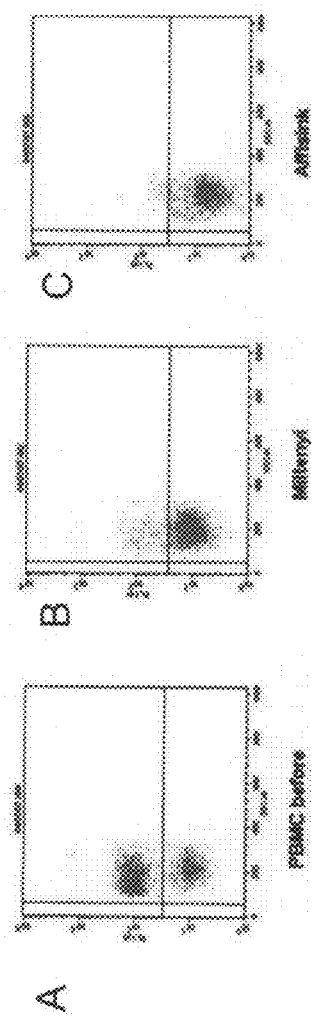
Figs. 58A-C

SEQUENCE LISTING

<160> NUMBER OF SEQ ID NOS: 3

<210> SEQ ID NO 1
<211> LENGTH: 360
<212> TYPE: PRT
<213> ORGANISM: Artificial sequence
<220> FEATURE:
<223> OTHER INFORMATION: Recombinant human Mitogen-activated protein
      kinase 14 isolated and analyzed by mass spec.

<400> SEQUENCE: 1

```
Met Ser Gln Glu Arg Pro Thr Phe Tyr Arg Gln Glu Leu Asn Lys Thr
1               5                   10                  15

Ile Trp Glu Val Pro Glu Arg Tyr Gln Asn Leu Ser Pro Val Gly Ser
            20                  25                  30

Gly Ala Tyr Gly Ser Val Cys Ala Ala Phe Asp Thr Lys Thr Gly Leu
        35                  40                  45

Arg Val Ala Val Lys Lys Leu Ser Arg Pro Phe Gln Ser Ile Ile His
    50                  55                  60

Ala Lys Arg Thr Tyr Arg Glu Leu Arg Leu Leu Lys His Met Lys His
65                  70                  75                  80

Glu Asn Val Ile Gly Leu Leu Asp Val Phe Thr Pro Ala Arg Ser Leu
                85                  90                  95

Glu Glu Phe Asn Asp Val Tyr Leu Val Thr His Leu Met Gly Ala Asp
            100                 105                 110

Leu Asn Asn Ile Val Lys Cys Gln Lys Leu Thr Asp Asp His Val Gln
        115                 120                 125

Phe Leu Ile Tyr Gln Ile Leu Arg Gly Leu Lys Tyr Ile His Ser Ala
130                 135                 140

Asp Ile Ile His Arg Asp Leu Lys Pro Ser Asn Leu Ala Val Asn Glu
145                 150                 155                 160

Asp Cys Glu Leu Lys Ile Leu Asp Phe Gly Leu Ala Arg His Thr Asp
                165                 170                 175

Asp Glu Met Thr Gly Tyr Val Ala Thr Arg Trp Tyr Arg Ala Pro Glu
            180                 185                 190

Ile Met Leu Asn Trp Met His Tyr Asn Gln Thr Val Asp Ile Trp Ser
        195                 200                 205

Val Gly Cys Ile Met Ala Glu Leu Leu Thr Gly Arg Thr Leu Phe Pro
210                 215                 220

Gly Thr Asp His Ile Asp Gln Leu Lys Leu Ile Leu Arg Leu Val Gly
225                 230                 235                 240

Thr Pro Gly Ala Glu Leu Leu Lys Lys Ile Ser Ser Glu Ser Ala Arg
                245                 250                 255

Asn Tyr Ile Gln Ser Leu Thr Gln Met Pro Lys Met Asn Phe Ala Asn
            260                 265                 270

Val Phe Ile Gly Ala Asn Pro Leu Ala Val Asp Leu Leu Glu Lys Met
        275                 280                 285

Leu Val Leu Asp Ser Asp Lys Arg Ile Thr Ala Ala Gln Ala Leu Ala
290                 295                 300

His Ala Tyr Phe Ala Gln Tyr His Asp Pro Asp Asp Glu Pro Val Ala
305                 310                 315                 320

Asp Pro Tyr Asp Gln Ser Phe Glu Ser Arg Asp Leu Leu Ile Asp Glu
                325                 330                 335

Trp Lys Ser Leu Thr Tyr Asp Glu Val Ile Ser Phe Val Pro Pro Pro
            340                 345                 350

Leu Asp Gln Glu Glu Met Glu Ser
        355                 360
```

<210> SEQ ID NO 2
<211> LENGTH: 57
<212> TYPE: DNA
<213> ORGANISM: Artificial sequence
<220> FEATURE:
<223> OTHER INFORMATION: Single strand DNA oligonucleotide

<400> SEQUENCE: 2

```
aataaccatg gcgcatcatc atcatcatca ttctcaggag aggcccacgt tctaccg        57

<210> SEQ ID NO 3
<211> LENGTH: 33
<212> TYPE: DNA
<213> ORGANISM: Artificial sequence
<220> FEATURE:
<223> OTHER INFORMATION: Single strand DNA oligonucleotide

<400> SEQUENCE: 3
attggatcct caggactcca tctcttcttg gtc                                 33
```

COMPOSITIONS AND METHODS FOR PURIFYING AND CRYSTALLIZING MOLECULES OF INTEREST

RELATED APPLICATIONS

This application is a continuation-in-part of PCT Patent Application No. PCT/IL2006/000173 filed Feb. 9, 2006, which claims the benefit of Israel Patent Application No. 166800 filed Feb. 10, 2005, and which is also a continuation-in-part of pending U.S. patent application Ser. No. 11/330,112 filed Jan. 12, 2006, which is a continuation-in-part of PCT Patent Application No. PCT/IL2004/000669 filed Jul. 22, 2004, which claims the benefit of Israel Patent Application No. 157086, filed Jul. 24, 2003.

The contents of the above applications are incorporated herein by reference.

FIELD AND BACKGROUND OF THE INVENTION

The present invention relates to compositions, which can be used for purifying and crystallizing molecules of interest.

Proteins and other macromolecules are increasingly used in research, diagnostics and therapeutics. Proteins are typically produced by recombinant techniques on a large scale with purification constituting the major cost (up to 60% of the total cost) of the production processes. Thus, large-scale use of recombinant protein products is hindered because of the high cost associated with purification.

Current protein purification methods are dependent on the use of a combination of various chromatography techniques. These techniques separate mixtures of proteins on the basis of their charge, degree of hydrophobicity or size among other characteristics. Several different chromatography resins are available for use with each of these techniques, allowing accurate tailoring of the purification scheme to the particular protein targeted for isolation. The essence of each of these separation methods is that proteins can be caused either to move at different rates down a long column, achieving a physical separation that increases as they pass further down the column, or to adhere selectively to the separation medium, enabling differential elution by different solvents. In some cases, the column is designed such that impurities bind thereto while the desired protein is found in the "flow-through."

Affinity precipitation (AP) is the most effective and advanced approach for protein precipitation [Mattiasson (1998); Hlibrig and Freitag (2003) J Chromatogr B Analyt Technol Biomed Life Sci. 790(1-2):79-90]. Current state of the art AP employs ligand coupled "smart polymers". "Smart polymers" [or stimuli-responsive "intelligent" polymers or Affinity Macro Ligands (AML)] are polymers that respond with large property changes to small physical or chemical stimuli, such as changes in pH, temperature, radiation and the like. These polymers can take many forms; they may be dissolved in an aqueous solution, adsorbed or grafted on aqueous-solid interfaces, or cross-linked to form hydrogels [Hoffman J Controlled Release (1987) 6:297-305; Hoffman Intelligent polymers. In: Park K, ed. Controlled drug delivery. Washington: ACS Publications, (1997) 485-98; Hoffman Intelligent polymers in medicine and biotechnology. Artif Organs (1995) 19:458-467]. Typically, when the polymer's critical response is stimulated, the smart polymer in solution will show a sudden onset of turbidity as it phase-separates; the surface-adsorbed or grafted smart polymer will collapse, converting the interface from hydrophilic to hydrophobic; and the smart polymer (cross-linked in the form of a hydrogel) will exhibit a sharp collapse and release much of its swelling solution. These phenomena are reversed when the stimulus is reversed, although the rate of reversion often is slower when the polymer has to redissolve or the gel has to re-swell in aqueous medium.

"Smart" polymers may be physically mixed with, or chemically conjugated to, biomolecules to yield a large family of polymer-biomolecule systems that can respond to biological as well as to physical and chemical stimuli. Biomolecules that may be polymer-conjugated include proteins and oligopeptides, sugars and polysaccharides, single- and double-stranded oligonucleotides and DNA plasmids, simple lipids and phospholipids, and a wide spectrum of recognition ligands and synthetic drug molecules.

A number of structural parameters control the ability of smart polymers to specifically precipitate proteins of interest; smart polymers should contain reactive groups for ligand coupling; not interact strongly with the impurities; make the ligand available for interaction with the target protein; give complete phase separation of the polymer upon a change of medium property; form compact precipitates; exclude trapping of impurities into the gel structure and be easily solubilized after the precipitate is formed.

Although many different natural as well as synthetic polymers have been utilized in AP [Mattiasson (1998) J. Mol. Recognit. 11:211] the ideal smart polymers remain elusive, as affinity precipitations performed with currently available smart polymers, fail to meet one or several of the above-described requirements [Hlibrig and Freitag (2003), supra].

The availability of efficient and simple protein purification techniques may also be useful in protein crystallization, in which protein purity extensively affects crystal growth. The conformational structure of proteins is a key to understanding their biological functions and to ultimately designing new drug therapies. The conformational structures of proteins are conventionally determined by x-ray diffraction from their crystals. Unfortunately, growing protein crystals of sufficient high quality is very difficult in most cases, and such difficulty is the main limiting factor in the scientific determination and identification of the structures of protein samples. Prior art methods for growing protein crystals from super-saturated solutions are tedious and time-consuming, and less than two percent of the over 100,000 different proteins have been grown as crystals suitable for x-ray diffraction studies.

Membrane proteins present the most challenging group of proteins for crystallization. The number of 3D structures available for membrane proteins is still around 20 while the number of membrane proteins is expected to constitute a third of the proteome. Numerous obstacles need to be traversed when wishing to crystallize a membrane protein. These include, low abundance of proteins from natural sources, the need to solubilize hydrophobic membrane proteins from their native environment (i.e., the lipid bilayer) and their tendency to denaturate, aggregate and/or degrade in the detergent solution. The choice of the solubilizing detergent presents another problem as some detergents may interfere with binding of a stabilizing partner to the target protein.

Two approaches have been attempted in the crystallization of membrane proteins.

Until very recently, the majority of X-ray crystal structures of membrane proteins have been determined using crystals grown directly from solutions of protein-detergent complexes. Crystal growth of protein-detergent complexes can be considered equivalent to that of soluble proteins only the solute being crystallized is a complex of protein and detergent, rather than solely protein. The actual lattice contacts are formed by protein-protein interactions, although crystal packing brings the detergent moieties into close apposition as well. In order to increase the surface area available to make these protein-protein contacts studies suggested adding an antibody fragment which will increase the chances of producing crystals [Hunte and Michel (2002) Curr. Opin. Struct. Biol. 12:503-508]. However, applying this technology to various membrane proteins is difficult as it requires the generation of monoclonal antibodies, which are specific to each membrane protein.

Furthermore, it is argued that no detergent micelle can fully and accurately reproduce the lipid bilayer environment of the protein.

Thus, efforts to crystallize membrane proteins must be directed towards producing crystals within a bilayer environment. A number of attempts have been made to generate crystals of membrane proteins using this approach. These include the generation of crystals of bacteriorhodopsin grown in the presence of a lipidic cubic phase, which forms gel-like substance containing continuous bilayer structures [Landau and Rosenbuch (1996) Proc. Natl. Acad. Sci. USA 93:14532-14535] and crystallization in cubo which was proven successful in the crystallization of archaeal seven-transmembrane helix proteins [Gordeliy (2002) Nature 419:484-487; Luecke (2001) Science 293:1499-1503; Kolbe (2000) Science 288:1390-1396; Royant (2001) Proc. Natl. Acad. Sci. USA 98:10131-10136]. However, crystals of other membrane proteins using the in cubo approach were not of as high a quality as crystals grown directly from protein-detergent complex solutions [Chiu (2000) Acta. Crystallogr. D. 56:781-784].

There is thus a widely recognized need for, and it would be highly advantageous to have, compositions and methods using same for the purification and crystallization of molecules which are devoid of the above limitations.

SUMMARY OF THE INVENTION

According to one aspect of the present invention there is provided a composition-of-matter comprising at least one antibody binding moiety capable of binding an antibody-labeled target molecule, cell or virus of interest, the at least one antibody binding moiety being attached to at least two coordinating moieties selected capable of directing the composition-of-matter to form a non-covalent complex when co-incubated with a coordinator ion or molecule.

According to further features in preferred embodiments of the invention described below, the target cell is a prokaryotic cell.

According to still further features in the described preferred embodiments the target cell is a eukaryotic cell.

According to still further features in the described preferred embodiments the eukaryotic cell is a stem cell or a cancer cell.

According to still further features in the described preferred embodiments the antibody-labeled molecule, target cell or virus comprises at least two distinct antibody labels.

According to still further features in the described preferred embodiments the antibody binding moiety is selected from the group consisting of a protein A, a protein G, a protein L and a fragment thereof.

According to still further features in the described preferred embodiments the antibody binding moiety comprise an antibody or an antibody fragment.

According to still further features in the described preferred embodiments the complex is a polymeric complex.

According to still further features in the described preferred embodiments the composition further comprising the coordinator ion or molecule.

According to still further features in the described preferred embodiments the at least one antibody binding moiety is attached to the at least one coordinating moiety via a linker.

According to still further features in the described preferred embodiments the coordinating moieties are selected from the group consisting of a biotin, a nucleic acid sequence, an epitope tag, an electron poor molecule and an electron-rich molecule.

According to still further features in the described preferred embodiments the coordinating moieties comprise a chelator.

According to still further features in the described preferred embodiments the coordinator ion or molecule is selected from the group consisting of an avidin, a nucleic acid sequence, an electron poor molecule and an electron-rich molecule.

According to still further features in the described preferred embodiments the coordinator ion or molecule is a metal ion.

According to still further features in the described preferred embodiments the molecule is a toxin or a prion.

According to still further features in the described preferred embodiments the toxin is an endotoxin.

According to still further features in the described preferred embodiments the at least one antibody binding moiety is non-immobilized.

According to still further features in the described preferred embodiments the at least one coordinating moiety comprise desthiobiotin.

According to still further features in the described preferred embodiments the coordinator comprise a monomeric or oligomeric avidnin analog.

According to still further features in the described preferred embodiments the avidin analog comprise streptavidin or nuravidin.

According to another aspect of the present invention there is provided a method of purifying a target molecule, cell or a virus of interest, the method comprising: (a) labeling the target molecule, cell or the virus with at least one antibody, so as to obtain antibody labeled target molecule, cell or the virus; (b) contacting the antibody labeled target molecule, cell or the virus with the composition so as to form a precipitate including the complex bound to the target molecule cell or the virus; and (c) collecting the precipitate, thereby purifying the molecule, target molecule or cell of interest.

According to still further features in the described preferred embodiments the step a and step b are effected sequentially.

According to still further features in the described preferred embodiments the step a and step b are effected concomitantly.

According to still further features in the described preferred embodiments the method further comprising recovering the target molecule, cell or the virus from the precipitate.

According to still further features in the described preferred embodiments the steps (a) and (b) are effected in a tube and the method further comprising spinning the tube around its axis so as to promote formation of the precipitate following step (b).

According to still further features in the described preferred embodiments the collecting the precipitate is effected by size filtration and/or densitometry.

According to still further features in the described preferred embodiments the recovering is effected in a presence of biotin when the coordinating moiety is desthiobiotin.

According to still further features in the described preferred embodiments the purifying is effected so as to obtain about 95% purity of the target cell of interest.

According to still further features in the described preferred embodiments the purifying is effected so as to obtain at least about 45% yield of the target cell of interest.

According to yet another aspect of the present invention there is provided a method of depleting a target molecule, cell or virus of interest from a sample, the method comprising: (a) labeling the target molecule, cell or the virus with an antibody, so as to obtain antibody labeled target molecule cell or the virus; (b) contacting the antibody labeled target molecule, cell or the virus with the composition so as to form a precipitate including the complex bound to the target molecule cell or the virus; and (c) removing the precipitate to thereby deplete the target molecule or cell of interest from the sample.

According to still further features in the described preferred embodiments steps (a) and (b) are effected in a tube and the method further comprising spinning the tube around its axis so as to promote formation of the precipitate following step (b).

According to still further features in the described preferred embodiments the removing the precipitate is effected by size filtration and/or densitometry.

According to still another aspect of the present invention there is provided a kit for isolating a target molecule cell or a virus of interest from a biological sample, the kit comprising a packaging material which comprises the composition-of-matter.

According to still further features in the described preferred embodiments the kit further comprising an antibody for specifically labeling the target molecule, cell or the virus.

According to still further features in the described preferred embodiments the composition-of-matter is non-immobilized.

According to still further features in the described preferred embodiments the antibody is non-immobilized.

According to an additional aspect of the present invention there is provided a method of detecting predisposition to, or presence of a disease associated with a molecule, a cell or virus of interest in a subject, the method comprising contacting an immunolabeled biological sample obtained from the subject with the composition, wherein formation of the complex including the molecule, cell or virus of interest is indicative of predisposition to, or presence of the disease associated with the molecule, cell or virus of interest in the subject.

According to yet an additional aspect of the present invention there is provided a composition-of-matter comprising at least one ligand capable of binding a target molecule or cell of interest, the at least one ligand being a composite ligand which comprises a scaffold moiety attached to at least one target recognition moiety capable of directly or indirectly binding the target molecule, cell or virus, the at least one ligand being attached to at least two coordinating moieties selected capable of directing the composition-of-matter to form a non-covalent complex when co-incubated with a coordinator ion or molecule.

According to still further features in the described preferred embodiments the scaffold moiety comprise albumin.

According to still further features in the described preferred embodiments the albumin is selected from the group consisting of bovine serum albumin, Human serum albumin (HSA) and ovalbumin.

According to still further features in the described preferred embodiments the target recognition moiety is selected from the group consisting of glutathione, a nucleic acid sequence, an amino acid sequence, a hormone, a histidine, a protease substrate, a protease inhibitor, a lectin, a LacI, a Cibarcon blue, a zinc finger protein and a chelator.

According to still further features in the described preferred embodiments the at least one ligand is non-immobilized.

According to still an additional aspect of the present invention there is provided a method of purifying at least one target molecule, cell or a virus of interest, the method comprising: (a) contacting the target molecule, cell or the virus with the composition so as to form a precipitate including the complex bound to the target molecule cell or the virus; and (b) collecting the precipitate, thereby purifying the at least one molecule, target molecule or cell of interest.

According to still further features in the described preferred embodiments the step a and step b are effected sequentially.

According to still further features in the described preferred embodiments the step a and step b are effected concomitantly.

According to still further features in the described preferred embodiments the method further comprising recovering the target molecule, cell or the virus from the precipitate.

According to still further features in the described preferred embodiments the steps (a) and (b) are effected in a tube and the method further comprising spinning the tube around its axis so as to promote formation of the precipitate following step (b).

According to still further features in the described preferred embodiments the collecting the precipitate is effected by size filtration and/or densitometry.

According to still further features in the described preferred embodiments the recovering is effected in a presence of biotin when the coordinating moiety is desthiobiotin.

According to a further aspect of the present invention there is provided a method of depleting at least one target molecule, cell or virus of interest from a sample, the method comprising: (a) contacting the target molecule, cell or the virus with the composition so as to form a precipitate including the complex bound to the target molecule cell or the virus; and (b) removing the precipitate to thereby deplete the at least one target molecule or cell of interest from the sample.

According to still further features in the described preferred embodiments the removing the precipitate is effected by size filtration and/or densitometry.

According to still further features in the described preferred embodiments the at least one target molecule comprise immunoglobulins and bovine serum albumin.

According to yet a further aspect of the present invention there is provided a composition-of-matter comprising at least one ligand capable of binding a His-tagged molecule, the at least one ligand being a composite ligand which comprises an scaffold moiety attached to at least one chelator molecule capable of indirectly binding the His-Tagged molecule via a metal ion, the at least one ligand being attached to at least two coordinating moieties selected capable of directing the composition-of-matter to form a non-covalent complex when co-incubated with a coordinator ion or molecule.

According to still further features in the described preferred embodiments wherein the metal ion is different from the coordinator ion.

According to still a further aspect of the present invention there is provided a method of purifying at least one His-tagged molecule, the method comprising: (a) contacting the His-tagged molecule with the composition so as to form a precipitate including the complex bound to the His-tagged molecule; and (b) collecting the precipitate, thereby purifying the at least one molecule, target molecule or cell of interest.

According to still further features in the described preferred embodiments the purifying is effected under homogeneous conditions.

According to still further features in the described preferred embodiments the purifying is effected under heterogeneous conditions.

The present invention successfully addresses the shortcomings of the presently known configurations by providing compositions and methods for the purification of molecules.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The file of this patent contains at least one drawing executed in color photograph. Copies of this patent with color photographs(s) will be provided by the Patent and Trademark Office upon request and payment of necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

Figure 2A:
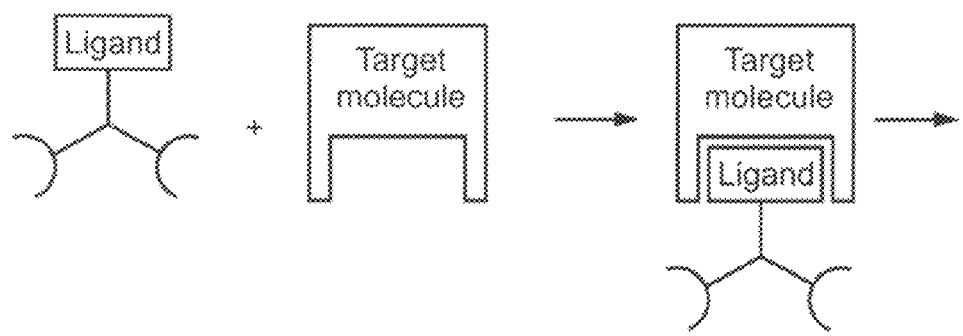
Figure 2B:
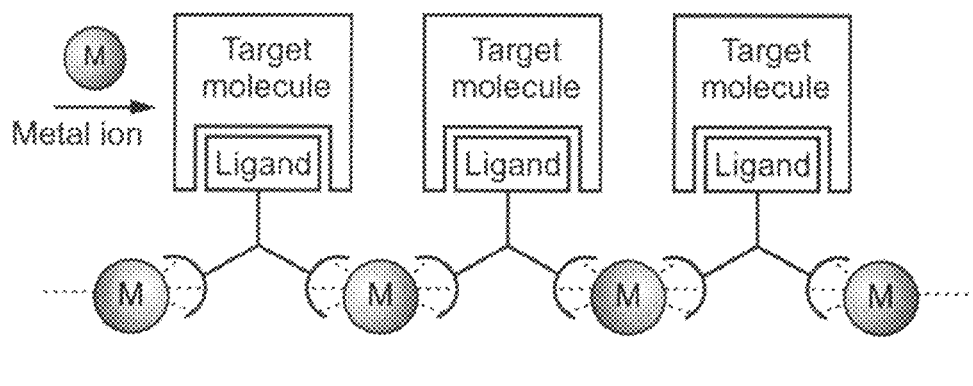
Figure 3A:
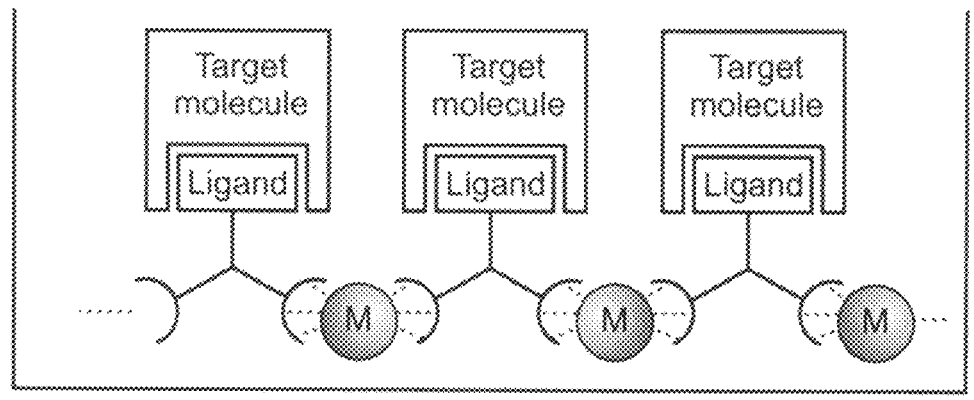
Figure 3B:
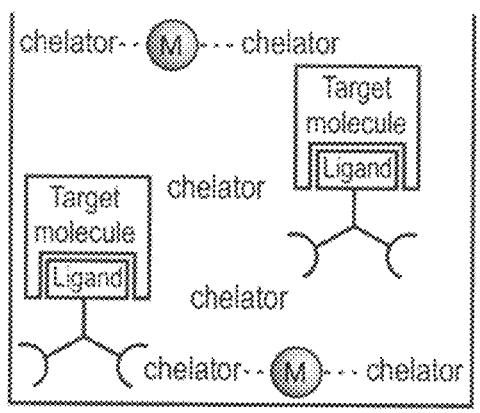
Figure 3C:
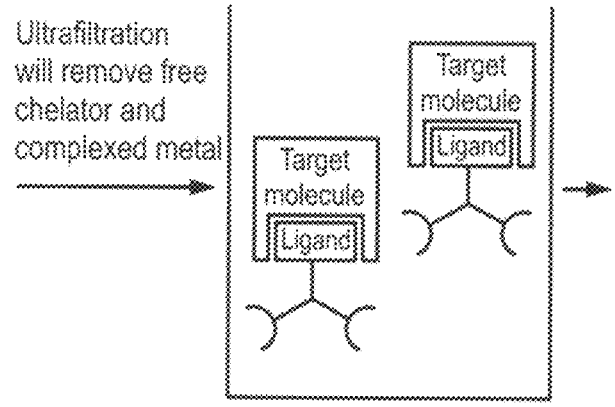
Figures 3D, 3E:
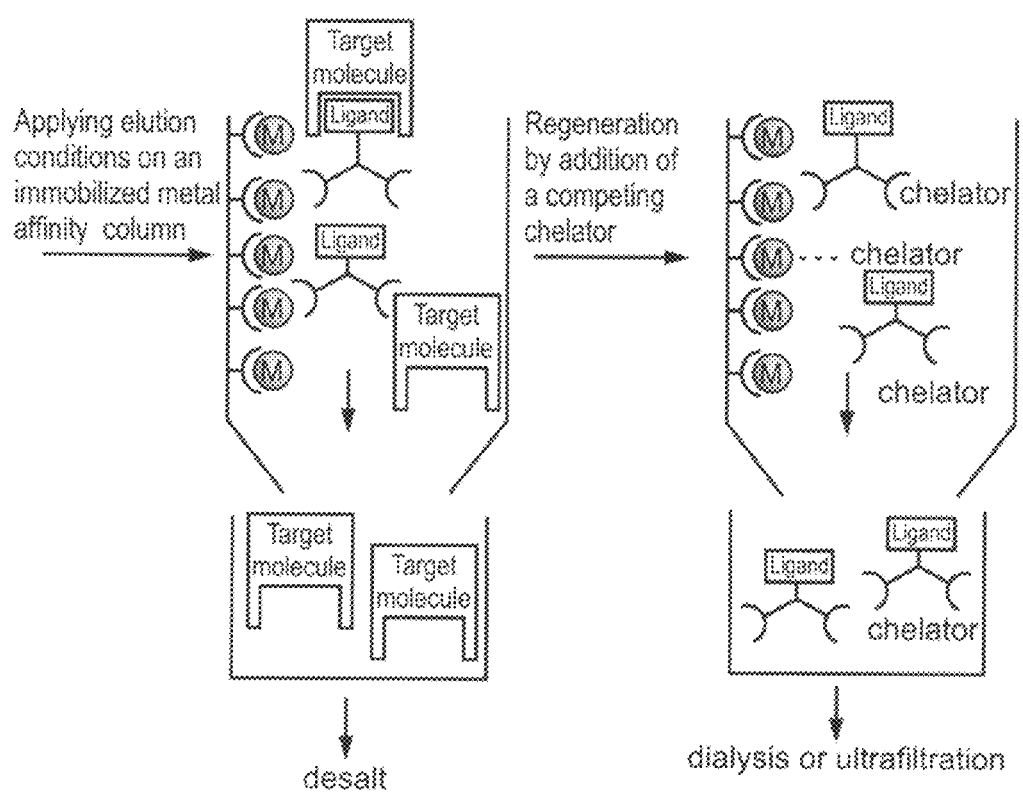
Figure 4:
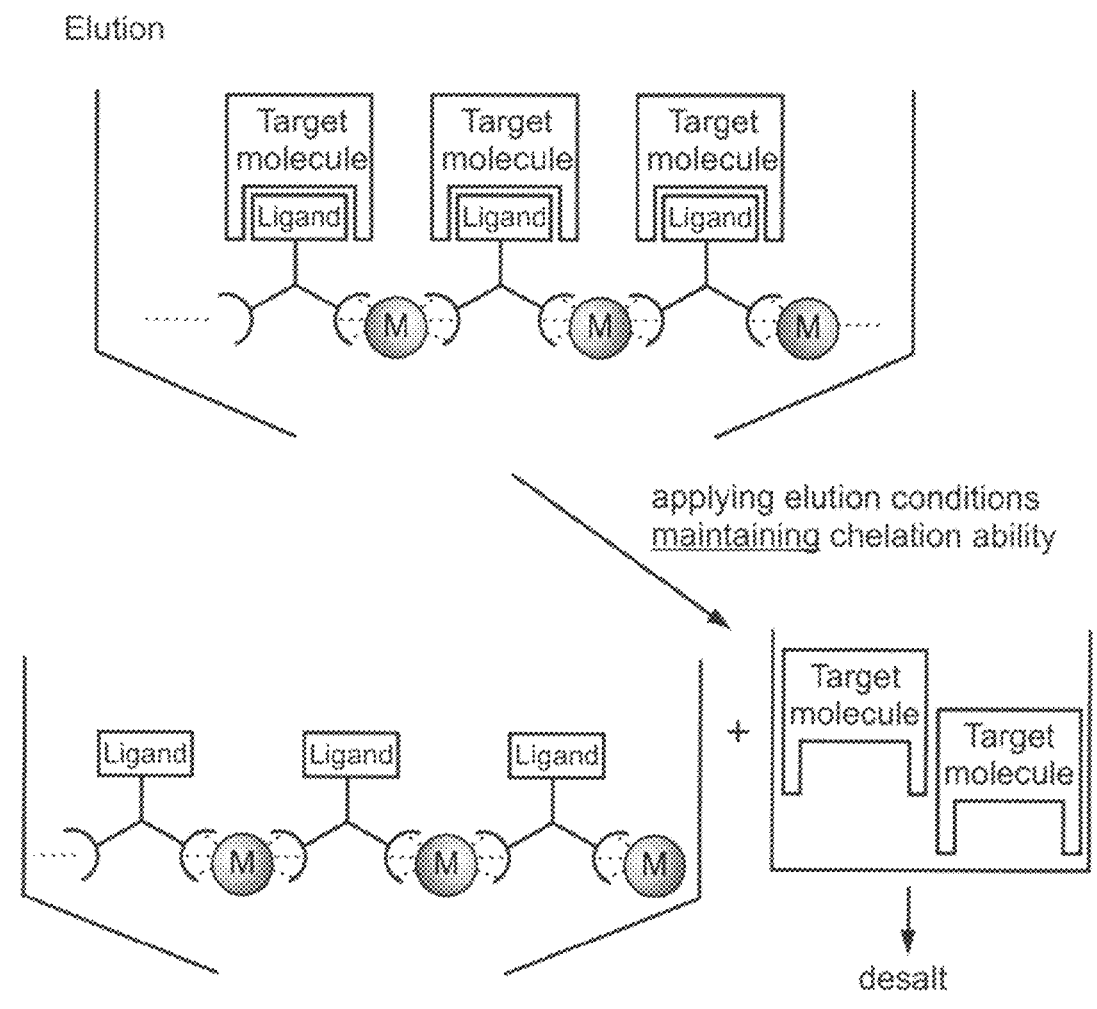
Figure 5:
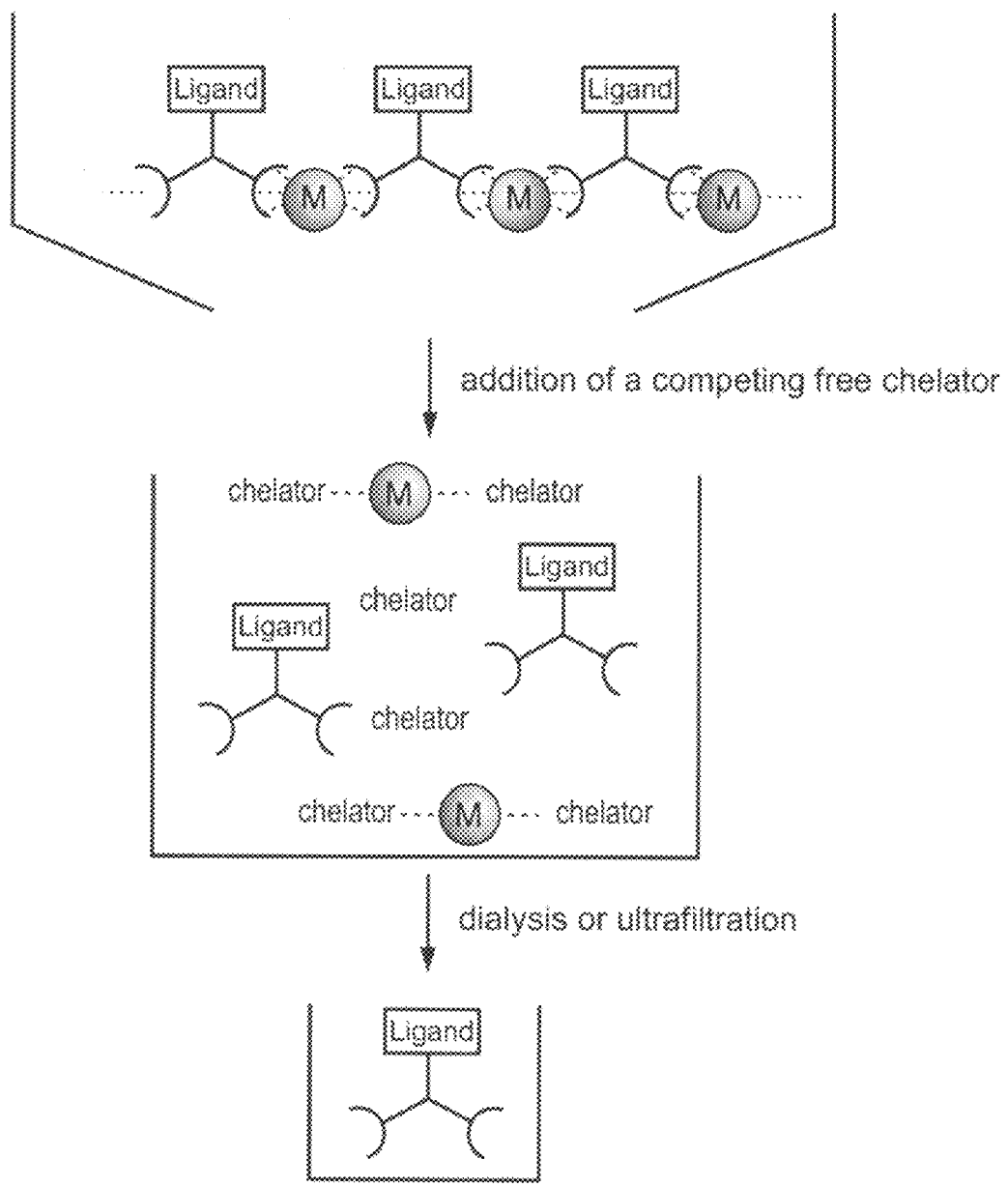
Figure 6A:
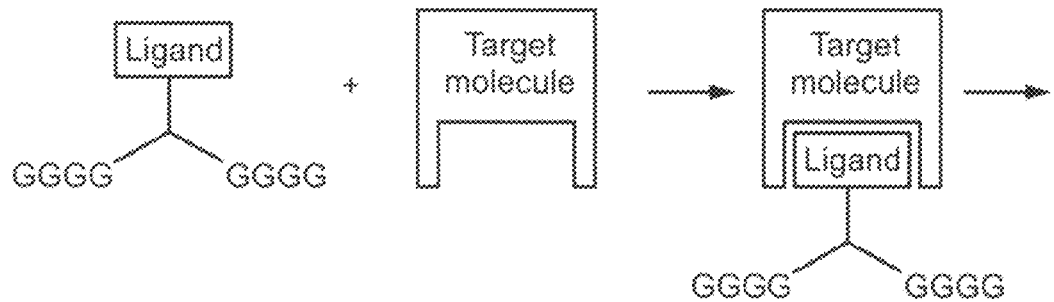
Figure 6B:
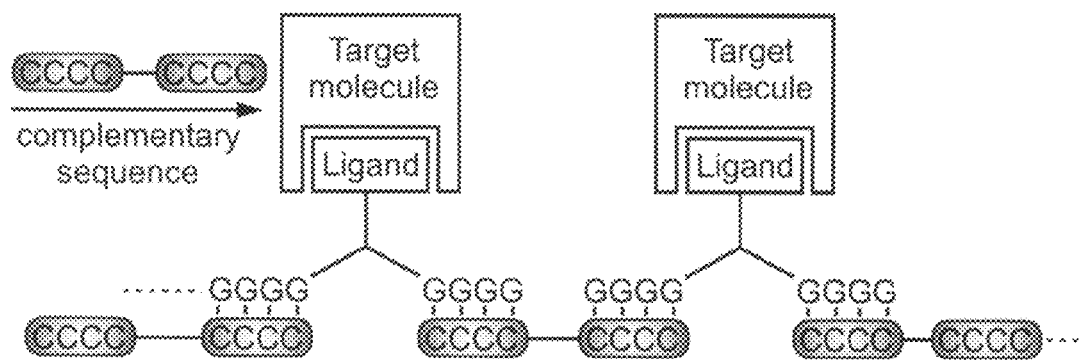
Figure 6C:
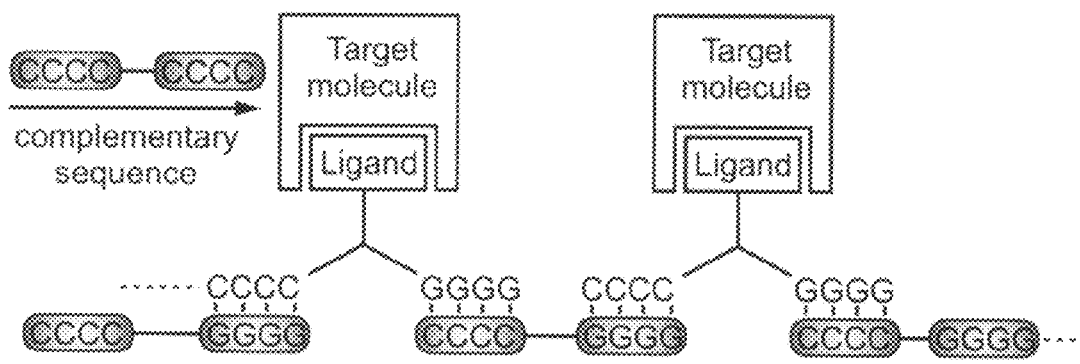
Figure 7A:
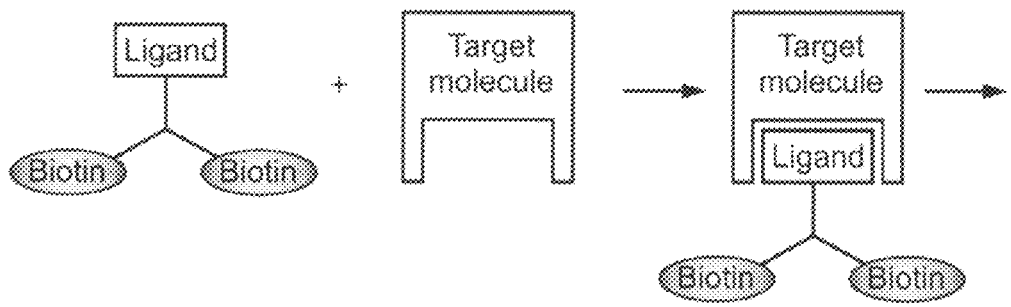
Figure 7B:
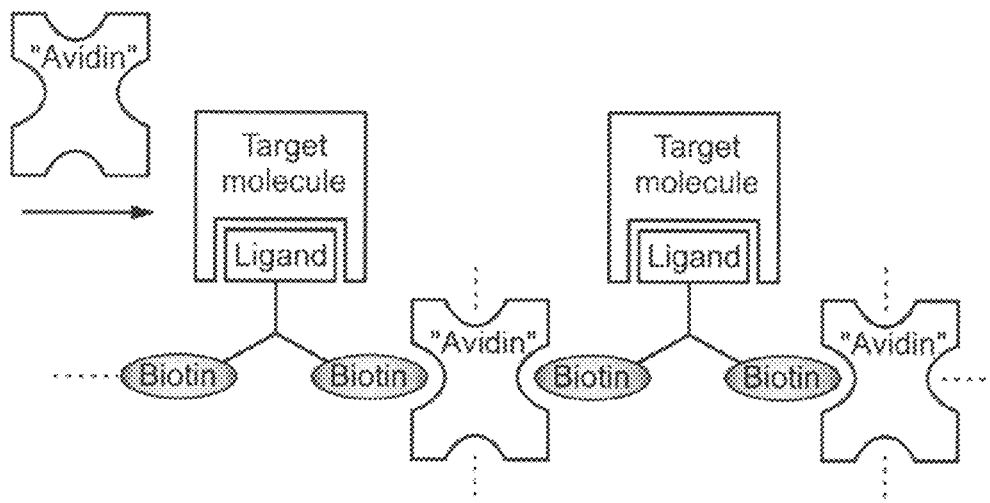
Figure 8A:
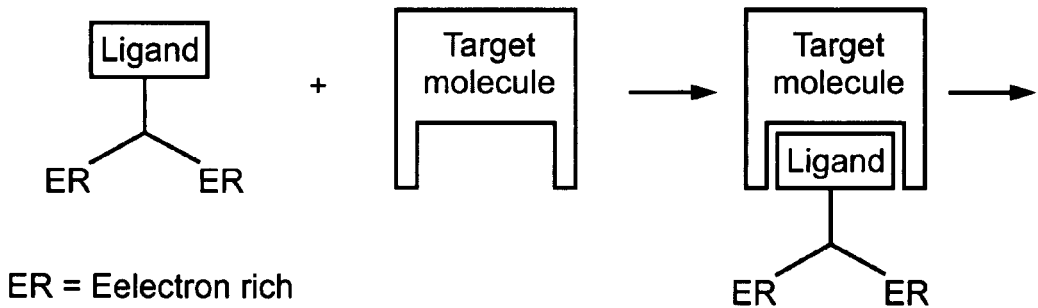
Figure 8B:
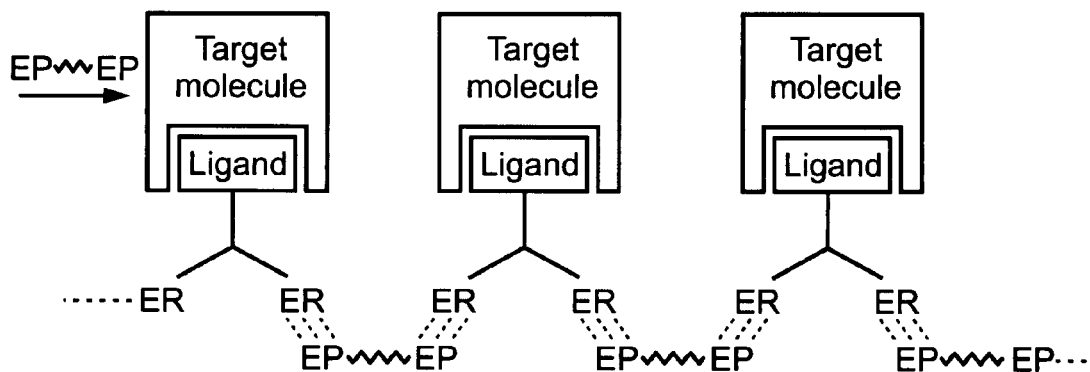
Figure 8C:
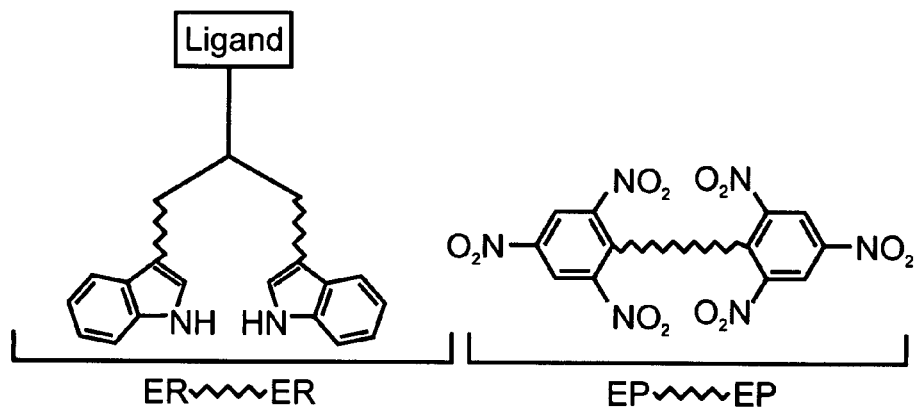
Figure 9:
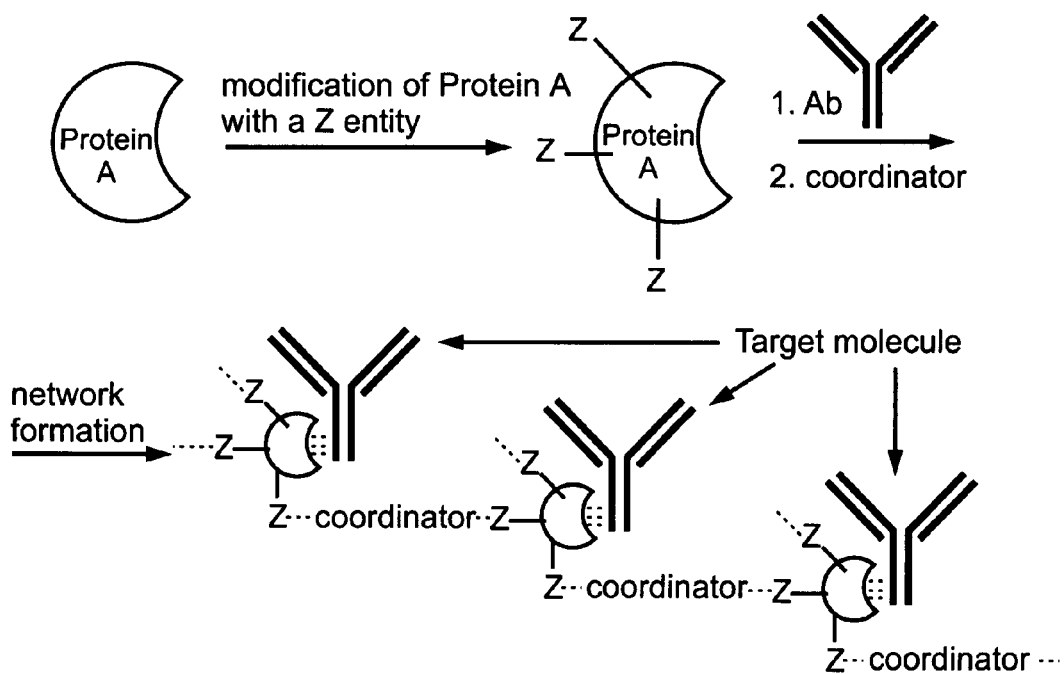
Figure 10A:
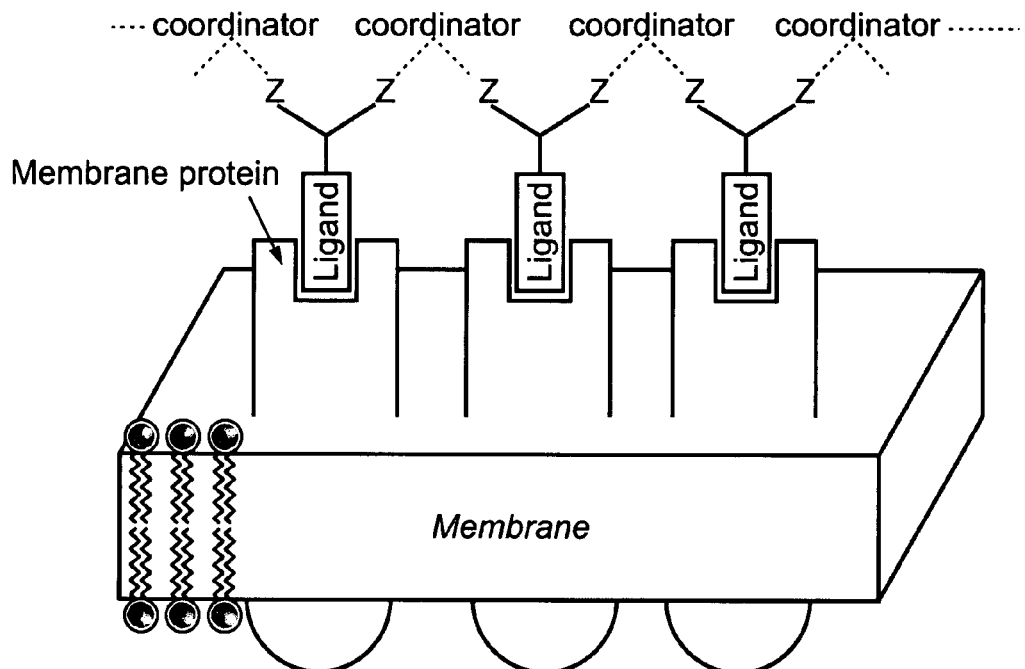
Figure 10B:
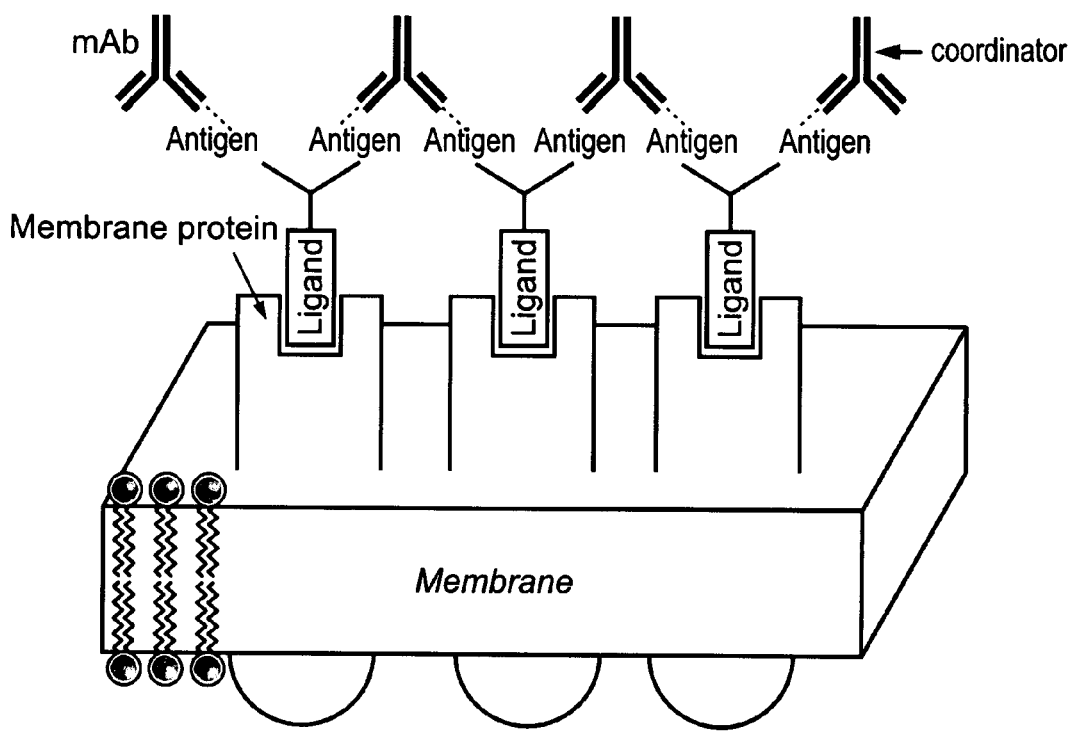
Figure 11A:
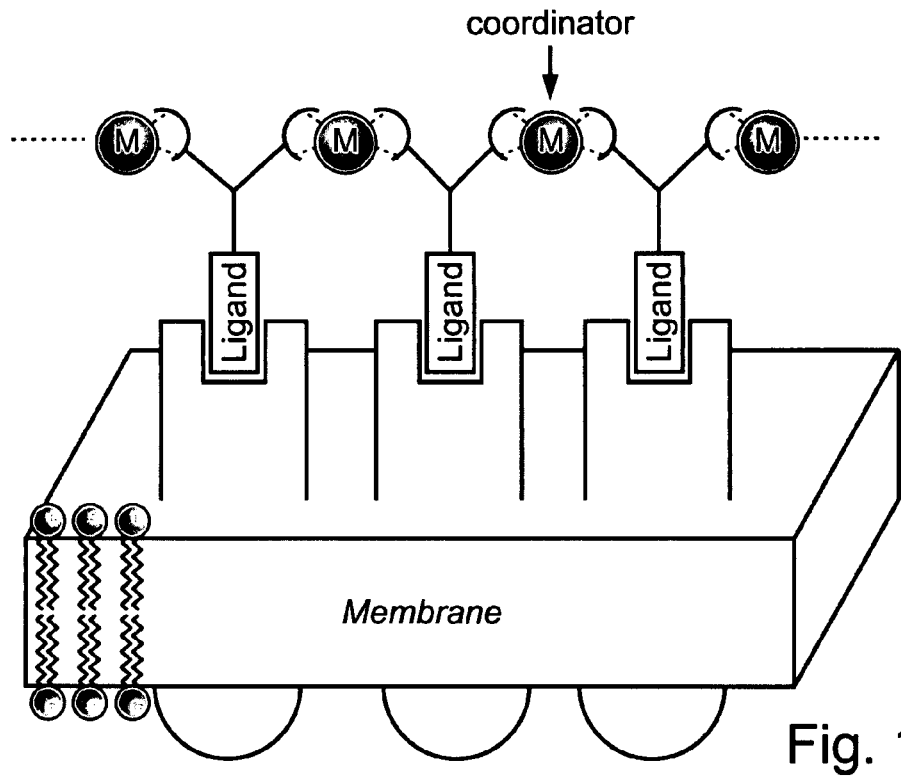
Figure 11B:
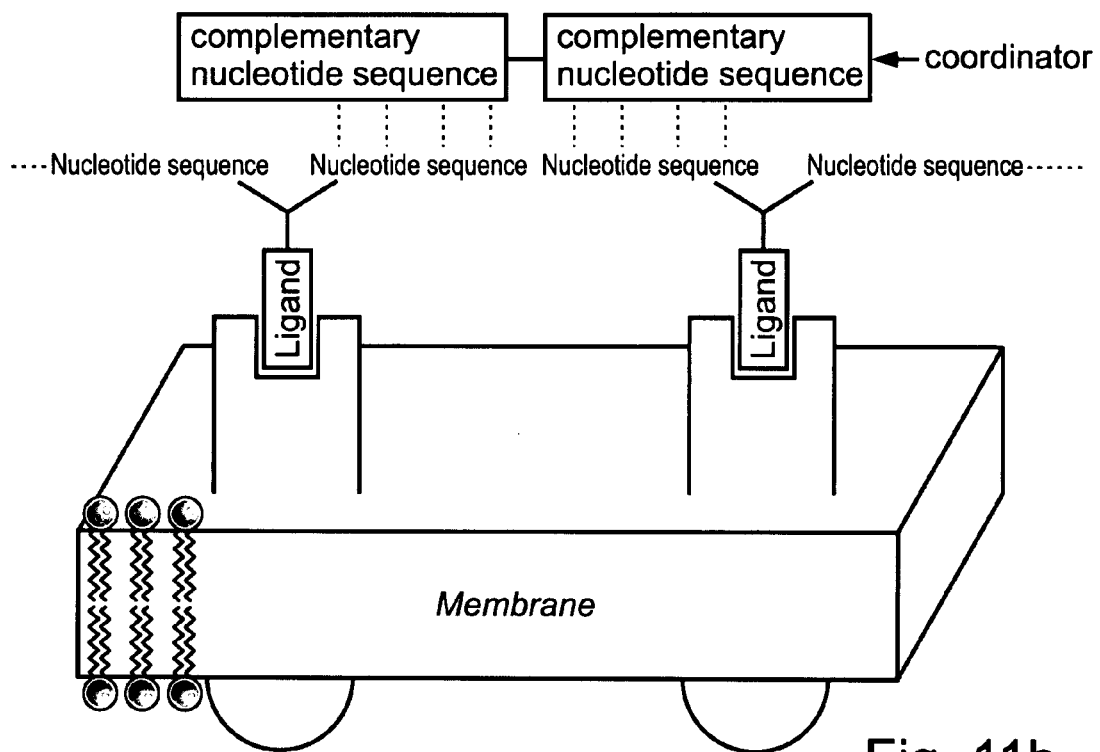
Figure 11C:
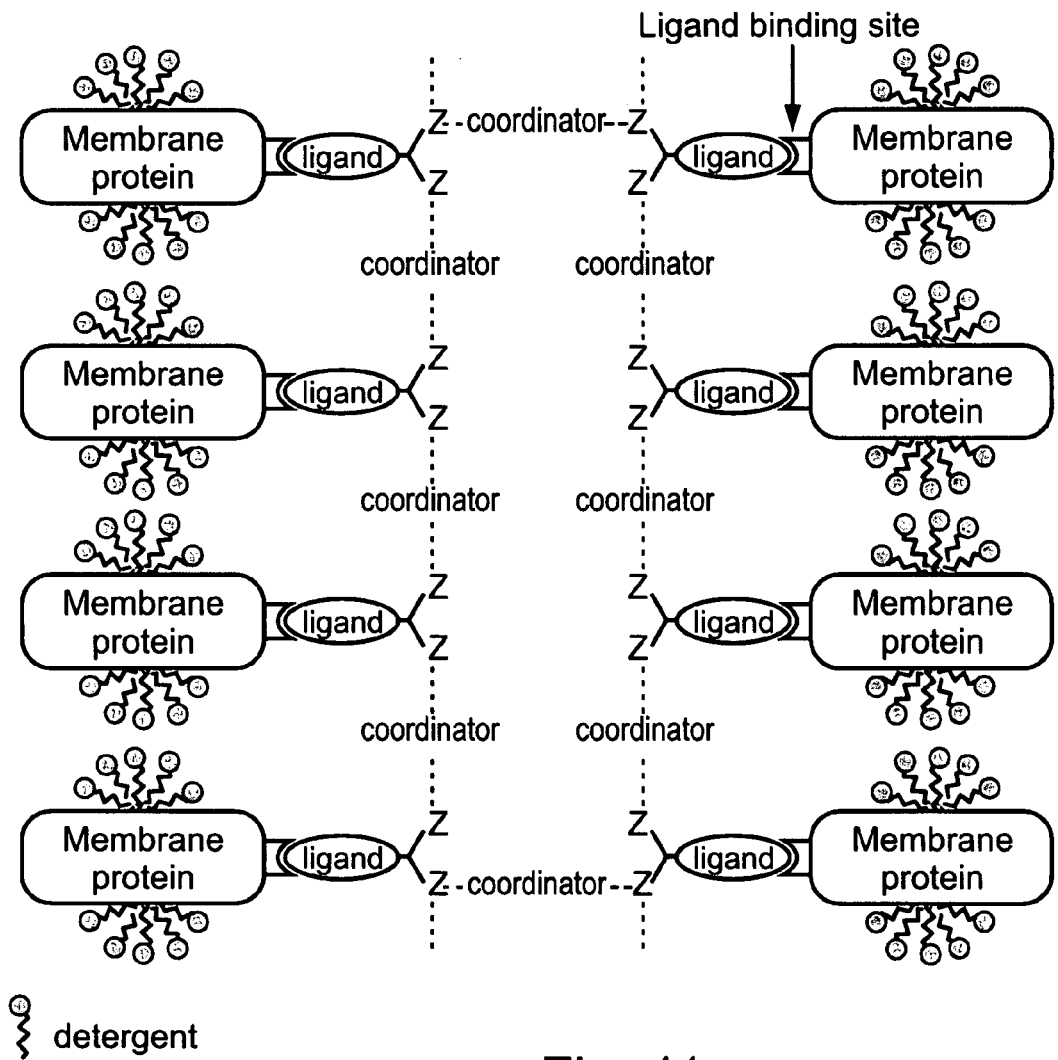
Figure 12:
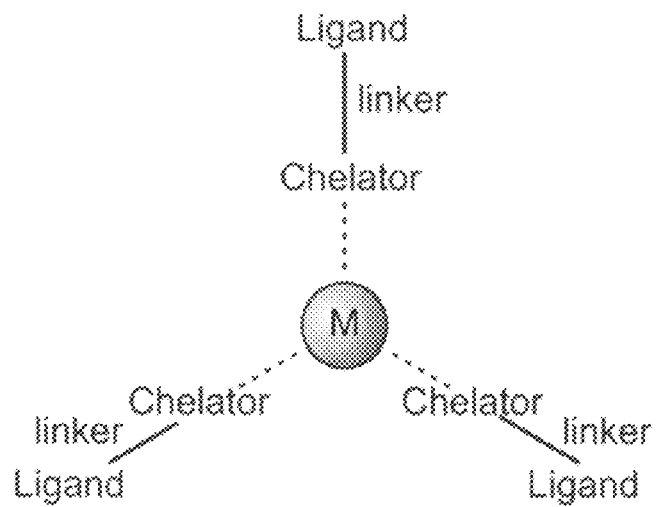
Figure 13A:
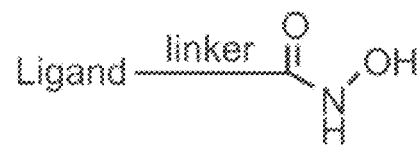
Figure 13B:
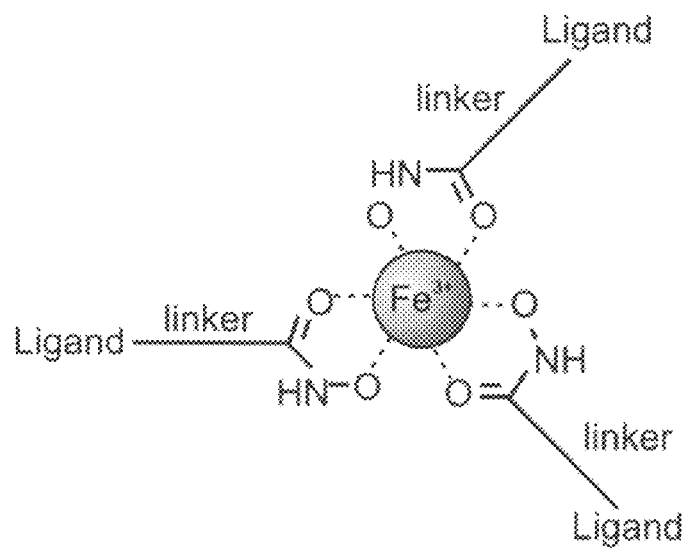
Figure 14:
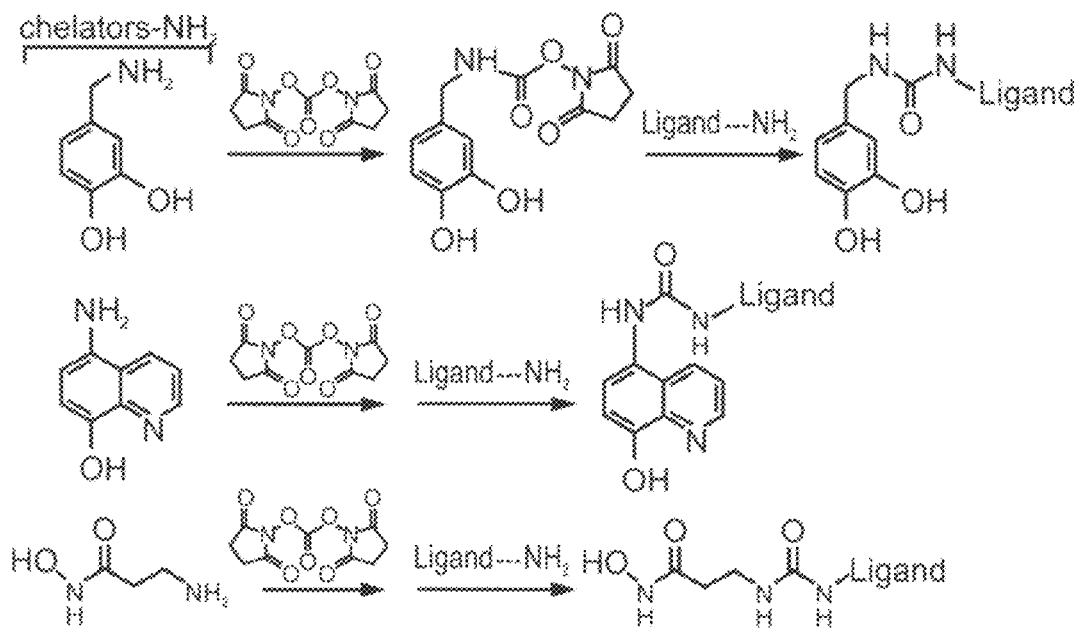
Figure 15A:
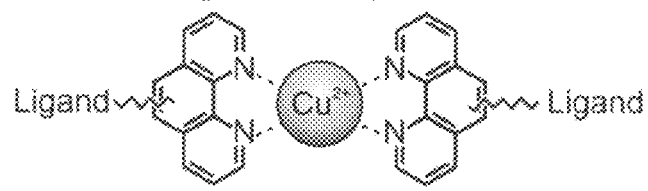
Figure 15B:
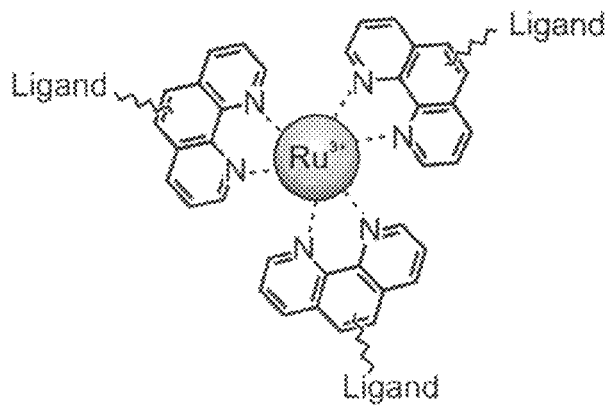
Figure 16A:
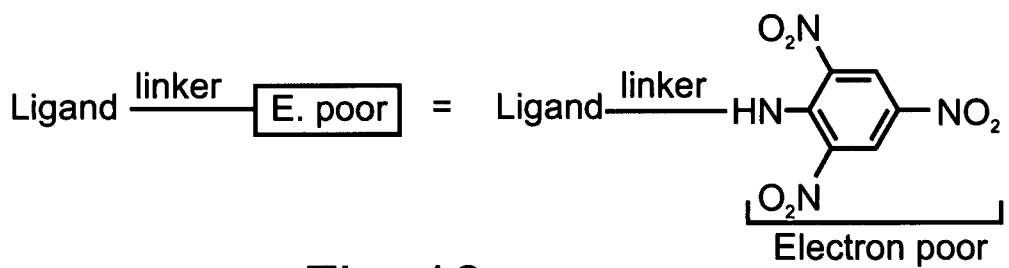
Figure 16B:
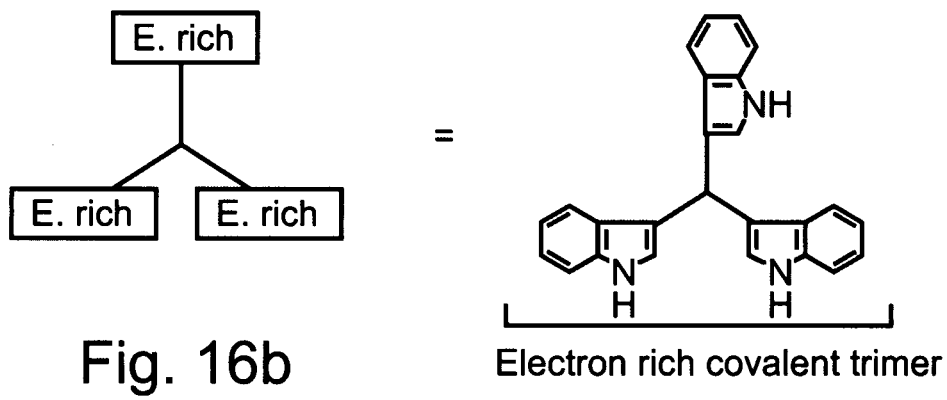
Figure 16C:
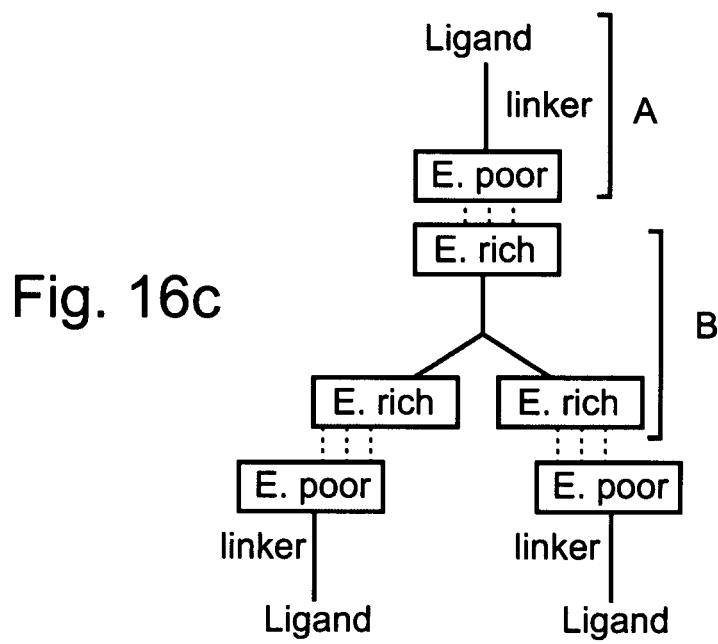
Figure 17:
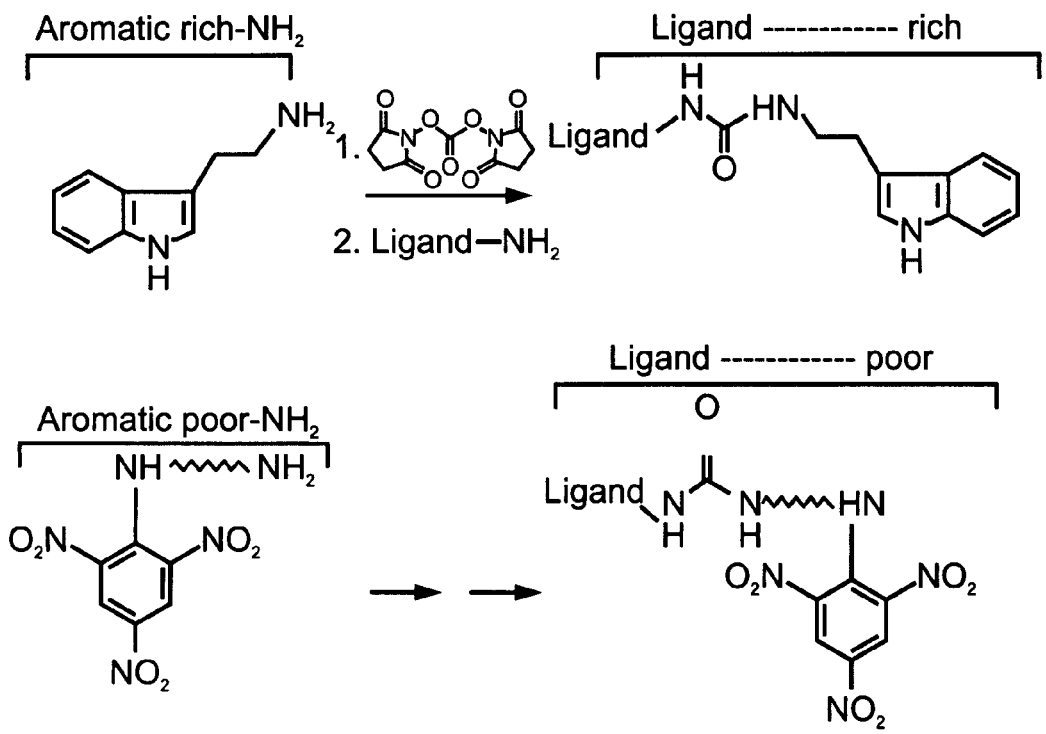
Figure 18:
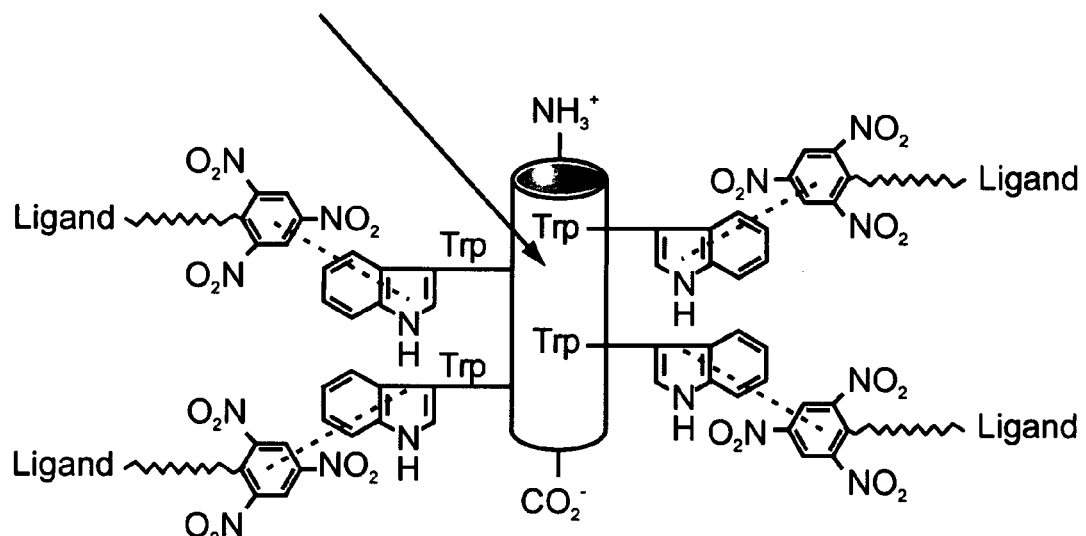
Figure 19:
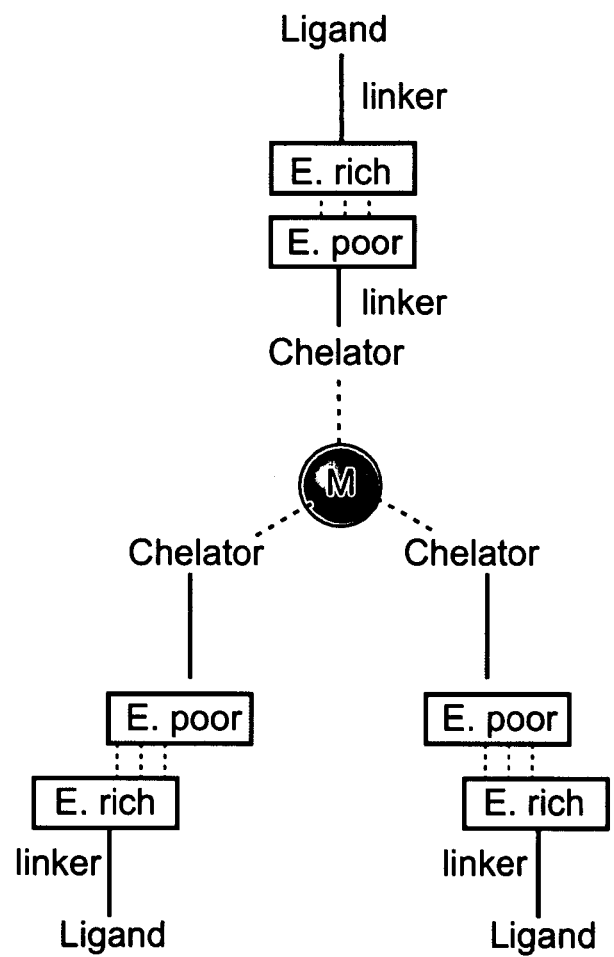
Figure 20:
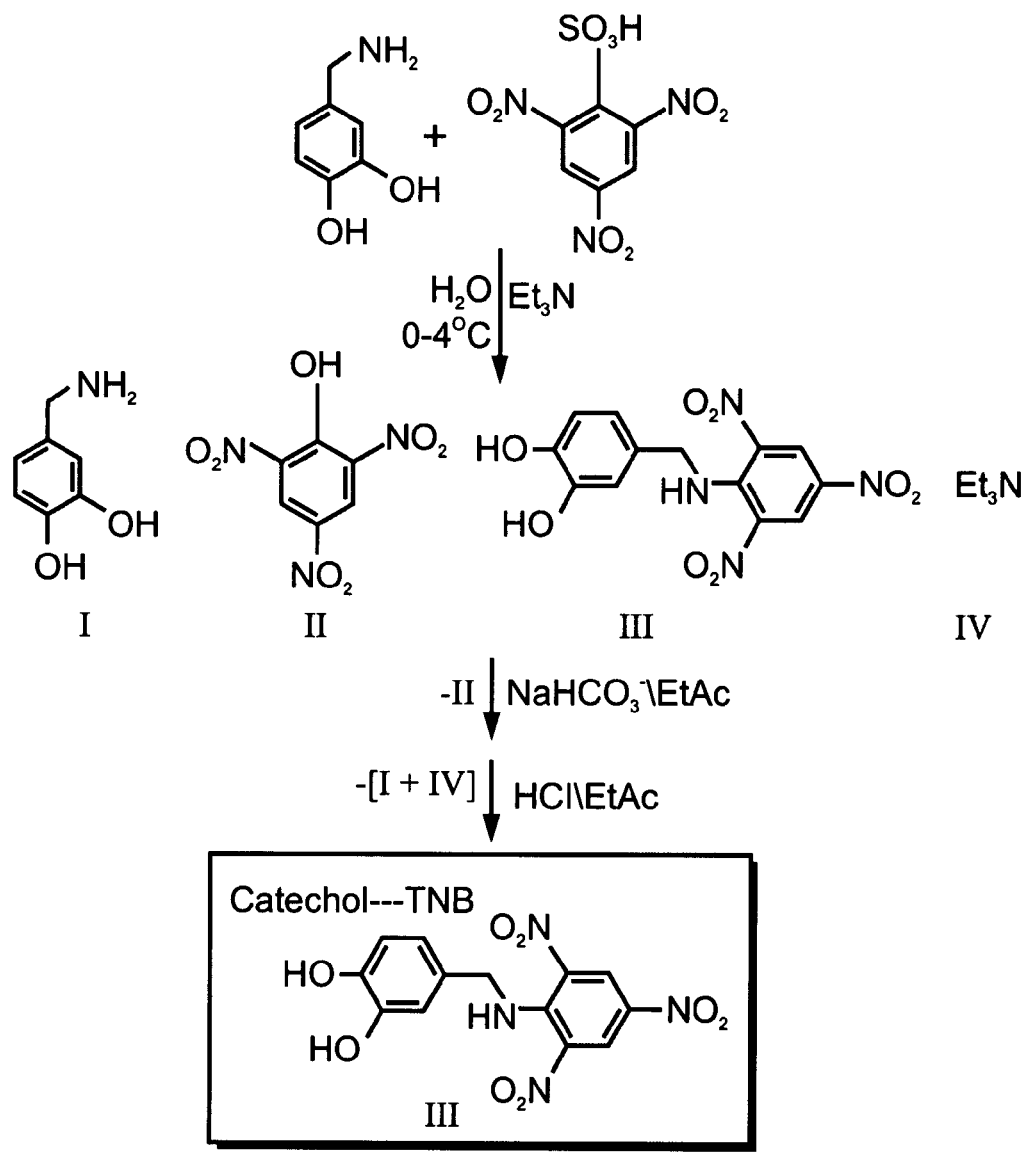
Figure 21A:
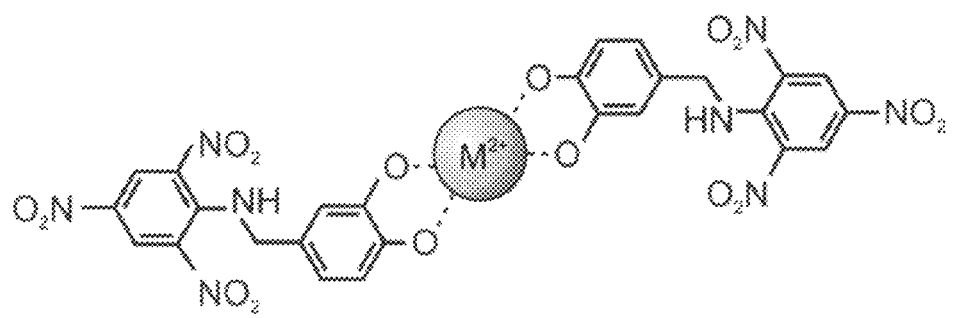
Figure 21B:
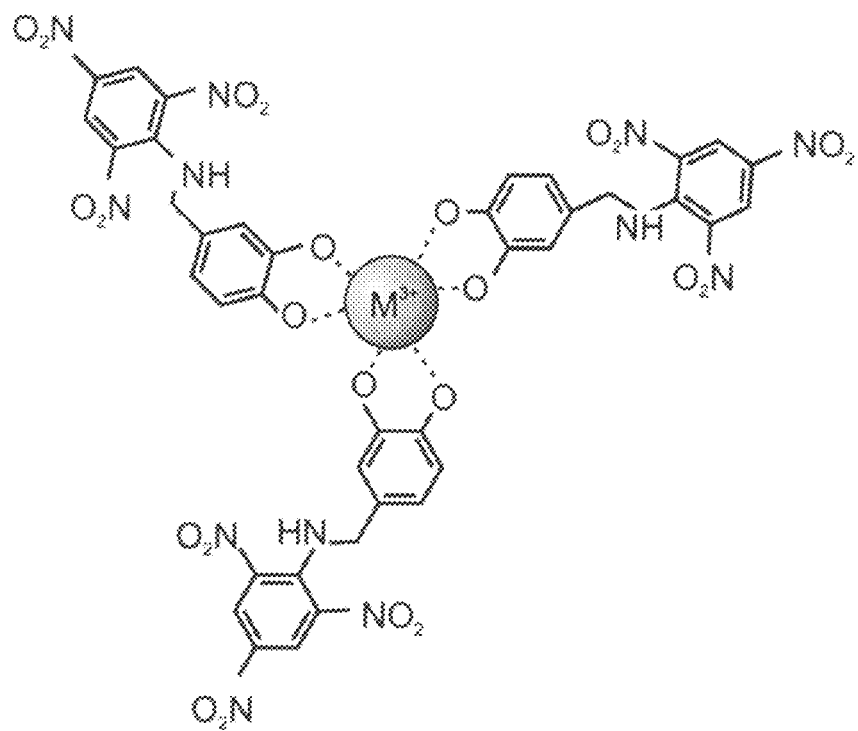
Figure 22A:
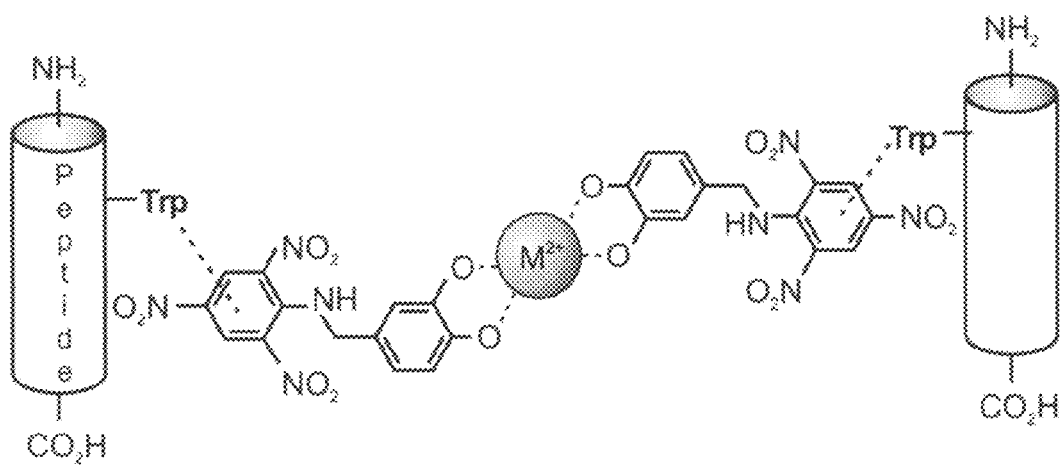
Figure 22B:
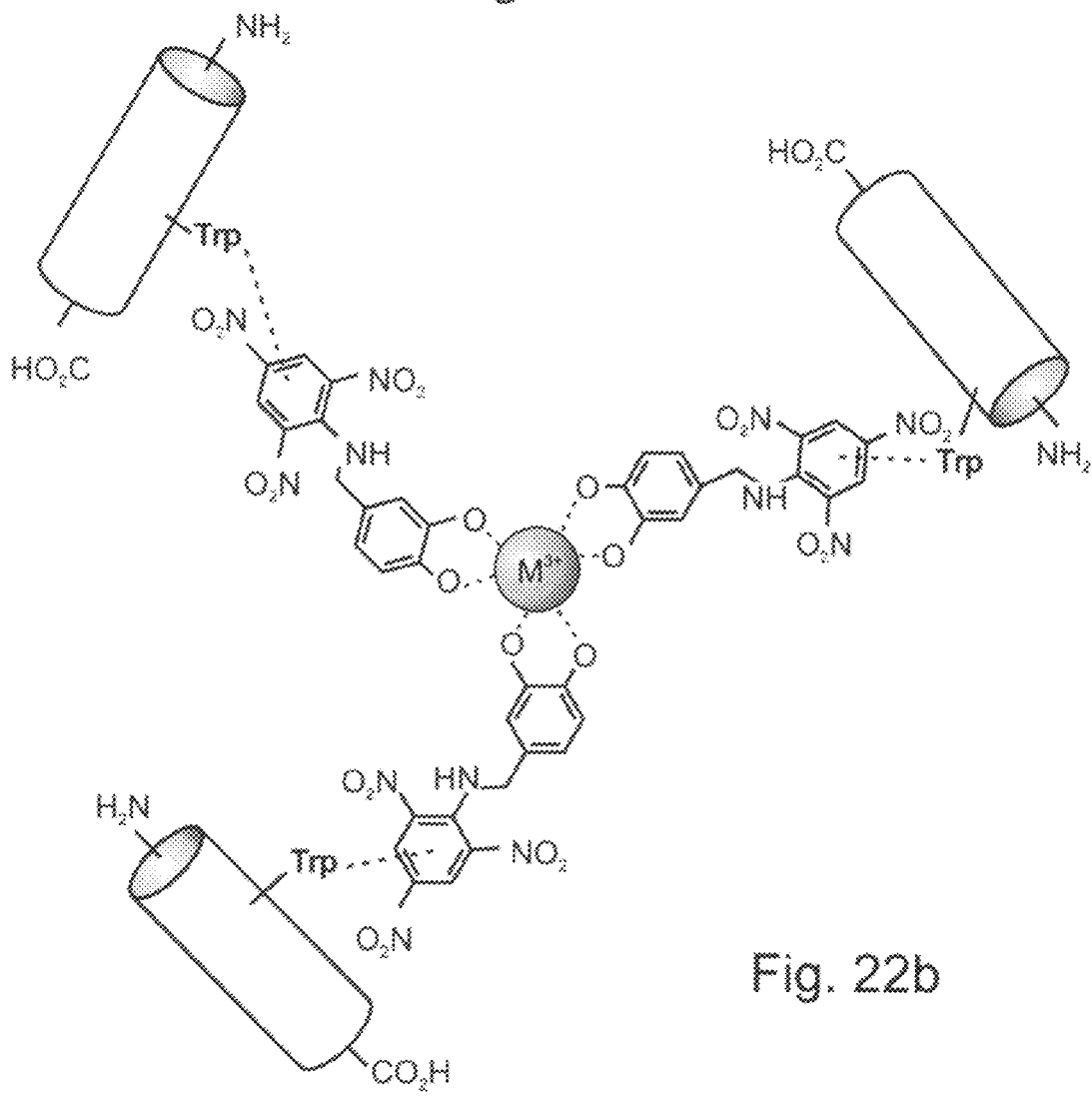
Figure 27A:
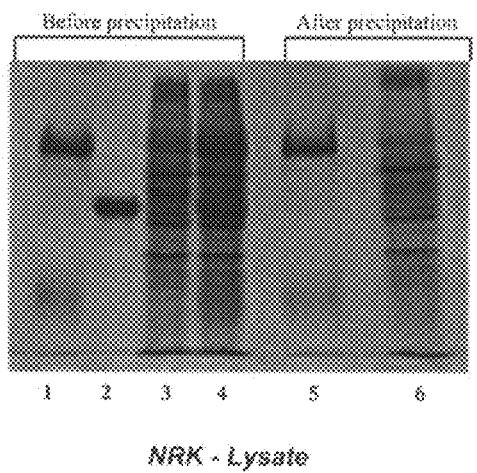
Figure 27B:
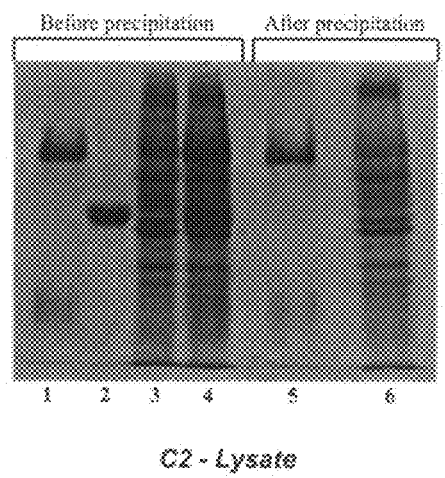
Figure 28:
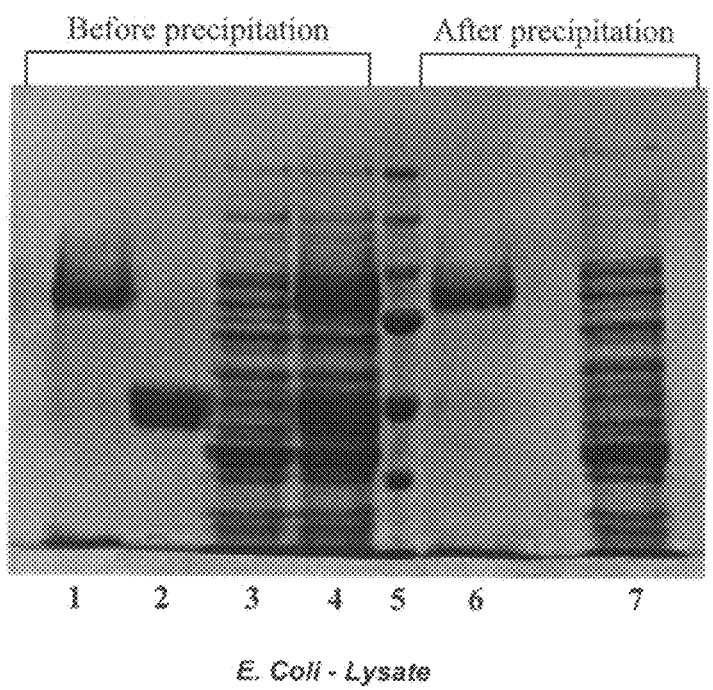
Figure 29A:
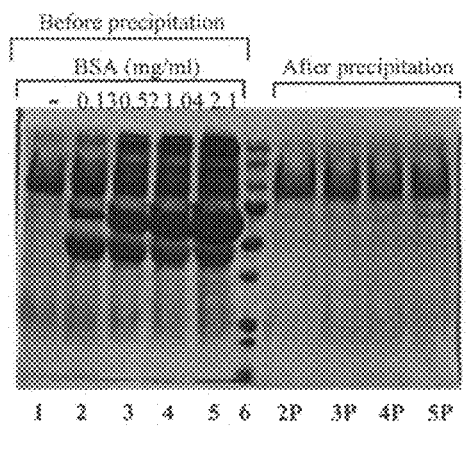
Figure 29B:
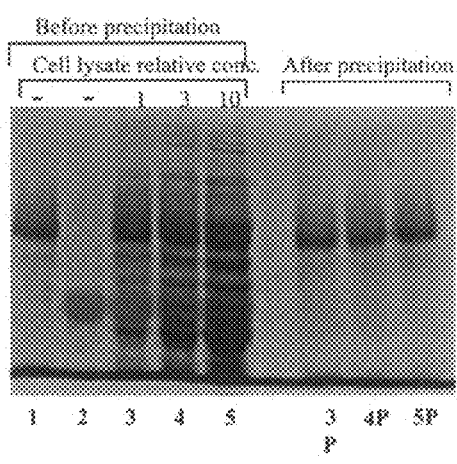
Figure 30A:
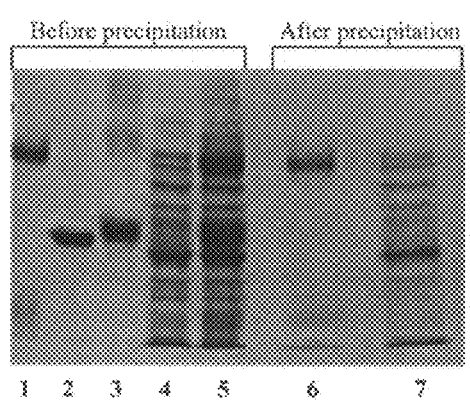
Figure 30B:
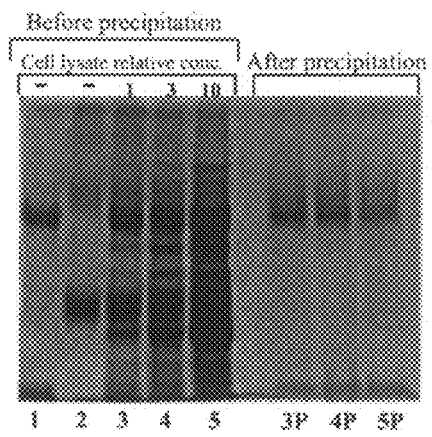
Figure 31A:
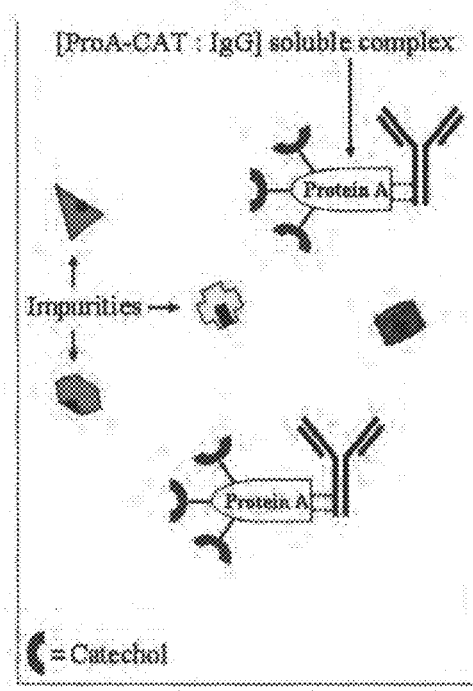
Figure 31B:
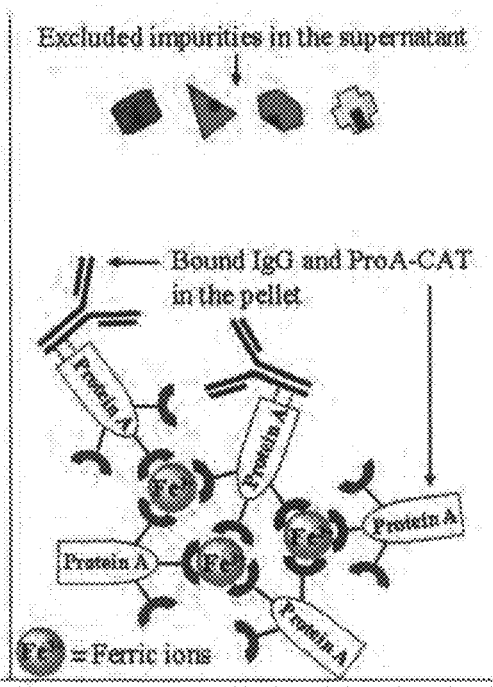
Figure 31C:
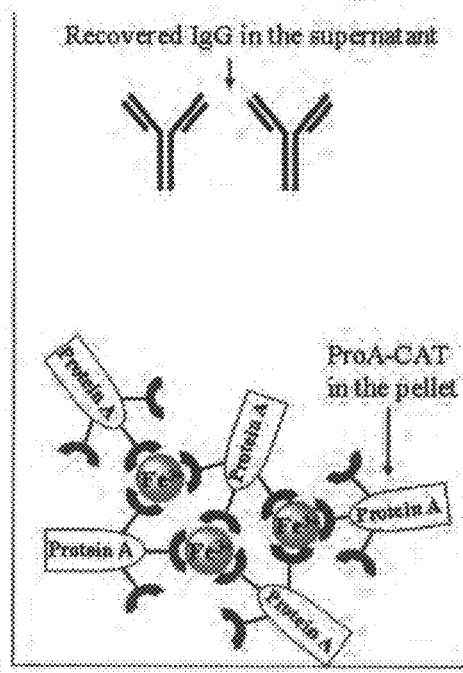
Figure 31D:
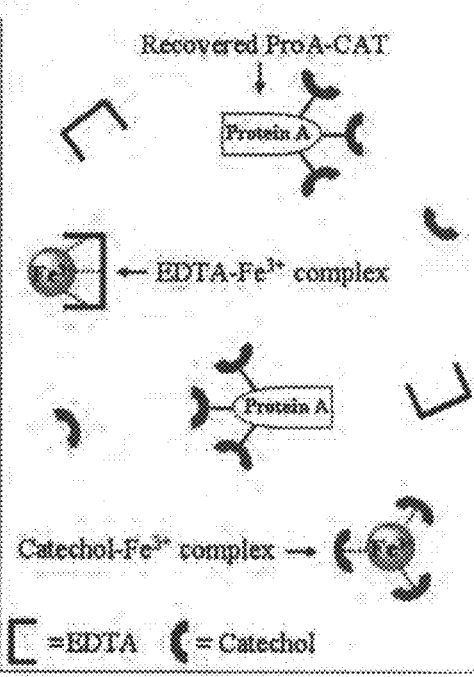
Figure 32A:
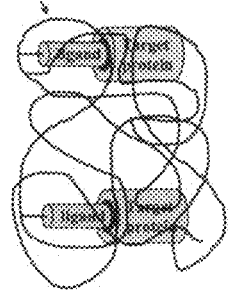
Figure 32B:
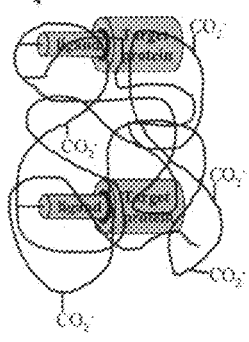
Figure 32C:
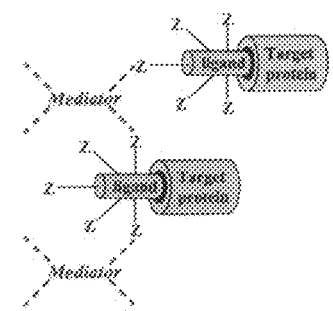
Figures 33A, 33B:
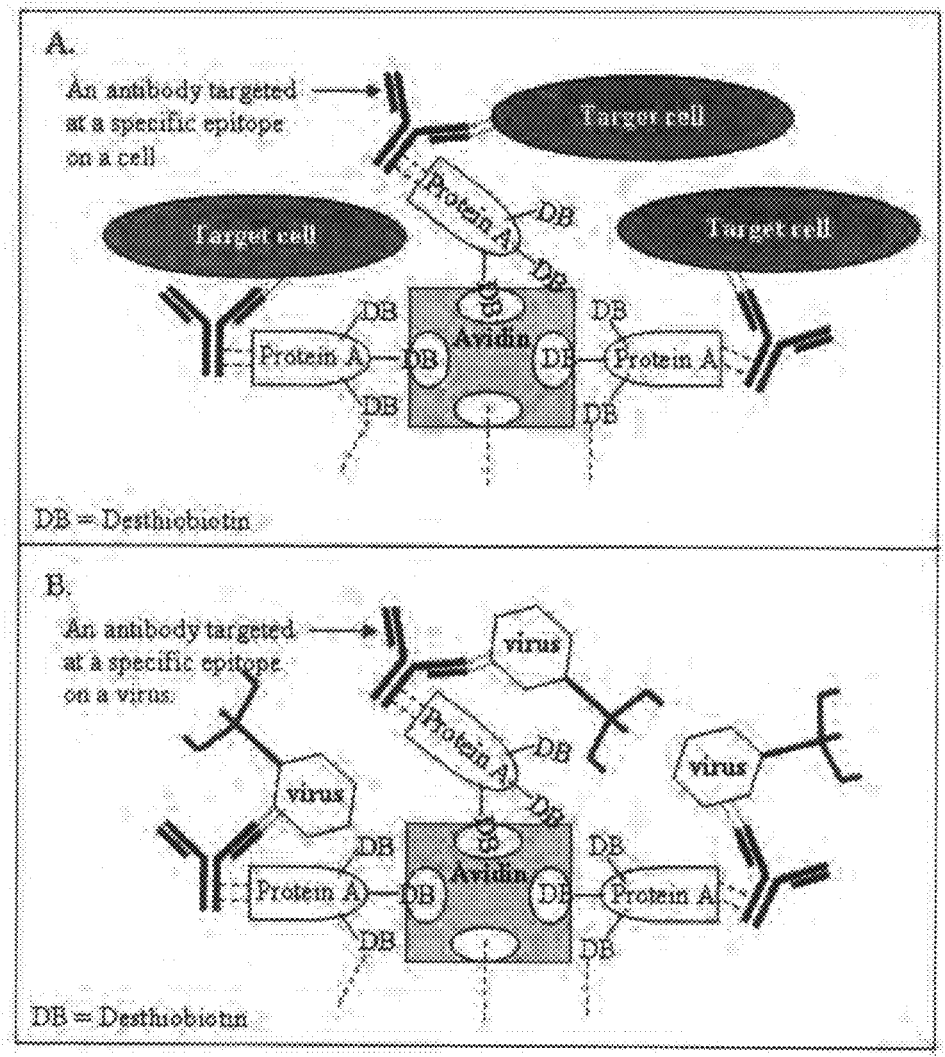
Figures 34A, 34B, 34C:
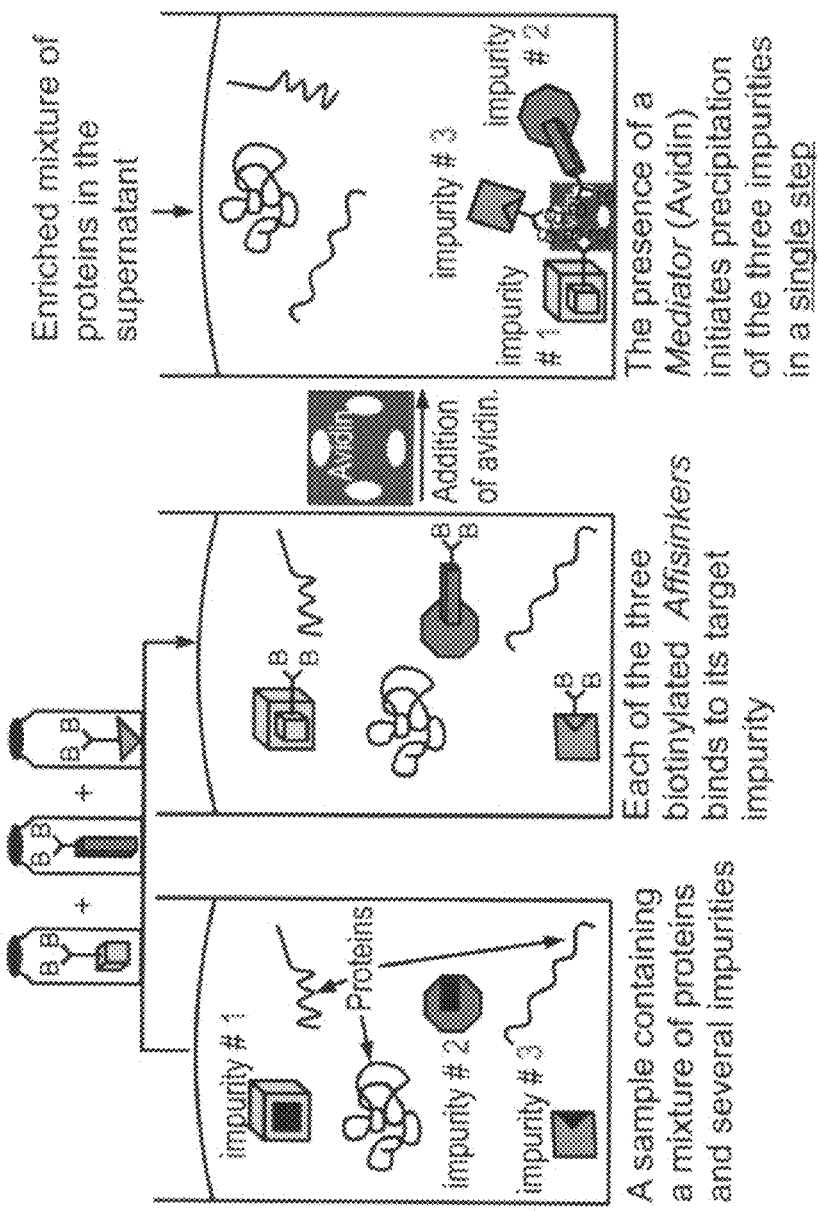
Figure 35:
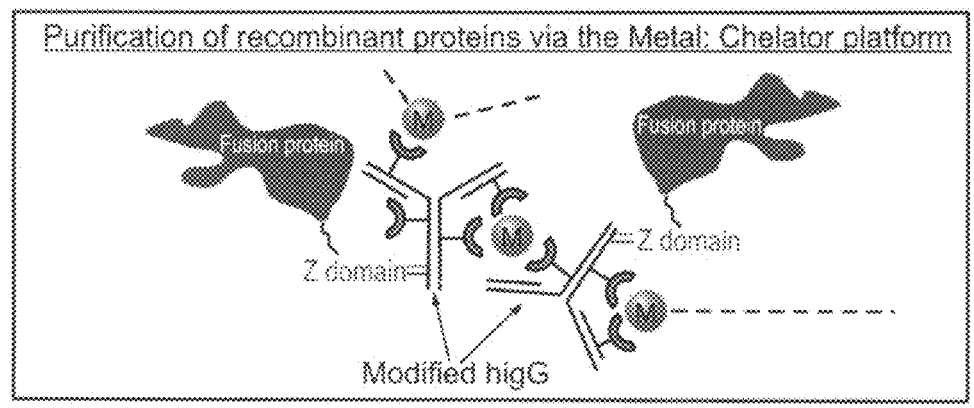
Figures 36A, 36B, 36C:
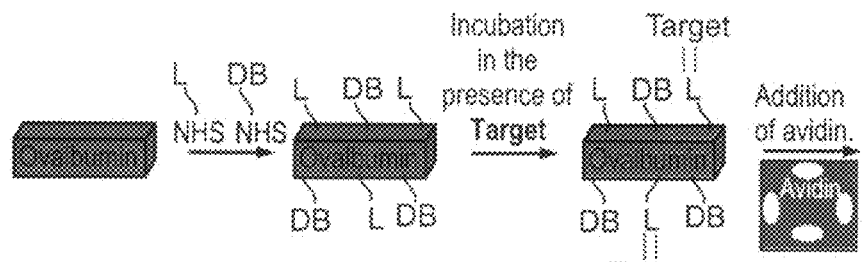
Figure 36D:
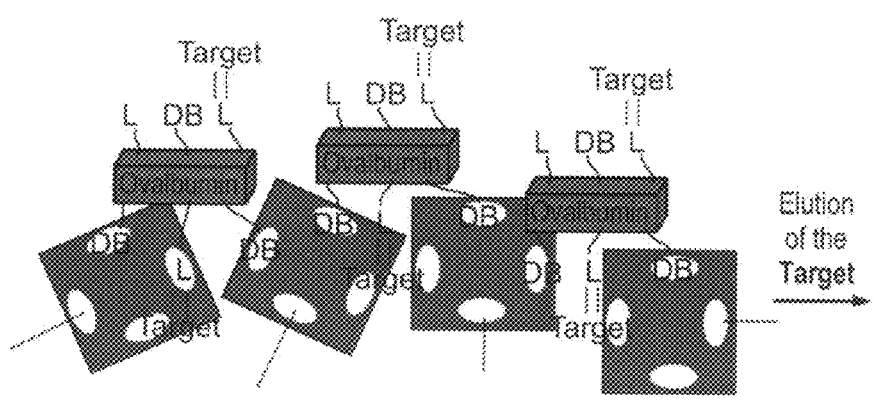
Figure 37:
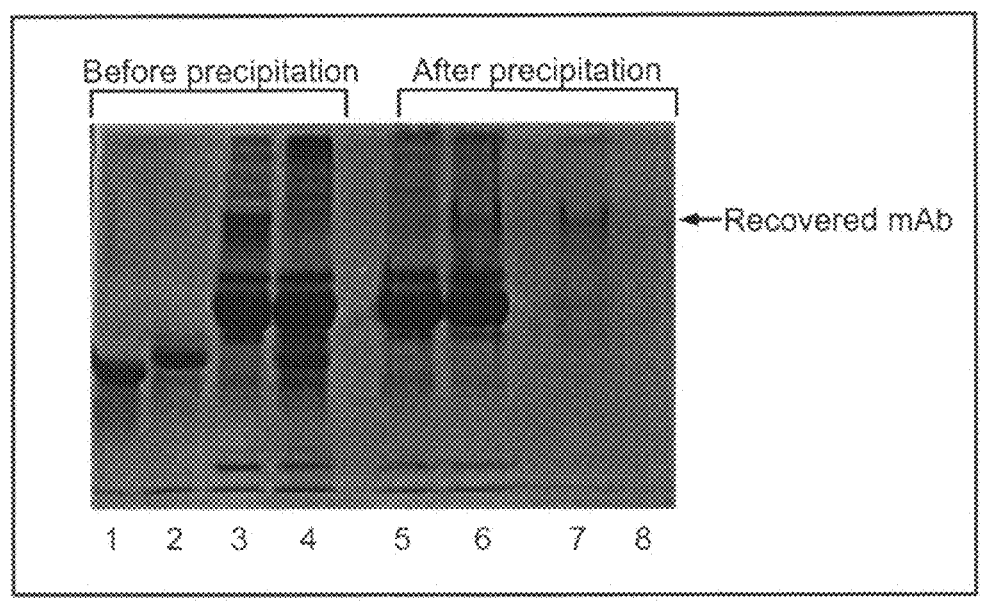

FIGS. 1a-f schematically illustrates several configurations of the compositions of the present invention. FIGS. 1a-c show ligands bound to two coordinating moieties. FIGS. 1d-f show ligands bound to multiple coordinating moieties. Z denotes the coordinating moiety;

FIGS. 2a-b schematically illustrates precipitation of a target molecule using the compositions of the present invention. A ligand covalently attached to a bis-chelator is incubated in the presence of a target molecule (FIG. 2a). Addition of a metal ($M^+$, $M^{2+}$, $M^{3+}$, $M^{4+}$) binds the chelator and forms a matrix including the target molecule non-covalently bound to the metal ion (FIG. 2b);

FIGS. 3a-e schematically illustrates stepwise recovery of the target molecule from the precipitate. FIG. 3a shows the addition of a free chelator, which competes with the binding of the ligand-bound chelator to the metal. FIG. 3b shows gravity-based separation of the ligand-bound target molecule from the free competing chelator and the complexed metal (FIG. 3c). FIG. 3d shows loading of the ligand-bound target molecule on an immobilized metal column to allow binding of the complex. Under proper elution conditions the target molecule is eluted while the ligand-coordinating moiety molecule is not. A desalting stage may be added for further purification of the target molecule. Regeneration of the ligand-chelator molecule is achieved by addition of a competing chelator to the column, followed by dialysis or ultrafiltration (FIG. 3e);

FIG. 4 schematically illustrates direct elution of the target molecule from the precipitate, wherein the chelator-metal complex is maintained, while binding between the target molecule and the ligand decreases;

FIG. 5 schematically illustrates regeneration of the precipitating unit (i.e., ligand-coordinating moiety) following elution of the target molecule. In this case, recovery is achieved by the addition of a competing chelator and application of an appropriate separation procedure, such as, dialysis and ultrafiltration;

FIGS. 6a-c schematically illustrates precipitation of a target molecule using nucleic acid sequences as the coordinating moiety. A ligand with a covalently bound bis-nucleotide sequence (coordinating moiety) is incubated in the presence of a target molecule (FIG. 6a). Addition of a complementary sequence results in the formation of matrix including ligand-coordinating moiety:target molecule:the complementary sequence (coordinator molecule, FIG. 6b). Non-symmetrical coordinating sequences are shown as well (FIG. 6c);

FIGS. 7a-b schematically illustrates precipitation of a target molecule using biotin as the coordinating moiety. A ligand with a covalently bound bis-biotin or biotin derivative such as: DSB-X Biotin is incubated in the presence of a target molecule (FIG. 7a). Introduction of avidin (or its derivatives) creates a network comprising ligand-coordinating moiety (biotin):target molecule:avidin (FIG. 7b);

FIGS. 8a-c schematically illustrates precipitation of a target molecule using electron rich molecules as the coordinating moiety. A ligand with a covalently bound bis-electron rich entity is incubated in the presence of a target molecule (FIG. 8a). Addition of a bis(also tris, tetra) electron poor derivative with the propensity to form a complex results in a non-covalent network comprising ligand-coordinating moiety (electron poor molecule):target molecule:bis-electron poor moiety (FIG. 8b). The picric acid and indole system can also be used according to the present invention (FIG. 8c);

FIG. 9 schematically illustrates precipitation of a target antibody with protein A (ProA) bound used as a ligand. Addition of an appropriate coordinator results-in a network of: Protein A—coordinating moiety:coordinator:target molecule;

FIGS. 10a-b schematically illustrates the use of the complexes of the present invention for crystallization of membrane proteins. The general formation of 2D (or 3D) structures in the presence of crystallizing composition is presented, where the coordinators are not interconnected between themselves (FIG. 10a). A more detailed example utilizing a specific ligand modified with two antigens, and a monoclonal antibody (mAb) directed at the specific antigen, serving as the coordinator, is illustrated in FIG. 10b;

FIGS. 11a-b schematically illustrates the use of metallo complexes (FIG. 11a) and nucleo-complexes (FIG. 11b) for the formation of crystals of membrane proteins;

FIG. 11c schematically illustrates a three-dimensional membrane complex using the compositions of the present invention. The hydrophobic domain of the protein is surrounded by detergent micelles. Z denotes a multi valent coordinator (i.e., at least bi-valent coordinator);

FIG. 12 schematically illustrates the formation of a non-covalent composition consisting of three ligands bound to a single metal coordinator, through suitable chelators which are bound to the ligands through covalent linkers;

FIGS. 13a-b schematically illustrate the modification of three ligands of interest to include the hydroxamate derivatives (FIG. 13a), such that a tri-non-covalent ligand complex is formed in the presence of $Fe^{3+}$ ions (FIG. 13b);

FIG. 14 schematically illustrates a two-step synthesis procedure for the generation of ligand-chelator molecules;

FIGS. 15a-b schematically illustrate the formation of di (FIG. 15a) and tri (FIG. 15b) non-covalent ligands, by utilizing the same ligand-linker-chelator molecule, while changing only, the cation present in the medium;

FIGS. 16a-c schematically illustrates the compositions of the present invention coordinated by electron poor/rich relations. By modifying a ligand with an electron poor moiety (FIG. 16a) and synthesizing a tri covalent electron rich moiety (FIG. 16b), a complex of the structure seen in FIG. 16c is formed;

FIG. 17 schematically illustrates a two step synthesis process for the preparation of ligand-electron rich or ligand-electron poor derivatives;

FIG. 18 schematically illustrates the use of peptides for the formation of ligand complexes utilizing electron rich and electron poor moieties;

FIG. 19 schematically illustrates the formation of ligand complexes which utilize a chelator-metal as well as electron rich and poor relationships;

FIG. 20 schematically illustrates a single step synthesis procedure for the preparation of a chelator-electron poor derivative;

FIGS. 21a-b schematically illustrates formation of di and tri non-covalent electron poor moieties by utilizing the same chelator-electron poor (catechol-TNB) derivative and changing only the cation in the medium;

FIGS. 22a-b schematically illustrates the addition of a peptide containing an electron rich moiety to form a dimer and a trimer;

FIGS. 23a-b schematically illustrates the formation of a polymer complex by the addition of a composition including ligand attached to two chelators which are coordinated through electron rich/poor relations;

FIG. 24 schematically illustrates one possibility of limiting the freedom of motion of non-covalent protein dimers. After non-covalent dimmers are formed via a ligand-linker-chelator with the addition of an appropriate metal, the addition of a covalent electron poor moiety [e.g. trinitrobenzene-trinitrobenzene (TNB-TNB)] leads to the simultaneous binding of two accessible electron rich residues (e.g. Trp) on two adjacent proteins thereby imposing motion constraints and allowing formation of a crystal structure;

FIG. 25 schematically illustrates chelators and metals, which can be used as the coordinating moiety and coordinator ion, respectively, in the compositions of the present invention;

FIG. 26 schematically illustrates electron rich and electron poor moieties which can be used as the coordinating moiety in the compositions of the present invention;

FIGS. 27a-b illustrate purification of rabbit IgG from normal rat kidney (NRK) cell lysate (FIG. 27a) or from mouse myoblasts (C2) cell lysate (FIG. 27b), utilizing Desthiobiotinylated protein A (DB-ProA) and free avidin. FIG. 27a—lane 1 rabbit IgG; lane 2 DB-ProA; lane 3 NRK cell lysate; lane 4 mixture of rabbit IgG, DB-ProA and NRK cell lysate; lane 5 recovered IgG (yield: ~90% by densitometry); lane 6 content of supernatant after specific precipitation of the IgG from the cell lysate. FIG. 27b—lane 1 rabbit IgG; lane 2 DB-ProA; lane 3 C2 cell lysate; lane 4 mixture of rabbit IgG, DB-ProA and C2 cell lysate; lane 5 recovered IgG (yield: ~90% by densitometry); lane 6 content of supernatant after specific precipitation of the IgG from the cell lysate;

FIG. 28 illustrates purification of rabbit IgG from E. coli cell lysate, utilizing desthiobiotinylated protein A (DB-ProA) and free avidin. Lane 1 rabbit IgG; lane 2 DB-ProA; lane 3 E. coli cell lysate; lane 4 mixture of rabbit IgG, DB-ProA and E. coli cell lysate; lane 5 Biorad prestained protein markers; lane 6 recovered IgG (yield: 85% by densitometry); lane 7 content of supernatant after specific precipitation of the IgG from the cell lysate;

FIG. 29a illustrates the effect of increase background contamination (BSA) on the precipitation process. Lane 1 rabbit IgG; lanes 2-5 constant concentration of rabbit IgG and DB-ProA in the presence of increase BSA concentration; Lane 6 Biorad prestained protein standards; lanes 2P-5P recovered IgG from pellets generated in lanes 2-5 respectively (yield: 80-85% by densitometry);

FIG. 29b illustrates the effect of increase background contamination (E. coli lysate) on the precipitation process. Lane 1 rabbit IgG; lane 2 DB-ProA; lanes 3-5 constant concentration of rabbit IgG and DB-ProA in the presence of increased E. coli cell lysate concentrations; lanes 3P-5P recovered IgG from pellets generated in lanes 3-5, respectively (yield: 80-85% by densitometry);

FIG. 30a illustrates purification of rabbit IgG from E. coli cell lysate utilizing Protein A modified with the strong chelator catechol (ProA-CAT) and $Fe^{3+}$ ions. Lane 1 rabbit IgG; lane 2 native Protein A; lane 3 ProA-CAT; lane 4 E. coli cell lysate; lane 5 rabbit IgG, ProA-CAT and E. coli cell lysate; lane 6 recovered rabbit IgG; lane 7 content of supernatant after addition of $Fe^{3+}$ ions to the mixture in lane 5;

FIG. 30b illustrates the effect of increased background contamination on the precipitation process. Lane 1 rabbit IgG; lane 2 ProA-CAT; lanes 3-5 constant concentration of rabbit IgG and ProA-CAT in the presence of increased E. coli lysate concentrations; lanes 3P-5P recovered IgG from pellets generated in lanes 3-5, respectively;

FIGS. 31a-d illustrate antibody purification utilizing a modified Protein A (ProA-CAT) and $Fe^{3+}$ ions. FIG. 31a—specific binding of ProA-CAT to the target IgG leads to the formation of the: [ProA-CAT:target IgG] soluble complex. FIG. 31b—addition of $Fe^{3+}$ ions to the complex shown in FIG. 31a generates insoluble macro-complexes containing the target IgG. Impurities, left in the supernatant are discarded via centrifugation. FIG. 31c—target IgG is eluted under acidic conditions without dissociating the [ProA-CAT:$Fe^{3+}$] macro-complex of the insoluble pellet. FIG. 31d—Regeneration of ProA-CAT in the presence of strong metal chelators which compete for the complexed $Fe^{3+}$ ions thereby dissociating the macro-complex (i.e., pellet). The complexed $Fe^{3+}$ ions and free chelators are excluded by dialysis while the free ProA-CAT can be reused;

FIGS. 32a-c illustrate a comparison of the basic chemical architecture of affinity chromatography (AC), affinity precipitation (AP) and affinity sinking (AS). FIG. 32a—Ligands in AC are immobilized to non-soluble polymeric matrixes. FIG. 32b—Ligands in AP are immobilized to water soluble polymers which would change reversibly to water in-soluble upon a physiochemical change such as low pH. FIG. 32c—Ligands in AS are not immobilized but modified with a complexing entity enabling their precipitation upon addition of an appropriate Mediator. Thus, no polymeric entity is present within the precipitation process and ligands are free in the medium;

FIGS. 33a-b schematically illustrate positive or negative cell selection (FIG. 33a) and virus depletion (FIG. 33b), utilizing a core complex comprised of [DB-ProA-avidin];

FIG. 34 illustrates simultaneous depletion of several impurities upon addition of different biotinylated ligands and free avidin. The resulting supernatant in stage C. contains enriched mixture of target proteins whereas impurities are left insoluble in the pellet;

FIG. 35 illustrates purification of fusion proteins with a modified human IgG (hIgG) and an appropriate transition metal;

FIG. 36 illustrates covalent modification of a protein (e.g. Ovalbumin) with a small ligand (e.g. peptide) and a complexing entity (e.g. desthiobiotin) would lead to a modified protein (b) possessing multi-complexing features. Its incubation in a medium containing a Target would lead to specific binding of the Target (c) and precipitation of the latter complex upon addition of free Avidin (d). Thus, the Target is specifically precipitated whereas impurities are left soluble in the supernatant and are excluded. Elution of the Target is obtained by incubating the above macro-complex under conditions favoring dissociation of the [Ovalbumin-Ligand:Target] complex while maintaining the: [Ovalbumin-Desthiobiotin:avidin] complex, intact;

FIG. 37 illustrates purification of an Anti-FITC mAb utilizing modified ovalbumin and free avidin. Lane 1—native ovalbumin; lane 2—modified ovalbumin; lane 3—mAb Anti-FITC; lane 4—mixture the mAb and the modified ovalbumin; lane 5—content of supernatant after addition of avidin to lane 4 in the absence of free Fluorescein; lane 6—content of supernatant after addition of avidin to lane 4 in the presence of Fluorescein; lane 7—recovered mAb from the pellet generated in the absence of free Fluorescein; lane 8—recovered mAb from the pellet generated in the presence of free Fluorescein;

FIG. 38 illustrates Purification of His-Tag-Target utilizing non-immobilized Ovalbumin-NTA-Desthiobioitin multi-ligand. Modification of a protein (e.g. Ovalbumin) with a metal chelator (e.g. NTA) and desthiobiotin generates the non-immobilized modified ligand (b). Incubation of the above under proper conditions (e.g. low imidazole concentration); an appropriate metal (e.g. Ni2+, Co2+) and a medium containing the His-Tag-Target will lead to specific binding (c). Addition of free avidin will generate insoluble macro-complexes that will precipitate together with the His-Tag-Target (d). Elution of the His-Tag-Target could then be performed leaving the: [modified ovalbumin:avidin] macro-complex in the pellet; and FIG. 39 illustrates gel chromatography of a precipitate obtained from a regular network and defective network.

Figure 40A:
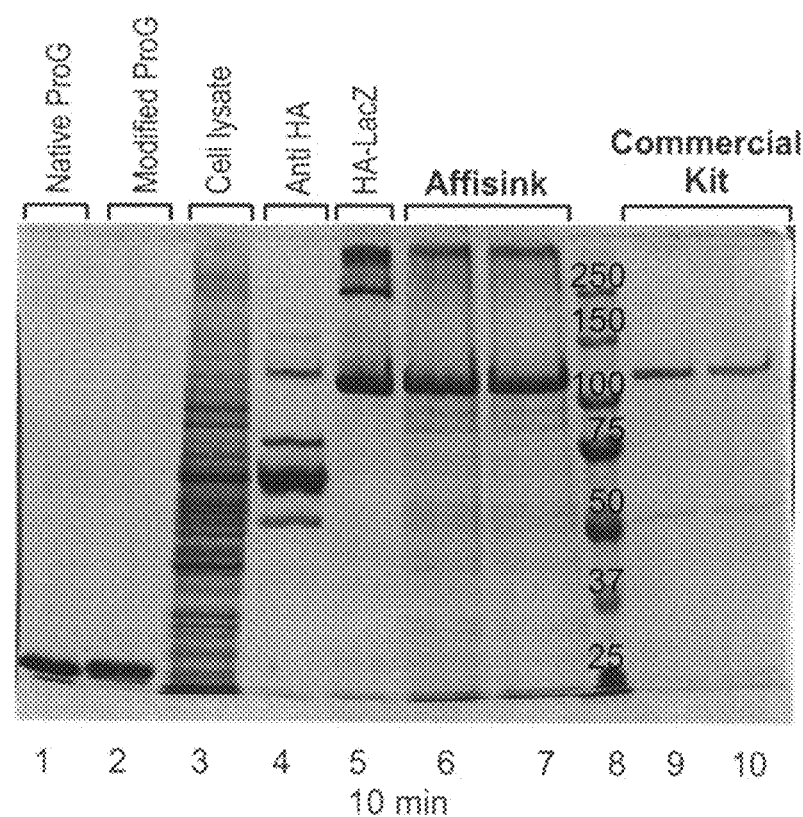
Figure 40B:
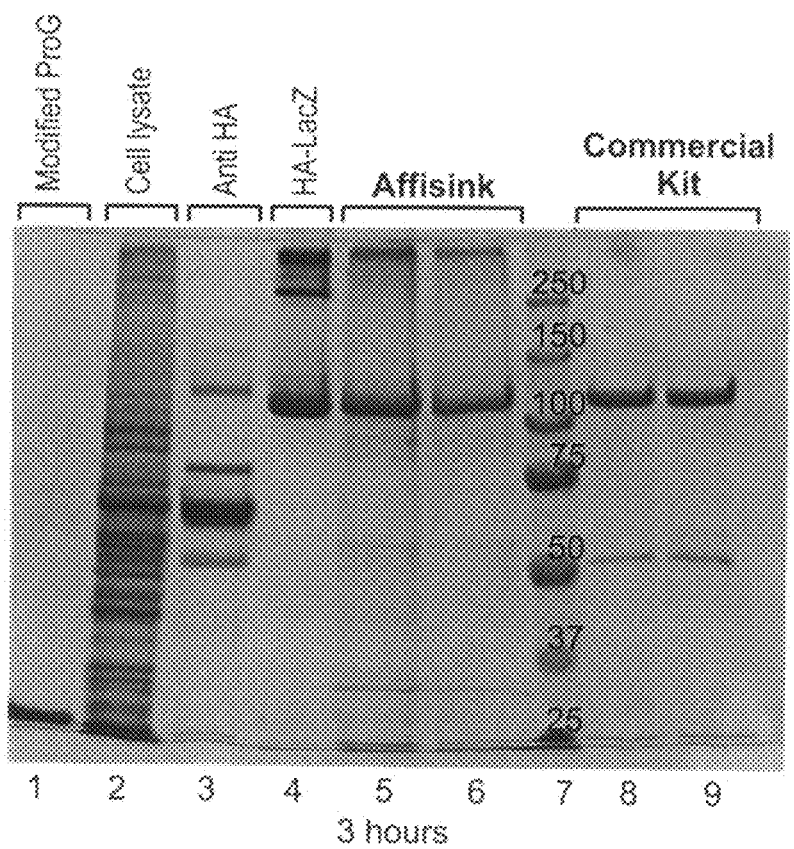

FIGS. 40a-b are pictures showing precipitation of immuno-labeled antigen using desthiobiotinylated-Protein-G. FIG. 40a shows immunoprecipitation of HA-LacZ from normal rat kidney (NRK) lysate. Time of incubation: 10 minutes. Lane 1 native Protein G; lane 2 desthiobiotinylated Protein (DB-ProG); lane 3 NRK cell lysate; lane 4 anti-HA mAb (Sigma Cat. No. H9658); lane 5 purified target HA-LacZ; lanes 6-7 recovered HA-LacZ under conditions described in Example 8 (yield: 95-100% by densitometry); lane 8 Biorad prestained protein markers; lanes 9-10 recovered HA-LacZ utilizing the Sigma Protein G Immunoprecipitation Kit Cat # IP-50 (yield: ~15-20% by densitometry). FIG. 40b shows as described in FIG. 40a only after 3 hours of incubation. Lanes 5-6 recovered HA-LacZ under conditions described in Example 8 (yield: 90% and 75%); lanes 8-9 commercial Kit recovered HA-LacZ (yield: 71-75%).

FIGS. 41A-D schematically show the stepwise selection of cells according to the teachings of the present invention.

FIGS. 41E-H show depletion of Jurkat-GFP cells from a mixture with K-562 cells. FIGS. 41E-F—when no specific antibody is present during the precipitation process the ratio between the two cell populations does not change significantly (not shown) and the supernatant is not enriched with K-562 cells as determined by fluorescence (E) or granulation (F). However as shown in FIGS. 41G-H, in the presence of two specific mAb's: anti-CD3, anti-CD28, directed at two epitopes on Jurkat-GFP cells the supernatant is enriched with the K-562 populations as determined by fluorescence (G) or granulation (H).

FIGS. 42A-B shows the formation of macroaggregates (which do not comprise cells) and their dissolution using biotin. FIG. 42A—Inverted light microscope pictures indicate the presence of high molecular weight aggregates present in the medium after the addition of streptavidin (i.e. after the precipitation step). The arrows are pointing to a representative aggregate. FIG. 42B—A short incubation of the medium (e.g., 1 min.) in the presence of biotin (e.g., 1 mM) lead to quantitative dissolution of the observed aggregates.

Figure 43A:
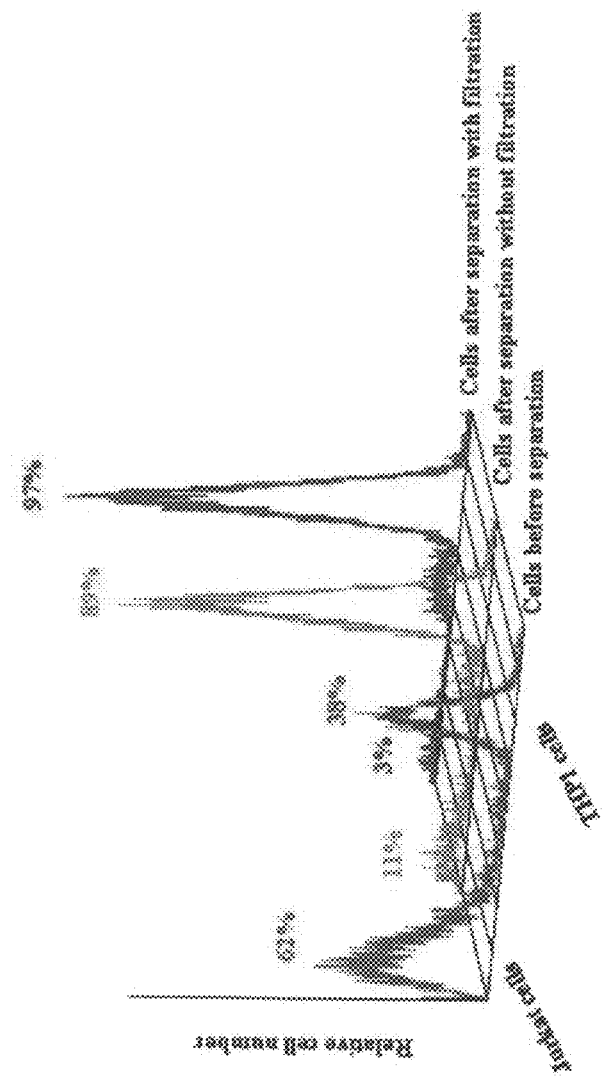

FIG. 43A shows the effect of filtration on the purity of enriched THP1 cells. THP1 cells were modified with FITC and mixed with Jurkat cells. Jurkat cells were depleted according to the protocol described in the Experimental and the supernatant devoid the precipitate was analyzed by FACS. Greater purity of THP1 cells is observed when the supernatant is filtered (i.e., 89% vs. 97%). It should be noted that more than a single filtration step may be required, or that the use of several filters with different pore size may lead to better performance.

Figure 43B:
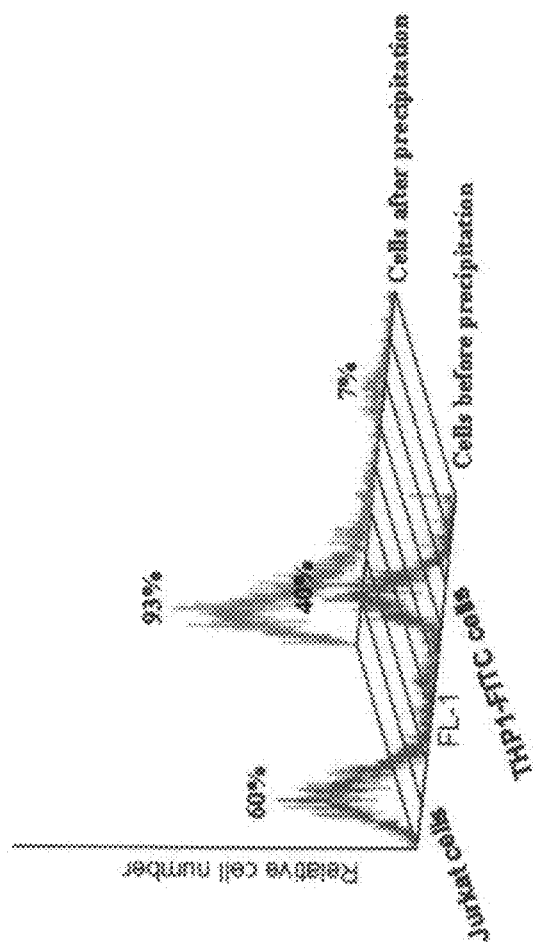

FIG. 43B shows positive selection of Jurkat cells from THP1-FITC cells. THP1 cells were modified with FITC and mixed with Jurkat cells. Jurkat cells were positively selected from their mixture with the labeled THP1-FITC cells using a cocktail of two mAb's (anti-CD3 and anti-CD-28). The FACS analysis of the dissolved precipitate, shows that the precipitate contains primarily Jurkat cells (Jurkat, 93%).

Figure 44:
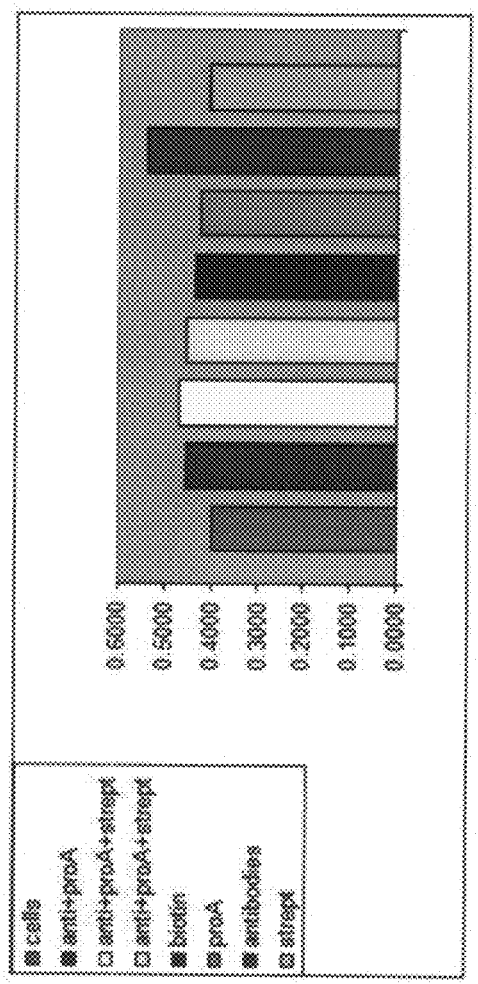

FIG. 44 is a bar graph showing the effect of different reagents used for cell purification/depletion on cell viability as determined by an XTT assay.

Figure 45:
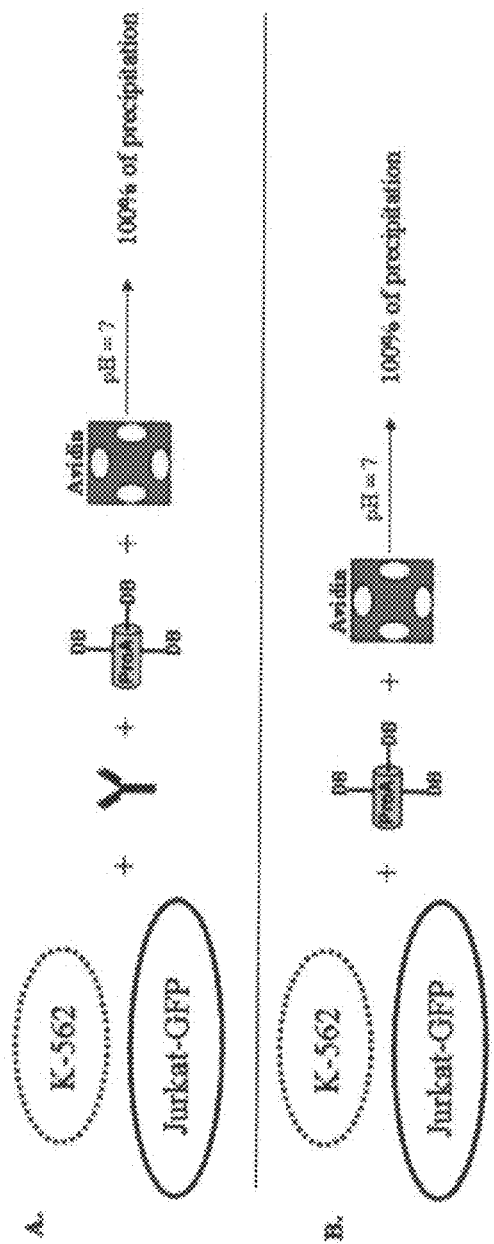

FIG. 45 is a scheme showing non-specific cell precipitation using avidin.

Figure 46:
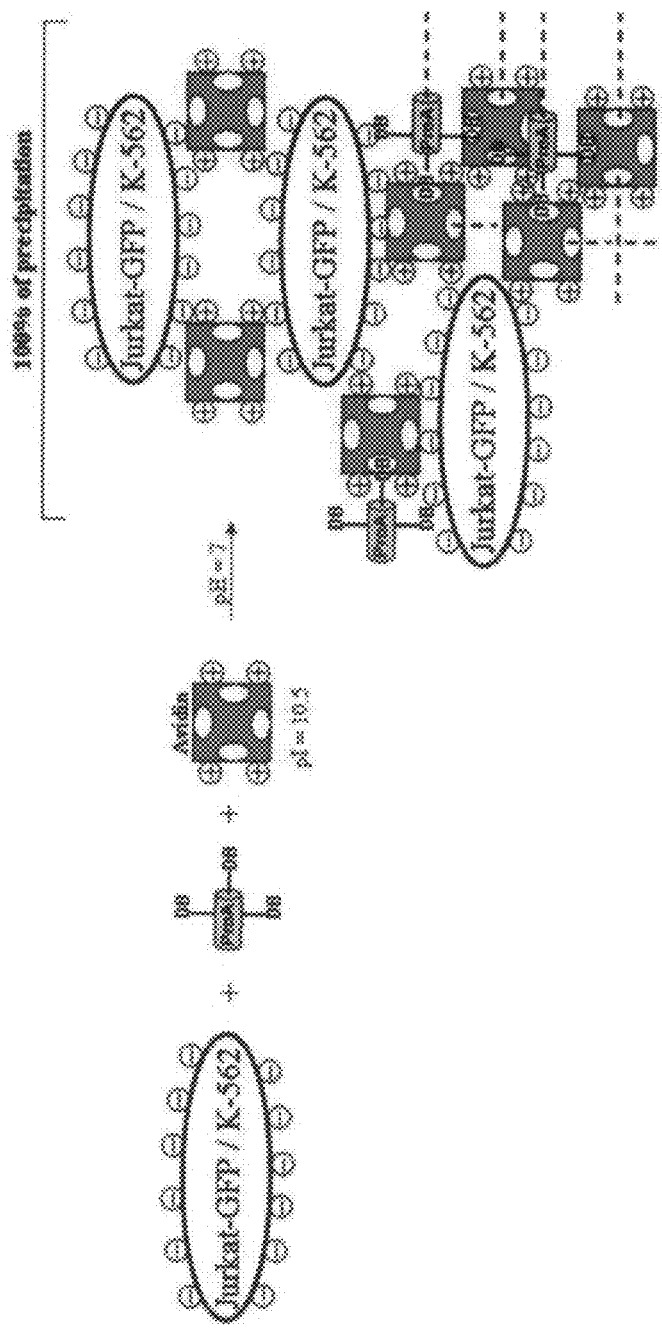

FIG. 46 is a scheme showing electrostatic interactions which contribute to the non-specific cell precipitation shown in FIG. 45.

Figure 47:
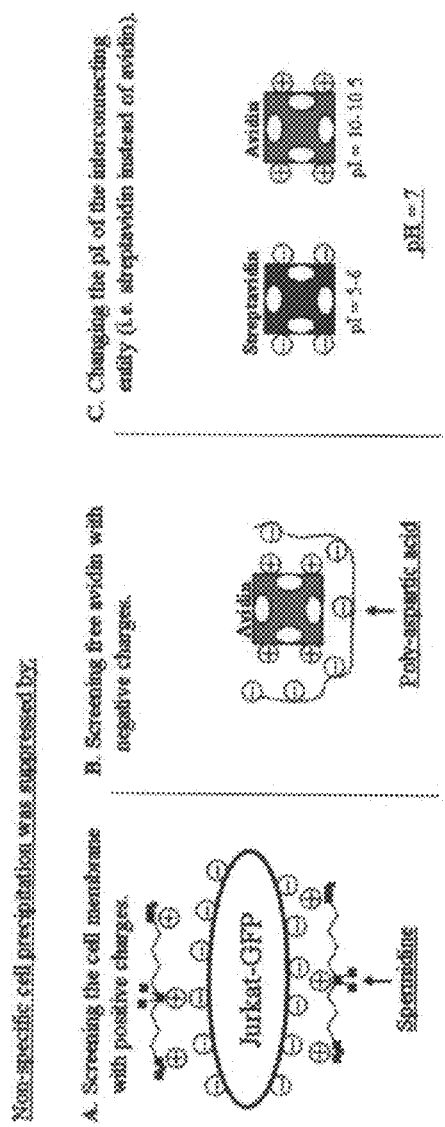

FIGS. 47A-C is a scheme showing the ability to reduce non-specific cell precipitation by modulation of electrostatic interactions through masking negative charge on the cell membrane (FIG. 47A), masking positive charge on avidin (FIG. 47B) or use of sterptavidin (FIG. 47C).

Figure 48:
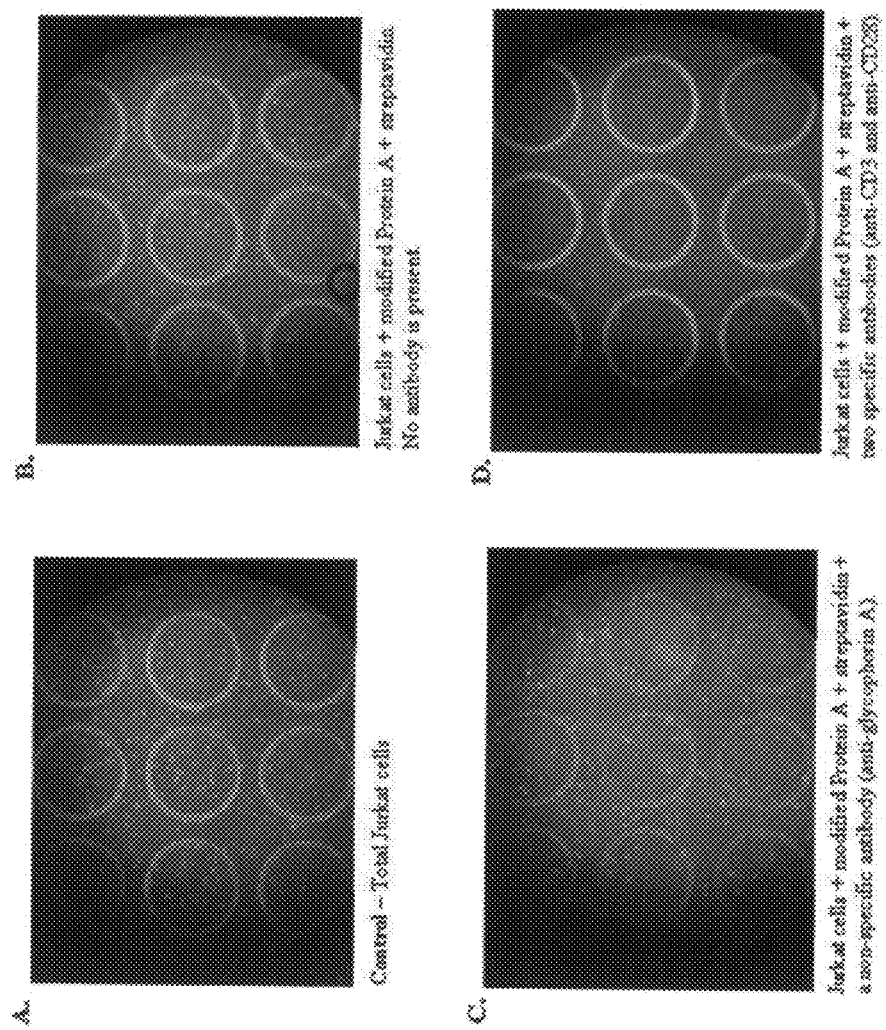

FIGS. 48A-D are light microscopy images showing cell specific purification only in the presence of modified protein A, Streptavidin and cell-specific antibodies (FIG. 48D).

Figure 49:
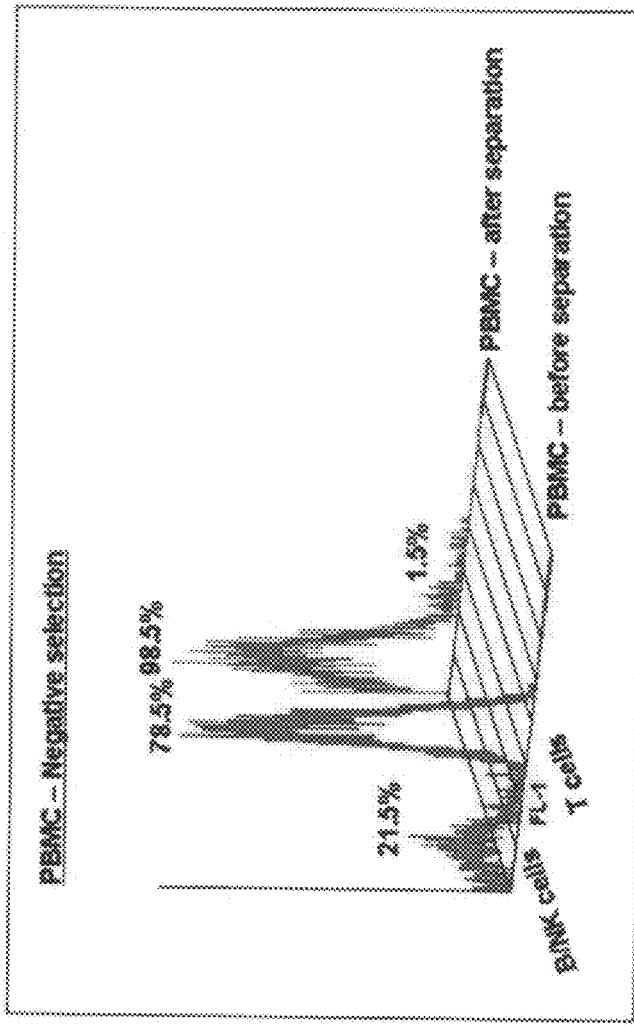

FIG. 49 is a FACS image showing the effect molecular weight/density separation on purity of cell populations obtained by negative selection.

Figure 50:
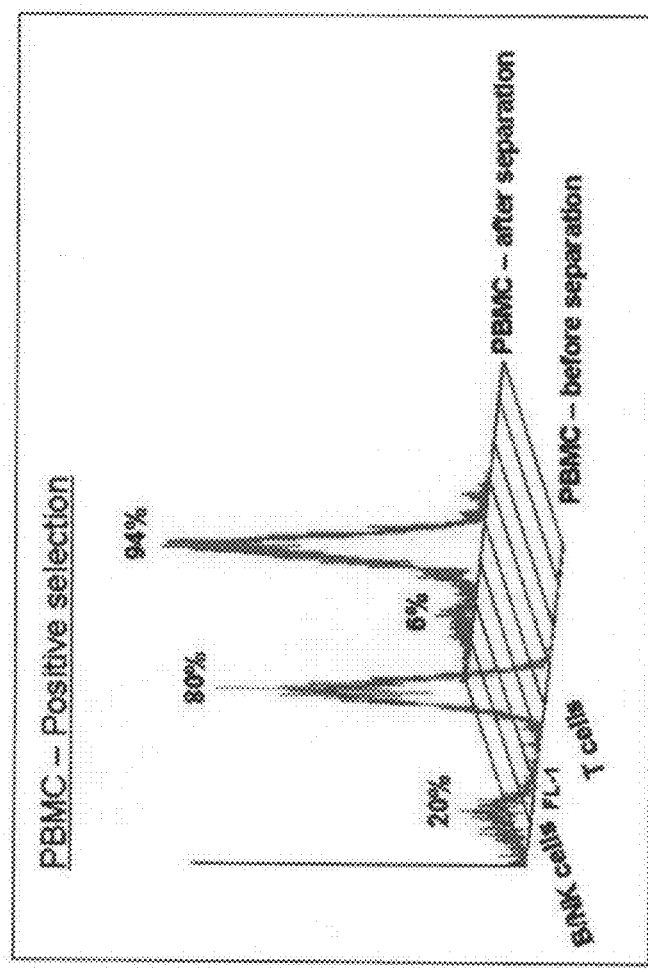

FIG. 50 is a FACS image showing the effect molecular weight/density separation on purity of cell populations obtained by positive selection.

FIG. 51 is a schematic flow-chart showing purification of sub-cell populations by sequential use of a number of antibodies. The scheme outlines a process where a cell subpopulation with two distinct epitopes A and B can be isolated from cells containing either epitope A or C. In the first step, cells presenting both A and B epitopes are positively selected by utilizing an anti-epitope A antibody (FIG. 51 steps 1-2). This would remove the majority of cells containing the C epitope and result in a mixture of cells presenting both the A and A+B epitopes. Selected cells are then subjected to biotin and to a peptide representing epitope A. Under these conditions, the macro-complex would dissociate while the added peptide compete with epitope A on binding to the antibody, thereby releasing the antibody from the cell membrane (FIG. 51 step 3). By applying physical separation (based on weight, size or density) all reagents (e.g., biotin, free unbound anti-epitope A mAb, Avidin:Biotin complexes) are removed and resuspended cells are incubated with a secondary antibody directed at epitope B (FIG. 51 step 4). Addition of the desthiobiotinylated protein A and streptavidin would preferentially precipitate cells containing the A+B epitopes whereas cells containing only epitope A will be excluded (FIG. 51 step 5). By repeating the steps described in FIG. 51, sub-cell populations containing more than two distinct epitopes may be isolated accordingly.

FIGS. 52A-D are schemes showing different configurations of double modified albumin (i.e., composite ligand) for purification/depletion of molecules.

FIGS. 53A-B shows homogeneous and heterogenous configurations for purification of His-tagged molecules using a double modified albumin as the composite ligand.

FIGS. 54A-B shows the purification of a His-tagged protein using the methods shown in FIGS. 53A-B.

Figure 54C:
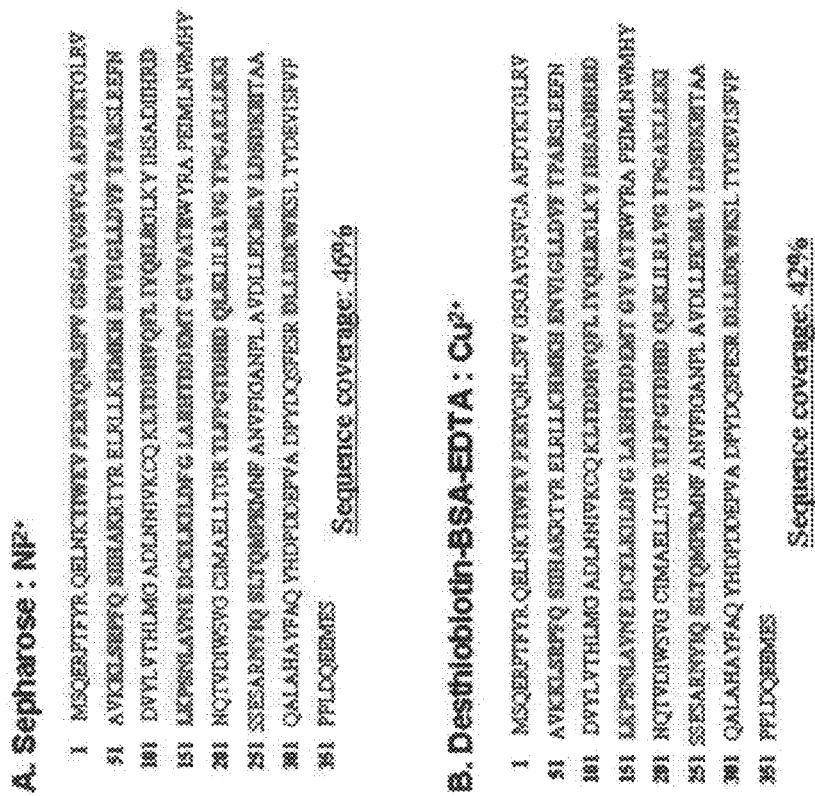

FIG. 54C shows mass-spectrometry analysis results of the protein isolated (SEQ ID NO: 1) as shown in FIGS. 54A-B.

FIG. 55 shows a configuration for purifying biotinylated proteins using the teachings of the present invention.

FIG. 56 shows depletion of glucose oxidase and porcine thyroglobulin with a desthiobiotinylated-concanavalin A and free avidin. Lane 1 Bio-Rad prestained protein markers; lane 2 porcine thyroglobulin (a) and glucose oxidase (b); lane 3 *E. coli* cell lysate; lane 4 mixture of the cell lysate and the two glycoproteins shown in lane 2; lane 5 content of supernatant after depletion of the two glycoproteins with a desthiobiotinylated-concanavalin A and free avidin.

FIGS. 57A-B are bar graphs showing the purity and yield obtained by the magnetic bead technology kit (Miltenyi CD3 Microbeads, cat. 130-050-101), and the present methodology.

FIGS. 58A-C is a dot plot presentation of the results shown in FIGS. 57A-B.

DESCRIPTION OF THE PREFERRED EMBODIMENTS

The present invention is of compositions, which can be used for purifying and crystallizing molecules of interest.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Cost effective commercial-scale production of proteins, such as therapeutic proteins, depends largely on the development of fast and efficient methods of purification since it is the purification step which typically contributes most of the cost involved in large scale production of proteins.

There is thus, a need for simple, cost effective processes, which can be used to purify proteins and other commercially important molecules.

The state of the art approach in protein purification is Affinity Precipitation (AP) which is based on the use of "smart" polymers coupled to a recognition unit, which binds the protein of interest. These smart polymers respond to small changes in environmental stimuli with large, sometimes discontinuous changes in their physical state or properties, resulting in phase separation from aqueous solution or order-of-magnitude changes in hydrogel size and precipitation of the molecule of interest. However, at present, the promise of smart polymers has not been realized due to several drawbacks including, entrapment of impurities during the precipitation process, adsorption of impurities to the polymeric matrix, decreased affinity of the protein recognition unit and working conditions which may lead to a purified protein with reduced activity.

While reducing the present invention to practice, the present inventors designed novel compositions, which can be used for cost-effective and efficient purification of proteins as well as other molecules and cells of interest.

As is illustrated hereinbelow and in the Examples section which follows, the compositions of the present invention specifically bind target molecules to form non-covalent complexes which can be precipitated and collected under mild conditions. Furthermore, contrary to prior art purifying compositions, the compositions of the present invention are not immobilized (such as to a smart polymer) which reduces affinity of the ligand towards the target molecule, limits the amount of ligand used, necessitates the use of sophisticated laboratory equipment (HPLC) requiring high maintenance, leads to column fouling and limits column usage to a single covalently bound ligand.

Thus, according to one aspect of the present invention there is provided a composition-of-matter, which is suitable for purification of a target molecule or cell of interest.

The target molecule can be a macromolecule such as a protein (e.g., a prion), a carbohydrate, a glycoprotein, a lipid or a nucleic acid sequence (e.g. DNA such as plasmids, RNA) or a small molecule such as a chemical or a combination of same (e.g., toxins such as endotoxins). Although most of the examples provided herein describe proteinacious target molecules, it will be appreciated that the present invention is not limited to such targets.

The target cell can be a eukaryotic cell, a prokaryotic cell or a viral cell.

The composition-of-matter of the present invention includes at least one ligand capable of binding the molecule or cell of interest and at least one coordinating moiety which is selected capable of directing the composition-of-matter to form a non-covalent complex when co-incubated with a coordinator ion or molecule.

As used herein the term "ligand" refers to a synthetic or a naturally occurring molecule preferably exhibiting high affinity (e.g. $K_D<10^{-5}$) binding to the target molecule of interest and as such the two are capable of specifically interacting. When the target of interest is a cell, the ligand is selected capable of binding a protein, a carbohydrate or chemical, which is expressed on the surface of the cell (e.g. cellular marker). Preferably, ligand binding to the molecule or cell of interest is a non-covalent binding. The ligand according to this aspect of the present invention may be mono, bi (antibody, growth factor) or multi-valent ligand and may exhibit affinity to one or more molecules or cells of interest (e.g. bi-specific antibodies). Examples of ligands which may be used in accordance with the present invention include, but are not limited to, antibodies, mimetics (e.g. Affibodies® see: U.S. Pat. Nos. 5,831,012, 6,534,628 and 6,740,734) or fragments thereof, epitope tags, antigens, biotin and derivatives thereof, avidin and derivatives thereof, metal ions, receptors and fragments thereof (e.g. EGF binding domain), enzymes (e.g. proteases) and mutants thereof (e.g. catalytic inactive), substrates (e.g. heparin), lectins (e.g. concanavalin A), carbohydrates (e.g. heparin), nucleic acid sequences [e.g. aptamers and Spiegelmers [Wlotzka® (2002) Proc. Natl. Acad. Sci. USA 99:8898-02], dyes which often interact with the catalytic site of an enzyme mimicking the structure of a natural substrate or co-factor and consisting of a chromophore (e.g. azo dyes, anthraquinone, or phthalocyanine), linked to a reactive group (e.g. a mono- or dichlorotriazine ring, see, Denzili (2001) J Biochem Biophys Methods. 49(1-3):391-416), small molecule chemicals, receptor ligands (e.g. growth factors and hormones), mimetics having the same binding function but distinct chemical structure, or fragments thereof (e.g. EGF domain), ion ligands (e.g. calmodulin), protein A, protein G and protein L or mimetics thereof (e.g. PAM, see Fassina (1996) J. Mol. Recognit. 9:564-9], chemicals (e.g. cibacron Blue which bind enzymes and serum albumin; amino acids e.g. lysine and arginine which bind serine proteases) and magnetic molecules such as high spin organic molecules and polymers (see http://www.chem.unl.edu/rajca/high-spin.html).

According to a preferred embodiment the ligand is a an antibody binding moiety. Such an antibody binding moiety can be any molecule which is capable of binding an immunoglobulin region of an antibody. Examples include but are not limited to protein A/G/L (as well as active portions thereof, i.e., capable of binding immunoglobulins, such as the ZZ domain) as well as antibodies (e.g., secondary antibodies) or antibody fragments. Methods of generating antibodies or fragments of same are well known in the art.

According to an embodiment of the present invention the ligand is a "composite ligand" composed of a scaffold/platform moiety attached to a target recognition moiety.

The scaffold/platform portion is typically an inert molecule which comprises sufficient active groups (e.g., amines) for conjugating the target recognition moieties.

The composite ligand is typically synthetic and the chemistry of synthesis depends on the active groups as well as on the nature of the target recognition moiety. Methods of synthesizing such composite ligands are well known in the art.

The target recognition moiety can be any affinity binding molecule of an affinity binding pair. The target recognition moiety may bind the target directly or indirectly (e.g., via a metal coordination, see Example 14).

Examples of scaffolds, target recognition moieties and targets are provided in Examples 13 in the Examples section below.

As used herein the phrase "coordinating moiety" refers to any molecule having sufficient affinity (e.g. $K_D<10^{-5}$) to a coordinator ion or molecule. The coordinating moiety can direct the composition-of-matter of this aspect of the present invention to form a non-covalent complex when co-incubated with a coordinator ion or molecule. Examples of coordinating moieties which can be used in accordance with the present invention include but are not limited to, epitopes (antigenic determinants antigens to which the paratope of an antibody binds), antibodies, chelators (e.g. His-tag, see other example in Example 1 of the Examples section which follows, FIGS. 1, 25 and 26), biotin (see FIG. 7), nucleic acid sequences (see FIG. 6), protein A or G (FIG. 9), electron poor molecules and electron rich molecules (see Example 2 of the Examples section which follows and FIG. 8) and other molecules described hereinabove (see examples for ligands).

It will be appreciated that a number of coordinating moieties can be bound to the ligand described above (see FIGS. 1a-f).

It will be further appreciated that different coordinating moieties can be attached to the ligand such as a chelator and an electron rich/poor molecule to form a complex such as is shown in FIG. 19. Such a combination of binding moieties may mediate the formation of polymers or ordered sheets (i.e., networks) containing the molecule of interest as is illustrated in FIGS. 23a-b and 24, respectively.

To avoid competition and/or further problems in the recovery of the molecule of interest from the complex, the coordinating moiety is selected so as to negate the possibility of coordinating moiety-ligand interaction or coordinating moiety-target molecule interaction. For example, if the ligand is an antigen having an affinity towards an immunoglobulin of interest then the coordinating moiety is preferably not an epitope tag or an antibody capable of binding the antigen.

As used herein the phrase "coordinator ion or molecule" refers to a soluble entity (i.e., molecule or ion), which exhibits sufficient affinity (i.e., $K_D<10^{-5}$) to the coordinating moiety and as such is capable of directing the composition-of-matter of this aspect of the present invention to form a non-covalent complex. Examples of coordinator molecules which can be used in accordance with the present invention include but are not limited to, avidin and derivatives thereof, antibodies, electron rich molecules, electron poor molecules and the like. Examples of coordinator ions which can be used in accordance with the present invention include but are not limited to, mono, bis or tri valent metals. FIG. 25 illustrates examples of chelators and metals which can be used as a coordinator ion by the present invention. FIG. 26 lists examples of electron rich molecules and electron poor molecules which can be used by the present invention. Methods of generating antibodies and antibody fragments as well as single chain antibodies are described in Harlow and Lane, Antibodies: A Laboratory Manual, Cold Spring Harbor Laboratory, New York, 1988, incorporated herein by reference; Goldenberg, U.S. Pat. Nos. 4,036,945 and 4,331,647, and references contained therein; See also Porter, R. R. [Biochem. J. 73: 119-126 (1959); Whitlow and Filpula, Methods 2: 97-105 (1991); Bird et al., Science 242:423-426 (1988); Pack et al., Bio/Technology 11:1271-77 (1993); and U.S. Pat. No. 4,946,778].

Preferably, the composition of this aspect of the present invention includes the coordinator ion or molecule (i.e., a two-part composition).

Also, it is appreciated that all the components of the two-part composition are provided non-immobilized (i.e., soluble, free) such that only upon coordination, the complex precipitates and becomes insoluble. However, in sharp difference to standard affinity purification reagents, the precipitated complex comprises non-covalent interactions.

The ligand of this aspect of the present invention may be bound directly to the coordinating moiety, depending on the chemistry of the two. Measures are taken, though, to maintain recognition (e.g. affinity) of the ligand to the molecule of interest. When needed (e.g. steric hindrance), the ligand may be bound to the coordinating moiety via a linker. A general synthetic pathway for modification of representative chelators with a general ligand is shown in FIG. 14. Margherita et al. (1993) J. Biochem. Biophys. Methods 38:17-28 provides synthetic procedures which may be used to attach the ligand to the coordinating moiety of the present invention.

When the ligand and coordinating moiety bound thereto are both proteins (e.g. growth factor and epitope tag, respectively), synthesis of a fusion protein can be effected by molecular biology methods (e.g. PCR) or biochemical methods (solid phase peptide synthesis).

Complexes of the present invention can be of various complexity levels, such as, monomers (see FIGS. 12 and 13a-b depicting a three ligand complex), dimers, polymers (see FIGS. 23a-b depicting formation of a polymer via a combined linker as described in Example 3 of the Examples section), sheets (see FIG. 24 in which sheets are formed when a single surface exposed Trp residue of a target molecule forms electron rich/poor relations with a TNB—TNB entity) and lattices which may form three dimensional (3D) structures (such as when more than one surface exposed Trp residues form electron rich/poor relations). It is well established that the higher complexity of the complex the more rigid is the structure enabling use thereof in crystallization procedures as further described hereinbelow. Furthermore, large complexes will phase separate more rapidly, negating the use of further centrifugation steps.

It will be appreciated that in cases where the composition of the present invention is utilized for purification of a target molecule/cell (see below for further description), the ligand is selected such that the target molecule/cell is uniformly bound to the complex. For example, the ligand can be selected such that the target molecule/cell bound by the complex is only associated with a single ligand molecule of the complex or with a predetermined number of ligand molecules. As is further described below, such uniform association between ligand and target molecule/cell ensures that purification of the target from the complex is uniform, i.e. that a single elution step releases substantially all of the complex-bound target.

Examples of ligand configuration which enable such uniform binding of the target molecule/cell, include: peptides (i.e., cyclic or linear), Protein A or G or L, antibodies, lectines (e.g., concanavalin A from Jack bean, Jacalin from Jack fruit), various dyes (e.g., Cibacron Blue 3GA) and aptamers.

The compositions of the present invention can be packed in a purification kit which may include additional buffers and additives, as described hereinbelow. It will be appreciated that such kits may include a number of ligands for purifying a number of molecules from a single sample. However, to simplify precipitation (e.g. using the same reaction buffer, temperature conditions, pH and the like) and further purification steps, the coordinating moieties and coordinator ions or molecules are selected the same.

As mentioned hereinabove, the compositions of the present invention may be used to purify a molecule or cell of interest from a sample.

Thus, according to another aspect of the present invention there is provided a method of purifying a molecule of interest.

As used herein the term "purifying" refers to at least separating the molecule of interest from the sample by changing its solubility upon binding to the composition of the present invention and precipitation thereof (i.e., phase separation).

The method of this aspect of the present invention is effected by contacting a sample including the molecule of interest with a composition of the present invention and collecting a precipitate which includes a complex formed from the composition-of-matter of the present invention and the molecule of interest, thereby purifying the molecule of interest.

As used herein the term "sample" refers to a solution including the molecule of interest and possibly one or more contaminants (i.e., substances that are different from the desired molecule of interest). For example when the molecule of interest is a secreted recombinant polypeptide, the sample can be the conditioned medium, which may include in addition to the recombinant polypeptide, serum proteins as well as metabolites and other polypeptides, which are secreted from the cells. When the sample includes no contaminants, purifying refers to concentrating.

In order to initiate purification, the composition-of-matter of the present invention is first contacted with the sample. This is preferably effected by adding the ligand attached to the coordinating moiety to the sample allowing binding of the molecule of interest to the ligand and then adding the coordinator ion or molecule to allow complex formation and precipitation of the molecule of interest. In order to avoid rapid formation of complexes (which may result in the entrapment of contaminants) slow addition of the coordinator to the sample while stirring is preferred. Controllable rate of precipitation can also be achieved by adding free coordinating entity (i.e., not bound to the ligand), which may also lead to the formation of smaller complexes which may be beneficial in a variety of applications such as for the formation of immunogens, further described hereinbelow.

When the target comprise cells, measures are taken to spin the tube over its axis so is to improve cell-specific complex formation until the sample becomes turbid and comprise the target cells of interest (see Example 11 of the Examples section below).

Once the complex described above is formed (seconds to hours), precipitation of the complex may be facilitated by centrifugation (e.g. ultra-centrifugation), although in some cases (for example, in the case of large complexes) centrifugation is not necessary.

Depending on the intended use the molecule of interest, the precipitate may be subjected to further purification steps in order to recover the molecule of interest from the complex. This may be effected by using a number of biochemical methods which are well known in the art. Examples include, but are not limited to, fractionation on a hydrophobic interaction chromatography (e.g. on phenyl sepharose), ethanol precipitation, isoelectric focusing, reverse phase HPLC, chromatography on silica, chromatography on heparin sepharose, anion exchange chromatography, cation exchange chromatography, chromatofocusing, SDS-PAGE, ammonium sulfate precipitation, hydroxylapatite chromatography, gel electrophoresis, dialysis, and affinity chromatography (e.g. using protein A, protein G, an antibody, a specific substrate, ligand or antigen as the capture reagent).

For cell precipitation purposes (i.e., depletion or purification), once the complex is formed collection of the precipitate is effected by size filtration or densitometry as described hereinbelow (see Examples 12 of the Examples section which follows).

It will be appreciated that simple addition of clean reaction solution (e.g. buffer) may be added to the precipitate to elute low affinity bound impurities which were precipitated during complex formation.

It will be further appreciated that any of the above-described purification procedures may be repetitively applied on the sample (i.e., precipitate) to increase the yield and or purity of the target molecule.

Preferably, the composition-of-matter and coordinator ion or molecule are selected so as to enable rapid and easy isolation of the target molecule from the complex formed. For example, the molecule of interest may be eluted directly from the complex, provided that the elution conditions employed do not disturb binding of the coordinating moiety to the coordinator (see FIGS. 4-5). For example, when the coordinating moiety used in the complex is a chelator, high ionic strength may be applied to elute the molecule of interest, since it is well established that it does not effect metal-chelator interactions. Alternatively, elution with chaotropic salt may be used, since it has been shown that metal-chelator interactions are resistant to high salt conditions enabling elution of the target molecule at such conditions [Porath (1983) Biochemistry 22:1621-1630].

The complex can be re-solubilized by the addition of free (unmodified) chelator (i.e., coordinating moiety), which competes with the coordinator metal (FIG. 3). Ultrafiltration or dialysis may be used, thereafter, to remove most of the chelated metal and the competing chelator. The solubilized complex (i.e., molecule of interest:ligand-coordinating moiety) can then be loaded on an immobilized metal affinity column [e.g. iminodiacetic acid (IDA) and nitrilotriacetic acid (NTA)]. It will be appreciated that when high affinity chelators are used (e.g. catechol), measures are taken to use immobilized metal affinity ion column modified with the same or with other chelator having similar binding affinities toward the immobilized metal, to avoid elution of the ligand:chelator agent from the column instead of binding to it.

Application of suitable elution conditions will result in the elution of the target molecule keeping the ligand-coordinating moiety bound to the column. A final desalting procedure may be applied to obtain the final product.

Regeneration of the ligand-coordinating moiety is of high economical value, since synthesis of such a fusion molecule may contribute most of the cost and labor involved in the methodology described herein. Thus, for example, regeneration of the ligand-coordinating moiety can be achieved by loading the above-described column with a competing chelator or changing column pH followed by ultrafiltration that may separate between the free chelator and the desired ligand-coordinating moiety.

The Examples section which follows provides specific examples of binding/elution protocols which can be used with the present invention. It will be appreciated however, that the described parameters can be varied according to the immobilized target and purity needs.

Thus, several binding/washing/elution/regeneration parameters can be utilized by the present invention, including:

(i) diverse pH values (e.g. pH=2–10);
(ii) presence of different salts (other than NaCl) or in combination and in various concentrations (e.g. 1 μM-5M);
(iii) presence or absence of free metal chelator/s or combinations of chelators (e.g. imidazole catechol, His and catechol, His and EDTA, phosphate and EGTA, Citrate and 1,10-phenanthroline, etc.);
(iv) different buffers (other than sodium phosphate) i.e. Tris, Citrate, PBS, Gly at various concentrations and pH values;
(v) presence or absence of radical scavengers;
(vi) addition of divalent, trivalent or tetravalent metals (Ca2+, Mg2+, Mn2+, Co2+, Al3+, Th4+);
(vii) various temperature ranges (other than 0-4° C.);
(viii) various incubation times, e.g. the binding of the modified ligand to the target may change when that target is at low concentration or binding between the two is relatively weak, ligand will be required when the target is at low concentration or when the affinity of the ligand toward the target is low;
(ix) different sequences of additions, for example, addition of salt, then ligand then free chelator, then metal, or, addition of salt, then ligand, then metal, then free chelator;
(x) use of ligands modified with chelators other than catechol (e.g. hydroxy quinoline derivatives);
(xi) modification of a ligand with a chelator (for example) having different leaving groups (e.g. catechol-meleimide, catechol-iodacetamide, catechol-chloroactyl); and/or
(xii) with or without use of detergents (e.g. SDS, Triton)

The above-described purification methodology can be applied for the isolation of various recombinant and natural substances which are of high research or clinical value such as recombinant growth factors and blood protein products (e.g. von Willebrand Factor and Factor VIII which are therapeutic proteins effective in replacement therapy for von Willebrand's disease and Hemophilia A, respectively).

As mentioned hereinabove, the compositions of the present invention may also be used to isolate particular populations of cells, antigens, viruses, plasmids and the like. The following section exemplifies use of the present invention in such applications.

Positive selection of cells The present invention can be utilized to isolate cancer cells or stem cells which possess unique surface markers. For example, cells displaying CD34 and CD105 [see Pierelli (2001) Leuk. Lymphoma 42(6): 1195-206]) can be isolated by incubation of a cell suspension with a mAb directed at an epitope on the target cell (immuno labeled), followed by addition of desthiobiotinylated protein A (which could be added together with the mAb itself). The target cell-mAb-modified protein A (or G or L) complex (also referred to herein as the Precipitating complex) would precipitate the target cell upon addition of free avidin. The supernatant will be discarded while the pellet containing the target cell would be either directly used; agitated to free bound cells from the precipitate; incubated in the presence of a competing molecule (e.g. peptide) which would release the target cell by competing with the epitope of the cell on binding to the mAb; or incubated in the presence biotin (or its analogues) for partial or total dissolution of the pellet thereby, enabling an effective cell release (for further detail see FIG. 33).

Negative selection of cells the precipitating complex described above can be used along with a single mAb or several mAbs targeted at non-relevant cells in order to precipitate non-target cells and form a supernatant containing enriched medium of target cells.

Specific antigen precipitation the precipitating complex described above can be utilized with a target antigen known to bind to an mAb/s forming a part of the complex.

Depletion of viruses the precipitating complex described above can be used with virus or viruses containing an epitope known to bind to an mAb/s forming a part of the complex.

Precipitation of DNA/RNA-protein complexes the precipitating complex described above can utilize an mAb/s which can bind DNA/RNA-protein.

Plasmid purification the Precipitating complex described above can utilize an antibody which binds directly to a plasmid.

Sample preparation—The above mentioned ligands (e.g., composite ligands) can be used to deplete samples from impurities such as immunoglobulin (in this case the target recognition moiety may be protein A) and BSA (in this case the target recognition moiety is Cibarcon-Blue).

Detection, quantification and purification of biotinylated proteins—see Example 15 of the Examples section which follows.

The present compositions can also be utilized for reducing contamination or background. For example, several ligands may be modified with the same coordinating entity (e.g. biotin) and incubated in a medium containing impurities known to bind to the modified ligands. Removal of impurities will be initiated by addition of free avidin (for example), and the enriched supernatant could be used for further applications (see FIG. 34 for further detail).

Purification of recombinant proteins possessing fusion partners such as the Z (or ZZ) domain of Protein A could be purified in the presence of a modified human IgG (hIgG) to which the Z domain binds specifically, followed by addition of an appropriate transition metal which would generate insoluble macro-complexes containing the fusion protein (see FIG. 35 for further detail). These macro-complexes would precipitate while impurities left soluble in the supernatant will be excluded. The same could be applied to other recombinant proteins with the following fusion partners:

(i) Recombinant protein—ABP (Albumin Binding Protein of Protein G) and a modified HSA (Human Serum Albumin).

(ii) Recombinant protein—MBP (*E. coli* Maltose Binding Protein) and a modified amylose.

(iii) Recombinant protein—GST and a modified Glutathione.

(iv) Recombinant protein—FLAG peptide and a modified mAb M1 or mAb M2.

As mentioned, the present invention can also utilize non-immobilized multivalent ligands (NML) which can be generated via covalent linking of a protein (e.g. ovalbumin) with any ligand (e.g. Fluorescein) and a complexing entity (e.g. desthiobiotin). The modified protein (see FIG. 36 for further detail) serves as the MNL since it is capable of interacting specifically with a Target molecule (FIG. 36 step b) and be further precipitated upon addition of an appropriate mediator entity (e.g. free avidin) (FIG. 36 step c) which will interconnect modified ovalbumins (FIG. 36 step d). Thus, specific precipitation is initiated in the presence of avidin whereas impurities are left soluble in the supernatant and are excluded. The Target is then eluted from the precipitate (i.e. pellet) under conditions favoring dissociation of the Target rather than dissociation of the [ovalbumin-desthiobiotin:avidin] multi-complex (FIG. 36 step d)

An efficient elution may be accomplished by using networks with lower degree of complexity (e.g. a network which includes larger holes). These could be generated by an avidin solution containing also bis, tris or multi avidin complexes that were cross-linked prior to their incubation with bis, tris or multi biotin moieties. (or their derivatives), via modification of the ligand with a complexing (coordinating) entity having extended spacer arms or by using avidin molecules that were incubated with free biotin prior to their use as a coordinator molecule. Similarly, free biotin may be present before the addition of avidin (see Example 7).

It is well established that due to shortage in human organs, in-vitro organogenesis is emerging as an optimal substitute. To this end, stem cells which are capable of differentiating to any desired cell lineage must be isolated. Thus, for example, to isolate hematopoietic stem/progenitor cells a number of ligands may be employed which bind to surface markers which are unique to this cell population, such as CD34 and CD105 [see Pierelli (2001) Leuk. Lymphoma 42(6):1195-206].

Another example is the isolation of erythrocytes using lectin ligands, such as concanavalin A [Sharon (1972) Science 177:949; Goldstein (1965) Biochemistry 4:876].

Viral cell isolation may be effected using various ligands which are specific for viral cells of interest [see www.bdbiosciences.com/clontech/archive/JAN04UPD/Adeno-X.shtml].

Specifically, retroviruses may be isolated by the compositions of the present invention which are designed to include a heparin ligand [Kohleisen (1996) J Virol Methods 60(1):89-101].

Cell isolation using the above-described methodology may be effected with preceding steps of sample de-bulking which is effected to isolate cells based on cell density or size (e.g. centrifugation) and further steps of selective cell-enrichment (e.g. FACS).

On top of their purifying capabilities, the compositions of the present invention may also be used to deplete a sample from undesired molecules or cells.

This is effected by contacting the sample including the undesired target molecule or cell of interest with the composition of the present invention such that a complex is formed (described above) and removing the precipitate. The clarified sample is the supernatant.

This method have various uses such as in depleting tumor cells from bone marrow samples, depleting B cells and monocytes for the isolation and enrichment of T cells and $CD8^+$ cells or $CD\ 4^+$ cells from peripheral blood, spleen, thymus, lymph or bone marrow samples, depleting pathogens and unwanted substances (e.g. prions, toxins) from biological samples, protein purification (e.g. depleting high molecular weight proteins such as BSA) and the like.

As mentioned hereinabove multiple ligands may be employed for the depletion of a number of targets from a given sample such as for the removal of highly abundant proteins from biological fluids (e.g. albumin, IgG, antitrypsin, IgA, transferrin and haptoglobin, see http://www.chem.agilent.com/cag/prod/ca/51882709 small.pdf).

The unique properties of the novel compositions of the present invention provide numerous advantages over prior art precipitation compositions (e.g. smart polymers), some of these advantages are summerized infra.

(i) Low cost purification; the present methodology does not rely upon sophisticated laboratory equipment such as HPLC, thereby circumventing machine maintenance and operating costs.

(ii) Easy up scaling; the present methodology is not restricted by limited capacity of affinity columns having diffusion limitations. Essentially, the amount of added precipitating complex is unlimited.

(iii) Mild precipitation process; averts limitations resulting from substantial changes in pH, ionic strength or temperature.

(iv) Uniform purification process; in the case of a complex having a ligand capable of uniform (e.g. monovalent) interactions with the target (i.e. a predetermined number of ligands per target or vice versa), uniform purification can be achieved under selected elution conditions since the target molecules/cells are uniformly bound to the complex.

(v) Control over the precipitation process; precipitation may be governed by, slow addition of an appropriate coordinator ion or molecule to the precipitation mixture; use of mono and/or multi-valent coordinators; use of coordinator ions or molecules with different affinities towards the coordinating moiety; addition of the non-immobilized free coordinating moieties to avoid non-specific binding and entrapment of impurities prior to, during or following formation of a non-covalent polymer, sheet or lattice [Mattiasson et al., (1998) J. Mol. Recognit. 11:211-216; Hilbrig and Freitag (2003) J. Chromatogr. B 790:79-90]; as well as by varying temperature conditions. It is well established that various molecules exhibit lower solubility as the temperature decreases, therefore, controlling temperature conditions may regulate the rate and degree of precipitation. It will be appreciated, though, that low temperature conditions may lead to entrapment of impurities due to a fast precipitation process, while high temperature conditions may lead to low yields of the target molecule (e.g. denaturing temperatures). Thus measures are taken to achieve optimal temperature conditions, while considering the above parameters.

(vi) Reduced contamination background; contaminants cannot bind the coordinator entity and as such they cannot bind tightly to the non-covalent matrix, allowing their removal prior to the elution step. Furthermore, contaminations deriving from the ligand biological background (molecules which co-purified with the ligand) may become modified as well as the ligand itself [provided that the ligand and the contaminants share the same chemistry (e.g. both being proteins)], and might become part of the precipitating complex. Under suitable elution conditions, the target molecule will be recovered, while the modified contaminations will not.

(vii) Binding in homogenous solutions; it is well established that binding in homogeneous solution is more rapid and more effective than in heterogeneous phases such as in affinity chromatography [AC, Schneider et al., (1981) Ann. NY Acad. Sci. 369, 257-263; Lowe (2001) J. Biochem. Biophys. Methods 49, 561-574]. For example, high molecular mass polymers (used in AP) are known to form highly coiled and viscous structures in solutions that hinder the access of incoming macromolecules such as the target molecules as in many affinity separation strategies. [Vaida et al., (1999) Biotechnol. Bioeng. 64:418].

(viii) No immobilization of the ligand—further described hereinabove.

(ix) Easy resolubilization of the complex; the complex is generated by non-covalent interactions.

(x) Sanitizing under harsh conditions; the composition is not covalently bound to a matrix and as such can be removed from any device, allowing application of sanitizing conditions to clean the device (column) from non-specifically bound impurities.

The ability of the compositions of the present invention to arrange molecules of interest in ordered complexes such as in dimers, trimers, polymers, sheets or lattices also enables use thereof in facilitating crystallization of macromolecules such as proteins, in particular membranous proteins. As is well known in the art, a crystal structure represents ordered arrangement of a molecule in a three dimensional space. Such ordered arrangement can be egenerated by reducing the number of free molecules in a given space (see FIGS. 10*a-b* and 11*a-c*).

Thus, according to yet another aspect of the present invention there is provided a composition for crystallizing a molecule of interest.

As used herein the term "crystallizing" refers to the solidification of the molecule of interest so as to form a regularly repeating internal arrangement of its atoms and often external plane faces.

The composition of this aspect of the present invention includes at least one ligand capable of binding the molecule of interest, wherein the ligand is attached to at least one coordinating moiety; and a coordinator capable of non-covalently binding the at least one coordinating moiety, wherein the at least one coordinating moiety and the coordinator are capable of forming a complex when co-incubated and whereas the composition is selected so as to define the relative spatial positioning and orientation of the molecule of interest when bound thereto, thereby facilitating formation of a crystal therefrom under inducing crystallization conditions.

It will be appreciated that the use of covalent multi ligand complexes has been previously attempted in the crystallization of soluble proteins [Dessen (1995) Biochemistry 34:4933-4942; Moothoo (1998) Acta. Cryst. D54 1023-1025; Bhattacharyya (1987) J. Biol. Chem. 262:1288-1293]. However, synthesis of multi-ligand complexes which have more than two ligands per molecule is technically difficult and expensive; Furthermore, the three-dimensional structure of the target protein should be known in advance to synthesize multi ligand complexes which have the optimal distance between the ligands to bind enough target molecules to occupy all target binding sites in the multi-ligand complex, as such, these ligands were never used for the crystallization of membrane proteins.

The present invention circumvents these, by synthesizing only the basic unit in the non-covalent multi-ligand, (having the general structure of: Ligand—coordinating moiety) which is far easier to achieve, faster and cheaper. This basic unit, would form non-covalent tri-ligand only by adding the multi valent coordinator ion or molecule. Thus, a single synthesis step is used to form di, tri, tetra or higher multi ligands that may be used for crystallization experiments.

In order to produce crystals of a molecule of interest (preferably of membrane proteins) the compositions of the preset invention are contacted with a sample, which includes the molecule of interest preferably provided at a predetermined purity and concentration.

Typically, the crystallization sample is a liquid sample. For example, when the molecule of interest is a membrane protein, the crystallization sample, according to this aspect of the present invention, is a membrane preparation. Methods of generating membrane preparations are described in Strategies for Protein Purification and Characterization—A Laboratory Course Manual" CSHL Press (1996).

Once the molecule of interest is bound to the composition of the present invention, such that its relative spatial positioning and orientation are well defined, the sample is subjected to suitable crystallization conditions. Several crystallization approaches which are known in the art can be applied to the sample in order to facilitate crystallization of the molecule of interest. Examples of crystallization approaches include, but are not limited to, the free interface diffusion method [Salemme, F. R. (1972) Arch. Biochem. Biophys. 1.51:533-539], vapor diffusion in the hanging or sitting drop method (McPherson, A. (1982) Preparation and Analysis of Protein Crystals, John Wiley and Son, New York, pp 82-127), and liquid dialysis (Bailey, K. (1940) Nature 145:934-935).

Presently, the hanging drop method is the most commonly used method for growing macromolecular crystals from solution; this approach is especially suitable for generating protein crystals. Typically, a droplet containing a protein solution is spotted on a cover slip and suspended in a sealed chamber that contains a reservoir with a higher concentration of precipitating agent. Over time, the solution in the droplet equilibrates with the reservoir by diffusing water vapor from the droplet, thereby slowly increasing the concentration of the protein and precipitating agent within the droplet, which in turn results in precipitation or crystallization of the protein.

Crystals obtained using the above-described methodology, have a resolution of preferably less than 3 Å, more preferably less than 2.5 Å, even more preferably less than 2 Å.

Compositions of the present invention may have evident utility in assaying analytes from complex mixtures such as serum samples, which may have obvious diagnostic advantages.

Thus, the present invention envisages a method of detecting predisposition to, or presence of a disease associated with a molecule of interest in a subject.

An example of a disease which is associated with a molecule of interest is prostate cancer which may be detected by the presence of prostate specific antigen [PSA, e.g. >0.4 ng/ml, Boccon-Gibod Int J Clin Pract. (2004) 58(4):382-90].

The compositions of the present invention are contacted with a biological sample obtained from the subject whereby the level of complex formation including the molecule of interest is indicative of predisposition to, or presence of the disease associated with the molecule of interest in the subject.

As used herein the phrase "biological sample" refers to a sample of tissue or fluid isolated from a subject, including but not limited to, for example, plasma, serum, spinal fluid, lymph fluid, the external sections of the skin, respiratory, intestinal, and genitourinary tracts, tears, saliva, milk, blood cells, tumors, neuronal tissue, organs, and also samples of in vivo cell culture constituents.

To facilitate detection and quantification of the molecule of interest in the complexes, the biological sample or the composition is preferably labeled (e.g. fluorescent, radioactive labeling).

Compositions of the present invention may also be utilized to qualify and quantify substances present in a liquid or gaseous samples which may be of great importance in clinical, environmental, health and safety, remote sensing, military, food/beverage and chemical processing applications.

Abnormal protein interaction governs the development of many pathogenic disorders. For example, abnormal interactions and misfolding of synaptic proteins in the nervous system are important pathogenic events resulting in neurodegeneration in various neurological disorders. These include Alzheimer's disease (AD), Parkinson's disease (PD), and dementia with Lewy bodies (DLB). In AD, misfolded amyloid beta peptide 1-42 (Abeta), a proteolytic product of amyloid precursor protein metabolism, accumulates in the neuronal endoplasmic reticulum and extracellularly as aggregates (i.e., plaques). The compositions of the present invention can be used to disturb such macromolecular complexes to thereby treat such disorders.

Methods of administration and generation of pharmaceutical compositions are described by, for example, Fingl, et al., (1975) "The Pharmacological Basis of Therapeutics", Ch. 1 p. 1.

The compositions of the present invention can be included in a diagnostic or therapeutic kits. For example, compositions of a specific disease can be packaged in a one or more containers with appropriate buffers and preservatives and used for diagnosis or for directing therapeutic treatment.

Thus, the ligand and coordinating moiety can be placed in one container and the coordinator molecule or ion can be placed in a second container. Preferably, the containers include a label. Suitable containers include, for example, bottles, vials, syringes, and test tubes. The containers may be formed from a variety of materials such as glass or plastic.

In addition, other additives such as stabilizers, buffers, blockers and the like may also be added.

A number of methods are known in the art for enhancing the immunogenic potential of antigens. For example, hapten carrier conjugation which involves cross-linking of the antigenic molecule (e.g. peptides) to larger carriers such as KLH, BSA thyroglobulin and ovalbumin is used to elevate the molecular size of the molecule, a parameter known to govern immunogenicity [see Harlow and Lane (1998) A laboratory manual Infra]. However, covalent cross-linking of the antigenic molecule leads to structural alterations therein, thereby limiting antigenic presentation. Non-covalent immobilization of the antigenic molecule to various substrates have been attempted to circumvent this problem [Sheibani Frazier (1998) BioTechniques 25:28]. Accordingly, compositions of the present invention may be used to mediate the same.

Thus, the present invention also envisages a method of enhancing immunogenicity of a molecule of interest using the compositions of the present invention. As used herein the term "immunogenicity" refers to the ability of a molecule to evoke an immune response (e.g. antibody response) within an organism.

The method is effected by contacting the molecule of interest with the composition of the present invention whereby the complex thus formed serves as an immunogen. Such a complex can be injected to an animal host to generate an immune response.

Thus, for example, to generate an antibody response, the above-described immunogenic composition is subcutaneously injected into the animal host (e.g. rabbit or mouse). Following 1-4 injections (i.e., boosts), serum is collected (about 14 weeks of first injection) and antibody titer is determined such as by using the above-described methods of analyte detection in samples, where the ligand is protein A for example. Alternatively or additionally, affinity chromatography or ELISA is effected.

It will be appreciated that the compositions of the present invention may have numerous other utilities, which are not distinctly described herein such as those utilities, which are attributed to affinity chromatography [see e.g. Wen-Chien and Kelvin (2004) Analytical Biochemistry 324:1-10].

It will be appreciated that the present invention may be adjusted for large scale (e.g., from 0.03 ml up to at least 100 ml) purification/depletion procedures which may be also accompanied by the use automatic means (e.g., robotics).

As used herein the term "about" refers to +/−10%.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683, 202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W.H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (19.85); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Synthesis of Non Covalent Multi Ligand Complexes Utilizing Chelator-Metal Complexes The ability of chelators to bind metals, with different specificities and affinities is well described in the literature. To generate the non-covalent multi ligand complex of the present invention, a linker, (of a desired length) is modified to bind a specific ligand, and a chelator to generate the following general structure of: ligand-linker-chelator.

Then, by the addition of an appropriate metal, a non-covalent multi-ligand complex should be formed. (FIG. 12)

For example, a hydroxamate (which is a known $Fe^{3+}$ chelator) derivative is synthesized (FIG. 13a) such that in the presence of $Fe^{3+}$ ions, a non-covalent multi-ligand complex is formed (FIG. 13b). A general synthetic pathway for modification of representative chelators with a general ligand is shown in FIG. 14. Such a synthesis can be similar to the one presented by Margherita et al., 1999 supra.

The utilization of chelators for the preparation of a non-covalent multi-ligand complex, may have an additional advantage which arises from the ability of some chelators to bind different metals with different stochiometries, as in the case of $[1,10\text{-phenanthroline}]_2$-$Cu^{2+}$, or $[1,10\text{-phenanthroline}]_3$—$Ru^{3+}$[Onfelt et al., (2000) Proc. Natl. Acad. Sci. USA 97:5708-5713].

This phenomenon can be utilized for formation of di (FIG. 15a) and tri (FIG. 15b) non-covalent multi-ligand complexes, utilizing the same: ligand—linker—chelator derivative.

Example 2

Synthesis of Non-Covalent Multi Ligand Complexes Utilizing Electron Rich-Poor Complexes Electron acceptors form molecular complexes readily with the "π excessive" heterocyclic indole ring system. Indole picric acid was the first complex of this type to be described nearly 130 years ago [Baeyer, and Caro, (1877) Ber. 10:1262] and the same electron acceptor was used a few years later to isolate indole from jasmine flower oil. Picric acid had since been used frequently for isolating and identifying indoles as complexes from reaction mixtures. Later, 1,3,5-trinitro benzene was introduced as a complexing agent and often used for the same purpose [Merchant, and Salagar, (1963) Current Sci. 32:18]. Other solid complexes of indoles have been prepared with electron acceptors such as: styphnic acid [Marion, L., and Oldfield, C. W., (1947) Cdn. J. Res. 25B 1], picryl halides [Triebs, W., (1961) Chem. Ber. 94:2142], 2,4,5,7-tetranitro-9-fluorenone [Hutzinger, O., and Jamieson, W. D., Anal. Biochem. (1970) 35, 351-358], and with 1-fluoro-2,4-dinitorbenzene and 1-chloro-2,4-dinitorbenzene [Elguero et al., (1967) Anals Real Soc. Espan. Fis. Quim. (Madrid) ser. B 63, 905 (1967); Wilshire, J. F. K., Australian J. Chem. 19, 1935 (1966)].

FIG. 16a, illustrates one example of a ligand—linker—electron poor (E. poor) derivative, and FIG. 16b, presents an example of an electron rich covalent trimer that could be used. It is expected, that by mixing together the trinitrobenzene (FIG. 16a) and the indole (FIG. 16b) derivatives, a multi-ligand complex will be formed (FIG. 16c). It will be appreciated that the reverse complex could be synthesized as well, i.e., a ligand derivative with an electron rich moiety, and an electron poor covalent trimer.]

A possible synthetic pathway for the preparation of the above ligand derivatives is shown in FIG. 17.

Synthetic peptides (or any peptide) containing Trp residues (or any other electron rich or poor moieties) may also be of use for the preparation of non-covalent multi ligand complexes. FIG. 18 shows an example of a synthetic peptide with four Trp residues (four electron rich moieties) that can be formed, a tetra-non-covalent-ligand in the presence of a ligand derivative modified with an electron poor moiety (trinitrobenzene).

Example 3

Synthesis of Non-Covalent Multi Ligand Complexes Utilizing a Combination of Electron Rich-Poor and Chelator-Metal Relationships One can combine the two complexing abilities as described in Examples 1 and 2 above, so as to form non-covalent multi ligand complexes. An example of the general structure of such a non-covalent multi ligand complex is shown in FIG. 19.

To this end, a chelator that is covalently bound to an electron poor moiety is desired. A synthetic pathway for generating such a combination is presented in FIG. 20.

For example, a chelator (e.g. catechol) that is capable to bind both to $M^{2+}$, and $M^{3+}$ metals, is capable in the presence of $M^{2+}$ and $M^{3+}$ metals, to form a non-covalent-di-ligand, (FIG. 21a), or a non-covalent-tri-ligand (FIG. 21b).

The presence of a peptide (or polypeptide) with a Trp residue (or any other electron rich residue) might lead to the formation of the structures shown in FIGS. 22a-b.

The combination of the two above binding relationships (chelator-metal together with electron rich-poor) may introduce additional advantages. For example, the ability to form non-covalent-multi-ligand-polymeric complexes. This may be achieved by synthesizing two chelators and an electron rich moiety between them (FIG. 23a). In the presence of a ligand—E. poor derivative the complex which is drawn in FIG. 23b is expected to form, which represents a Non-Covalent Polymer of ligands.

Once a dimer, trimer, tetramer etc. is formed, (by a ligand—chelator derivative for example) it may be desired to limit the freedom of motion of the above, in order to achieve more order. If the protein of interest has an electron rich moiety (such as Trp) that is accessible to a covalent di-electron-poor moiety (such as di-trinitrobnezene, TNB—TNB for example) then a complex might be formed between two non-covalent dimers. (FIG. 24). This may lead to the formation of ordered sheets of proteins and multi-ligands.

Example 4

The Desthiobiotin-Avidin Platform

Material and Methods
Synthesis of the desthiobiotinylated Protein A (DB-ProA) nonimmobilized ligand. Recombinant Protein A was modified with desthiobiotin N-Hydroxysuccinimidyl ester and yielded the modified Protein A derivative (DB-ProA) utilized in all purification experiments shown in FIGS. 27-29.

Precipitation and elution of rabbit IgG. Precipitation was carried out at 4° C. in a medium containing: 50 mM sodium phosphate at pH 8; 0.23 mg/mL of DB-ProA; 0.6 mg/mL rabbit IgG and cell lysate (either NRK, C2 or E. coli) in a total volume of 50 µL. A freshly prepared avidin solution (1.5 mg/mL final concentration) was added and a precipitate was formed. This was followed by a short spin at 14,000 RPM and removal of the supernatant. The pellet was resuspended once with 200 µL of 50 mM sodium phosphate buffer pH 8 and the supernatant discarded. To elute rabbit IgG, the pellet was further resuspended with 0.1M sodium citrate pH 2.5 or 3, with or without 0.9 M urea at 4° C. for 3-10 minutes in a total volume of 50 µL with or without gentle agitation. After an additional spin, the supernatant was neutralized with 1N NaOH or 3M Tris pH 9 and applied to the gel.

Regeneration of DB-ProA. Recovery of DB-ProA was achieved by incubating the pellets in 0.1M sodium citrate pH 3 and 5 mM of biotin at 4° C. for 10 minutes. Centrifugation at 14,000 RPM was performed and the supernatant was neutralized with 1N NaOH and loaded onto an acrylamide gel.

with the target protein and addition of the interconnecting entity (free avidin) generated a precipitate, composed primarily of the [modified ligand—target protein—avidin] multicomplex (FIG. 32c). The target protein is then eluted from the generated precipitate (i.e. pellet) under conditions that essentially do not dissociate the [modified ligand—avidin] multicomplex.

Since antibody purification is a major scientific and industrial need, the present study also tested the ability of the present approach to specifically capture and purify rabbit IgG from different cell lysates, utilizing DB-ProA as the ligand (FIGS. 27-28). The high purity (95-97%) and yield (80-86%) of the recovered IgG, demonstrates the feasibility of the present approach. The majority of impurities are excluded from the pellet in the precipitation step (FIG. 27a, lane 6, FIG. 27b, lane 6; FIG. 28 lane 7) prior to the washing step. This emphasizes the advantage of the present composition, which lacks any polymeric matrix onto which impurities would probably have been adsorbed non-specifically.

Similar precipitation and recovery behavior was observed with a desthiobiotinylated concanavalin A derivative (DB-ConA), used for the capture of glucose oxidase and porcine thyroglobulin (Table 1 below).

TABLE 1

Recovery yields and purity of the target proteins and the modified ligands

| Target protein | Desthiobiotinylated ligand | Recovery yield of target protein | Purity of target protein | Recovery yield of desthiobiotinylated ligand |
|---|---|---|---|---|
| Rabbit IgG | Protein A | 80-86% | 97% | 80% |
| Thyroglobulin | Concanavalin A | 70-75% | 95% | 85-89% |
| Glucose oxidase | Concanavalin A | 70-75% | 95% | 85-89% |

The effect of increased background contamination on the purification process. To study the effect of increased background contamination on the yield and purity of the purification process, identical amounts of rabbit IgG, avidin and DB-ProA were added to increasing concentrations of either BSA (FIG. 29a) or E. coli cell lysate (FIG. 29b). All pellets were washed once with identical volumes of fresh buffer (200 µL) regardless of their contamination background and the IgG was eluted. The eluted IgG solutions exhibited similar purity and yield (FIG. 29a lanes 2P-5P; FIG. 29b, lanes 3P-5P); BSA or E. coli cell lysate served as the background contamination.

Results

Specific precipitation and elution of target proteins. To demonstrate the selectively of the present approach, rabbit IgG was purified from bacterial cell lysates (FIGS. 27-28) by preparing a medium containing whole cell lysate, DB-ProA and rabbit IgG. Upon addition of avidin, a precipitate was generated and the resulting pellet was washed once with 200 µL of fresh buffer. The washed pellet was further incubated under eluting conditions (0.1M sodium citrate at pH 2.5-3, 4° C., for 5 minutes) and the supernatant of the resuspended pellet was applied to the gel after being neutralized to pH 7. The recovery yield of the IgG was 85% (FIG. 27a, lane 5; FIG. 27b, lane 5; FIG. 28, lane 6). Since no DB-ProA was observed by Coomassie staining in the eluted IgG (lane 6), the degree of leached DB-ProA was assessed by silver staining and was determined to be less than 1% (data not shown).

The modified ligands used in this study were desthiobiotinylated protein A (DB-ProA) and desthiobiotinylated concanavalin A (DB-ConA). Incubation of the modified ligand These consistent results with two distinct ligands indicate that other ligands may be utilized accordingly and lead to highly purified proteins with good recovery yields. Native protein A or concanavalin A lacking bound desthiobiotin did not lead to precipitation of the target proteins (data not shown). The use of non-immobilized ligands may raise the concern of ligand leaching. Nevertheless, leaching was not observed by Coomassie staining (FIG. 27a, lane 5, FIG. 27b lane 5, FIG. 28 lane 6). Therefore gels were visualized by silver staining and the degree of leached DB-ProA was less than 1% (data not shown). Since these values were obtained under eluting conditions at highly acidic conditions (pH 3), one would expect lower levels of leaching under milder eluting conditions. These observations suggest that target proteins can be eluted directly from the generated precipitates, while keeping the [modified ligand—avidin] macro-complex intact in the precipitate. This feature may be advantageous for large-scale protein purification, where obtaining a relatively pure protein in high concentrations by direct elution of the target protein from the pellet is a major advantage (2).

Furthermore, since all ligands utilized by the present approach are modified with a complexing entity (e.g. desthiobiotin, metal chelator) removal of minute amounts (<1%) of leached ligand can be accomplished by passing the sample containing primarily the eluted protein through an appropriate affinity column that would remove traces of leached modified ligand rather than the target protein. For example, a desthiobiotinylated-ligand could be removed from a solution containing the target protein by an avidin column.

Generally, as background contamination increases, greater volumes of buffer are needed to remove impurities that bind non-specifically to the polymeric matrix. Since no polymer matrix is present in the present composition, it is postulated that a major increase in the contamination background would not affect the purity of the eluted protein. Thus, to demonstrate such a phenomenon, all pellets must be washed with minimum and identical volume of buffer, regardless of their background contamination. The results shown in FIG. 29a, lanes 2P-5P; FIG. 29b, lanes 3P-5P, support this speculation and show that a 10 or 16 fold increase in the contamination background has no significant effect on either the purity or the yield of the target protein. Moreover, when pellets were not washed following formation and the IgG was eluted, high purity was obtained, thus providing additional supporting data to the "non-stickiness" nature of the precipitates. These results may imply that other contaminants (e.g. endotoxins, viruses, host DNA) could be excluded by the precipitation step, thereby reducing the number of purification steps in the downstream process.

In the preferred scenario, in which the target protein eluted from the pellet, regeneration of the modified ligand could be accomplished by a simple dialysis procedure. Since desthiobiotin has a lower association constant for biotin binding proteins ($K_a$~$5\times10^{13}$ $M^{-1}$ for streptavidin) than biotin ($K_a$~$1\times10^{15}$ $M^{-1}$), the pellet will dissociate upon addition of biotin (28). Dialysis will remove excess of unbound biotin, leaving the modified ligand (DB-ProA or DB-ConA) and the [avidin-(biotin)$_4$] complex in the dialysis container. This mixture (devoid of free biotin) could be used directly in the next batch, since the free [avidin-(biotin)$_4$] complex is blocked (essentially irreversibly) with 4 biotins, can not participate in network formation, and thus can be considered as an additional contaminant which will be excluded together with all impurities of the next cycle. This procedure was performed for the regeneration of both DB-ProA and DB-ConA (Table 1 above).

The non-immobilized state of the modified ligand might posses additional theoretical advantages which include higher yields of purified product due to faster and more efficient binding to the target protein in homogenous solutions where no additional steric hindrances are imposed by the polymeric matrix. The non-immobilized ligand is expected to be more available for binding, while in its immobilized state may also interact with the polymeric matrix making itself less available for binding. The measured affinity of the modified ligand should represent its affinity upon use, enabling easier judgment as to the most appropriate modified ligand derivative to be utilized in a particular purification process. It has been argued that once a ligand is immobilized its affinity may be reduced by up to a factor of 1000 (30). Such a concern is not relevant to the present approach since no ligand immobilization is required; the amount of added modified ligand to the medium is (theoretically) not limited, whereas affinity columns are characterized by their specific capacity. Therefore, more protein can be purified per batch. Additional benefits deriving from the non-immobilized state may result in higher purity of the end product due to the absence of a polymeric matrix onto which impurities can adsorb; implementation of harsh sanitizing procedures without risking ligand functionality (i.e. the modified ligand can be removed from any instrumentation prior to sanitation); while a dramatic volume reduction within a single precipitation step would enable further purification manipulations with lab-scale machinery.

It will be appreciated that the present approach is fundamentally different from immunoprecipitation. In the latter, antibody-antigen complexes are removed from solution in the presence of an insoluble form of an antibody binding protein such as protein A or an immobilized second antibody, while in the present approach all components (i.e. the modified ligand and the interconnecting entity) are water soluble and are not immobilized.

Essentially, the approach does not introduce a new chemical principle but rather a different chemical architecture which could utilize any ligand, provided that specificity and affinity as well as uniformity are preserved following ligand modification. The possibility of generating equivalent precipitates utilizing other types of modified ligands (e.g. ligand-chelator, ligand-antigen, ligand-nucleotide sequence, (FIG. 32c) emphasizes the wide applicability of the present approach. Furthermore, the [DB-ProA—avidin] complex may serve as a "core complex" for additional applications such as positive/negative cell selection—target cells could be purified (or depleted) with the above "core complex" and an antibody targeted at an epitope on the target cell (FIG. 33a) or depletion of viruses via use of an antibody specific to the virus (FIG. 33b).

Example 5

The Metal-Chelator Platform

Materials and Methods

Synthesis of the catechol Protein A derivative (ProA-CAT) nonimmobilized ligand. Recombinant Protein A was modified a N-Hydroxysuccinimidyl ester derivative of the strong metal catechol (catechol-NHS) and yielded the modified Protein A derivative (ProA-CAT) utilized in all purification experiments shown in FIG. 30.

Purification of rabbit IgG from *E. coli* cell lysate utilizing ProA-CAT and Fe3+ ions (FIGS. 30-31). ProA-CAT (0.46 mg/ml) was added to the *E. coli* cell lysate (first dialyzed to remove 20 mM imidazole) containing 0.5 mg/ml rabbit IgG, 10 mM NaPi, 400 mM NaCl at pH 7. Following 3-5 minutes of incubation at 4° C., 3 mM of $Fe^{3+}$ ions were added to initiate precipitation of the [ProA-CAT:IgG] soluble complex (FIG. 31b). Two hundred mM of imidazole were added to suppress non-specific interactions between the generated macro-complexes and impurities possessing weak chelating residues (e.g. His, Cys). Following centrifugation at 14,000 RPM, the supernatant primarily contained impurities with no evidence of ProA-CAT and the IgG (FIG. 30a, lane 7). The pellet (containing the complexed IgG) was then washed once with 100 μl of fresh buffer containing 20 mM NaPi pH 7, to remove traces of impurities.

Rabbit IgG was eluted from the washed pellet by resuspending it for 3-5 minutes at 4° C. in 0.4 M Gly and 0.3 M His at pH 3. Following centrifugation at 14,000 RPM, the supernatant was removed and neutralized; analysis thereof revealed presence of the target IgG. The average recovery yield was 80% with a purity greater than 95% as determined via densitometry (FIG. 30a, lane 6). Similar yield and purity results (yield: 71%; purity>95%) were obtained with bovine IgG, thus, demonstrating the applicability of the present approach in purifying targets with lower affinity toward protein A.

The effect of increased background contamination on the purification process. Generally, greater volumes of buffer are required to remove impurities that adsorb non-specifically to polymeric matrixes in chromatographic columns as the contamination increases. Since no polymeric matrixes are utilized by the present approach, it was postulated that an increase in the background contamination should not affect the purity of the recovered IgG. To demonstrate such a phenomenon, constant concentration of rabbit IgG and ProA- CAT were added to increasing concentrations of E. coli cell lysate (FIG. 30b lanes 3-5) and all generated pellets were washed once with a minute volume (100 µl) of buffer regardless of their contamination background. While the recovery yield of the IgG decreased with increased contamination background (~80% to ~70-75%), the purity (>95%) was similar (FIG. 30b, lanes 3P-5P), thus emphasizing the advantage of a purification approach lacking a polymeric component.

Regeneration of ProA-CAT. ProA-CAT was regenerated without any chromatographic process at neutral pH in the presence of strong metal chelators such as EDTA and catechol. It was assumed that these chelators will compete with the ProA-CAT on the complexed $Fe^{3+}$ ions, thereby leading to dissolution of the [ProA-CAT:$Fe^{3+}$] macro-complex (FIG. 31d). Indeed, a short incubation at 4° C. in the presence of 50 mM NaPi pH=7, 100 mM EDTA, 50 mM catechol and 10% ethylene glycol lead to quantitative dissolution of the pellet and regeneration of the ProA-CAT in 75-85% yield (data not shown). The free and complexed chelators, together with all other reagents, could then be dialyzed, enabling the reuse of the ProA-CAT.

Thus, a general platform for antibody purification utilizing free nonimmobilized protein A modified with the strong metal chelator catechol (ProA-CAT) and $Fe^{3+}$ ions is presented. The mechanism of purification requires formation and precipitation of macro-complexes composed of: [ProA-CAT:IgG:$Fe^{3+}$]. Target IgGs are eluted from the precipitates at pH 3 in high yields (71-80%) and high purity (>95%), without dissociating the [ProA-CAT:$Fe^{3+}$] insoluble macro-complex.

Highly purified antibody preparations represent a major scientific and industrial need. In a recent study (34) the present inventors presented a novel purification approach, utilizing free nonimmobilized desthiobiotinylated ligands (e.g., protein A; concanavalin A) and free avidin. The nonimmobilized state of the ligand circumvents the need for immobilizing ligands to polymeric supports hence, polymers are excluded from the process and purification is accomplished without chromatographic columns. This study further demonstrated the implementation of the present approach on a novel, more challenging platform, the Metal: Chelator platform. Protein A, a 42 kDa factor produced by several stains of Staphylococcus aureus, which binds specifically to the Fc region of different classes of immunoglobulins (35), was modified with an active ester derivative of the strong metal chelator catechol, catechol-NHS according to Bayer et al. (36). The modified protein A (ProA-CAT) serves as the nonimmobilized ligand and is used for purification of rabbit and bovine IgGs from E. coli cell lysate.

The mechanism of purification of this aspect of the present approach requires three successive steps:
 (i) Incubation of the modified ligand (ProA-CAT) with the target IgG to initiate specific binding and formation of the: [ProA-CAT:IgG] soluble complex (FIG. 31a).
 (ii) Precipitation of the [ProA-CAT:IgG] complex upon addition of $Fe^{3+}$ ions which generate insoluble macro-complexes composed of: [ProA-CAT:IgG:$Fe^{3+}$], whereas impurities are left in the supernatant and are discarded by centrifugation (FIG. 31b).
 (iii) Elution of the IgG from the [ProA-CAT:IgG:Fe 3+] insoluble macro-complex (i.e. pellet) under conditions which essentially do not dissociate the [ProA-CAT:$Fe^{3+}$] macro-complex, thus leading to a simple and fast recovery of the target IgG (FIG. 31c).

Catechol was chosen as the preferred chelator since it: (a) exhibits high affinity toward diverse transition metals (37), therefore enabling the use of a variety of transition metals; (b) requires three independent catechol moieties to chelate a single $Fe^{3+}$ ion, thereby increasing the possibility of interconnecting adjacent [ProA-CAT:IgG] soluble complexes; (c) was expected to retain its chelating ability even at acidic conditions (pH 3) due to the absence of basic atoms (e.g. nitrogen) required for complex formation. A nitrogen atom (if existed) would be protonated at low pH and not be available for chelating $Fe^{3+}$ ions.

Several independent results imply that $Fe^{3+}$ ions function as the interconnecting entity: (a) precipitation of the [ProA-CAT:IgG] complex was abolished in the presence of free chelators [e.g., EDTA, catechol, desferal (a specific $Fe^{3+}$ chelator)]; (b) other transition metals (e.g., $Cu^{2+}$, $Zn^{2+}$, $Mg^{2+}$, $Ni^{2+}$) possessing lower affinity toward catechol did not lead to substantial precipitation under identical conditions; and (c) regeneration of ProA-CAT at physiological pH was accomplished only in the presence of strong metal chelators.

In conclusion, the simple precipitation approach presented herein eliminates the need for sophisticated instrumentation (e.g. HPLC) and provides a highly efficient approach for large scale purification of target molecules/cells. In addition, it provides a fast and simple approach and thus would be advantageous in purification of targets that tend to denature rapidly while being highly amenable to scaling by simply increasing the concentration of the modified ligand.

In addition, the present approach enables efficient capture of low abundance targets by simply increasing the modified ligand concentration (being a reagent) without significantly diluting the sample, thereby increasing the rate of complex formation (Rate=k [Free ligand] [Target]). Targets are not diluted within the process (unlike column chromatography) and are eluted into small volumes of elution buffer, resulting in concentrated preparations which may be used directly for crystallization trials. The present approach may be applicable to positive or negative cell selection, virus depletion and immunoprecipitation via epitope capture by a free antibody.

Furthermore, all presently known chromatographic and precipitation techniques require covalent attachment between the ligand and a polymeric support, while the present approach uses ligands in their free non-immobilized state. The use of free ligands circumvents the need for immobilizing ligands to polymers and would exclude polymers from the purification process. FIG. 32 illustrates the differences in chemical architecture between well established approaches (e.g. affinity chromatography, affinity precipitation) and the present approach (labeled as "affinity sinking"), in which, precipitation of the target protein requires two water soluble entities: a modified ligand and an interconnecting entity.

Example 6

Synthesis of the Multivalent Nonimmobilized Ovalbumin Ligand

Highly purified ovalbumin (Sigma A5503) was modified with desthiobiotin N-Hydroxysuccinimidyl ester and 6-[Fluorescein-5(6)-carboxamido]hexanoic acid N-hydroxysuccinimide ester (Sigma—F1756) in the following stoichiometric ratio: Ovalbumin:Desthiobiotin:Fluorescein, 1:22:12. Modification was carried out in 0.1M NaHCO3 pH 8.5 for 4 hours at room temperature followed by extensive dialysis to remove excess of free desthiobiotin and fluorescein. The modified ovalbumin serves as the multi-nonimmobilized ligand of the present invention.

Purification of Anti-Fluorescein mAb

Purification of anti-Fluorescein mAb was carried out at 4° C. in a medium containing: 10-20 mM sodium phosphate at pH 7; 0.5 mg/ml of the modified ovalbumin; 1.2 mg/ml of total protein containing ~0.1 mg/ml of IgG1 anti-FITC mAb in a total volume of 50 μL. After a short incubation with the modified ovalbumin, a freshly prepared avidin solution (1.5 mg/ml final concentration) was added and a precipitate was formed. This was followed by a short spin at 14K and removal of the supernatant containing the majority of impurities. The content of the supernatant after the addition of avidin is shown in lane 5 of FIG. 37. To demonstrate specific binding between the anti-Fluoresein mAb and the fluorescein immobilized on the ovalbumin, precipitation was performed in the presence of excess free Fluorescein. The presence of the band corresponding to the mAb in lane 6 of FIG. 37 (absent in lane 5) provides direct evidence to a competitive inhibition between of the free and immobilized fluoroescein on the target mAb. The pellet was resuspended once with 200 μL of 20 mM sodium phosphate buffer pH 7 and the supernatant containing traces of impurities was discarded. To elute anti-FITC mAb, the pellet was further resuspended with 20 mM sodium phosphate buffer pH 7 and 5 mM of free Fluorescein at 4° C. for 3-10 minutes in a total volume of 50 μL with or without gentle agitation. After an additional spin, the supernatant containing the recovered (i.e. eluted) mAb was neutralized and applied on the gel (lane 7, FIG. 37). Similar recovery the anti-Flourescein mAb was obtained under acidic conditions (0.1M sodium citrate) data not shown. An identical elution procedure was performed on the pellet generated in the presence of free Flourescein. Since no recovered mAb was observed (lane 8, FIG. 37) it imply that most of the mAb was already excluded from the pellet in the precipitation step. The difference in migration between the native (lane 1, FIG. 37) and modified (lane 2, FIG. 37) ovalbumin reflect the degree of modification.

Regeneration of the Modified Ovalbumin

Recovery of modified ovalbumin was achieved by incubating the pellets in 0.1M sodium citrate pH 3 and 5 mM of biotin at 4° C. for 10 minutes. A spin at 14K was performed and the supernatant was neutralized and applied to the gel (data not shown).

Example 7

Generation of Modified Ligand Networks

Better eluting efficiency may be accomplished via use of networks/matrices which have "larger holes". One approach for generation of such networks can be effected by initiating a precipitation process in the presence of free biotin which would occupy some of the binding sites of avidin and avoid maximum interconnections between modified ligands. (e.g. desthiobiotinylated ligand). Similarly, prior incubation of avidin with biotin would be applicable as well.

The upper limit concentration of biotin which does not alter specific precipitation efficiency was identified by the present inventors and further utilized to evaluate whether faster and more efficient elution is achieved via use of "defective" networks. Porcine thyroglobuline was incubated with desthiobiotinylated concanavalin A (concanavalin A is a known ligand for porcine thyroglobuline) and free D-biotin. After a short incubation free avidin was added and a precipitate was formed thereby forming a defective network. The same procedure was employed in the absence of D-biotin thereby forming a regular, non-defective network. The results suggest faster elution of the target protein (porcine thyroglobuline) from the defective network. (see FIG. 39).

Example 8

Precipitation of Immuno-Labeled Molecules

Materials and Methods

Desthiobiotinylated Protein G (DB-ProG) was synthesized according to DB-ProA in Example 4 and incubated at indicated times at 4° C. in a medium containing: normal rat kidney (NRK) cell lysate, 0.0135 mg/ml HA-LacZ (i.e. Target antigen), 0.008 mg/ml anti-HA mAb (Sigma H9658), 0.019 mg/ml DB-ProG; 20 mM NaPi at pH 7, in a total volume of 600 μL.

A freshly prepared avidin solution was then added to the medium (0.125 mg/ml final concentration) and a precipitate was formed. The pellet was separated from the supernatant (containing most of the impurities) by a short centrifugation at 14K and removal of the supernatant. The pellet could then be resuspended with fresh buffer (e.g. 20 mM NaPi pH 7) to remove traces of impurities. The Target (HA-LacZ) was eluted from the washed (or unwashed) pellet by further resuspending it in 0.1M Glycine pH 2.5 at 4° C. for 3-10 minutes in a total volume of 50 μL with or without gentle agitation. After an additional spin, the supernatant was neutralized with 1N NaOH or 3M Tris pH 9 and applied to the gel (see the gel below).

Results are shown in FIGS. 40a-b. Altogether a dramatic yield of the HA-Lac-Z was observed using the above teachings. These yields are significantly higher than the yield obtained with commercially available kits.

These results strongly support the use of antibody binding moieties attached to a coordinating moiety for the precipitation (recovery or depletion) of immuno-labeled molecules (as presented here), cells and viruses as desired.

Example 9

Positive and Negative Cell Selection

Materials and Methods

Materials—Spermidine, Pentaethylenehaxamine and Poly-Asp were from Sigma-Aldrich. Mouse purified anti-human CD3 (clone OKT3), mouse purified and mouse purified anti-human CD235a (clone HIR2) were from e-bioscience. The anti-human CD28 (clone 204-12) was from SouthernBiotech; Fluorescein (FITC)-conjugated mouse anti-human CD3 (clone UCHT1) was from IQ products; cell proliferation kit (XTT assay) was from Biological industries, Israel.

Cell lines—The K-562 CML-derived and Jurkat T-cell, human leukemia lines were grown at 37° C., 5% $CO_2$ and cultured in RPMI (Biological industries, Israel) medium containing 10% FCS, 2 mM L-glutamine, 1% (v/v) non-essential amino acids solution, 100 units/ml penicillin and 0.1 mg/ml streptomycin. Jurkat cells constitutively expressing eGFP (Jurkat-GFP) were generated by electroporation and antibiotic selection.

Synthesis of the Desthiobiotinylated-Protein A—Desthiobiotinylated-Protein A was synthesized according to Patchornik and Albeck 2005, and used throughout this study.

Depletion of Jurkat-GFP cells from K-562 cells (see schematic illustration in FIGS. 41A-D.

Into a mixture of Jurkat cells stably expressing eGFP (Jurkat-GFP) and K-562 (Chronic myelogenous leukemia) in a roughly 1:1 stoichiometric ratio in PBS and 2% FCS, two specific antibodies (anti-CD3, anti-CD28, e.g., 0.9 ng/ml, 0.77 ngr/ml respectively) directed toward two distinct epitopes on Jurkat-GFP cells were added together with the modified-Protein A (i.e. desthiobiotinylated-Protein A, e.g. 0.06 mg/ml) and incubated for 5 min. at room temperature with gentle shaking and/or rotation. To precipitate labeled Jurkat-GFP cells bound to the [mAb's-desthiobiotinylated Protein A] complex, free streptavidin was added (e.g. 0.57 mg/ml) with constant vortexing. Additional vortex (e.g., 5-15 seconds) was applied after streptavidin addition and the mixture was then subjected to constant rotation until turbidity was observed. After the rotation step, the tube was left for additional period of time to promote sedimentation of the precipitate at the bottom of the tube. Aliquots from the upper medium were filtered using a nylon mesh (e.g. having an average pore size of 30 μm). 1 mM of biotin was then added to the medium to dissolve the [desthiobiotinylated-Protein A:streptavidin] macro-complexes present in the medium. A short spin enabled the removal of reagents (e.g. excess of biotin, desthiobiotinylated Protein A, streptavidin:biotin complex) and cells were resuspended in PBS and analyzed by FACS FIG. 41E-H show that the supernatant is enriched with K-562 cells when specific antibodies are present (G-H) whereas in their absence the stoichiometric ratio is not affected (E-F).

Characterization and Dissolution of: [Desthiobiotinylated-ProteinA:Streptavidin] Aggregates Analysis of the supernatant at the end of the depletion process revealed the presence of aggregates in addition to cells (see arrows in FIGS. 42A-B). These aggregates were shown to be composed of the desthiobiotinylated protein A and streptavidin since they were not observed when biotin was present in the medium (FIG. 42B). The mechanism of dissolution is based on the higher affinity of biotin towards streptavidin relative to desthiobiotin ($K_a \sim 1 \times 10^{15}$ $M^{-1}$ and $K_a \sim 5 \times 10^{13}$ $M^{-1}$ respectively, MÜller et al., 1993) and the ability of biotin to displace desthiobiotin at neutral pH (Hirsch et al., 2002). Therefore, when biotin is present in the medium it competes with desthiobiotin on binding to streptavidin and dissociates the aggregate at physiological pH. This dissolution step was applied at the end of all selection experiments and prior to the FACS analysis.

Depletion of Jurkat Cells from THP1—FITC Cells (FIG. 43a)

THP1 cells, first modified with 0.25 M of FITC according to (Aplin and Hughes., 1981) were mixed with Jurkat cells. After a short centrifugation step (800 g, 4 min) the two cell populations were resuspended in a total volume of 0.78 ml of PBS containing 2% FCS and a mixture of two mAb's: anti-CD3 (0.9 ng/ml) and anti-CD28 (0.77 ng/ml) and the desthiobiotinylated-Protein A (0.06 mg/ml). These were gently rotated for 5 min. at room temperature. Upon addition of streptavidin (0.57 mg/ml) and further rotation (~5 min.), a precipitate was observed. The tube was left for an additional period of time to promote sedimentation of the precipitate at the bottom of the tube. Cells present in the supernatant were filtered using a 30 μm nylon mesh and 1 mM of biotin was added to the filtrated cells to dissolve remaining complexes comprising of the desthiobiotinylated-Protein A and streptavidin. An additional centrifugation step (e.g. 800 g, 4 min) was applied and was followed by resuspending cells in PBS containing 2% FCS. The purity of the enriched medium/supernatant containing the THP1-FITC labeled cells was assessed by FACS.

As shown in FIG. 43A to distinct between different molecular mass complexes, a filtration step is used. The effect of filtration on the purity of the isolated cells is presented in FIG. 43A.

Positive Cell Selection of Jurkat Cells from THP1-FITC Cells

The protocol for positive selection is similar to that of negative selection (i.e. depletion). In positive selection, upon formation of the precipitate containing the target cells, the supernatant is removed and the precipitate is carefully washed with PBS to further exclude unwanted cells. The washed precipitate is then applied on a 30 um nylon mesh for further washing (if required). The washed precipitate (either on top of the nylon mesh/or in the tube) is incubated in the presence of 1 mM biotin in PBS to dissolve residual complexes comprising of the desthiobiotinylated-Protein A and streptavidin. Cells are analyzed by FACS.

Thus, contrary to negative selection, where the supernatant is enriched with the target cells, in positive cell selection, target cells are first precipitated (FIG. 41D) and then preferably, released from the precipitate for further manipulations. FIG. 43B demonstrates how Jurkat cells can be positively selected from their mixture with THP1-FITC cells.

Determination of Cells Viability

The relative number of viable cells in a given culture was determined using the XTT commercial assay (Biological industries, Israel) according to manifacturer's instructions. The toxicity effect of different reagents used in the depletion protocols above (e.g., mAb's, desthiobiotinylated-Protein A, Streptavidin, Biotin alone or in combination) was assessed. No significant effect on the viability of Jurkat cells-GFP was observed (see FIG. 44).

Example 10

Use of Streptavidin for Cell Precipitation

While using the above teachings of the present invention, the present inventors have attempted to use avidin for cell precipitation.

It soon became apparent that cells e.g., Jurkat-GFP and K-562 precipitate, when a mixture of a specific antibody, the modified-Protein A and avidin were present (FIG. 45A). Even more strikingly, this observation repeated itself in the absence of an antibody (FIG. 45B).

The quantitative precipitation observed in the absence of an antibody suggested that this finding could be attributed to either: a. Non-specific binding of the cells to the generated [modified Protein A:avidin] macro-complex. b. Entrapment of the cells during macro-complex formation.

Since plasma membranes are negatively charged at physiological pH and avidin is positively charged (due to its high pI value, pI=10.5) and is a major component of the macro-complex, it was suggested that strong electrostatic interactions between cell membrane components (e.g., phospholipids) and positively charged residues within avidin (e.g. Lys, Arg) may have generated multiple electrostatic interactions which resulted in the quantitative precipitation observed (FIG. 46).

To test this hypothesis, three independent experiments were designed. The results of these assays are summarized infra. A Use of a medium containing poly-amines such as: pentaethylenehexamine or Spermidine (1-2% w/v) caused of a significant reduction in non-specific precipitation of cells (FIG. 47A). These results imply, that the binding of the positively charged polyamines to the negatively charged cell membrane compete with the positively charged residues of avidin thereby, abolishing the non-specific precipitation. B. Similarly, the presence of a negatively charged entity such as: poly-Asp acid (with an average Mw of 5-15 kDa, 1-2% w/v) possessing a net negative charge at physiological pH, binds the positively charged avidin residues (e.g., Lys), and compete binding to the negative cell membrane (FIG. 47B). C. The replacement of avidin with streptavidin may represent the most direct experimental evidence. Avidin and streptavidin differ significantly in their pI values (10-10.5 vs. 5-6 respectively), therefore, formation of a macro-complex composed of streptavidin would possess a net positive charge at physiological pH, and therefore, non-specific precipitation would be circumvented (FIG. 47C).

The results of these assays are presented in Table 2 below.

TABLE 2

|  | Modified protein A | Avidin | Poly-amine | Poly-Asp | streptAvidin | Cell precipitation (%) |
|---|---|---|---|---|---|---|
| Control | + | + | − | − | − | 100 |
| A | + | + | + | − | − | 0 |
| B | + | + | − | + | − | 20-25 |
| C | + | − | − | − | + | 0 |

Understanding the molecular mechanism promoting non-specific precipitation paved the way to evaluate the specificity of the approach. Jurkat cells (see above Example 9), stably expressing eGFP (Jurkat-GFP) were resuspended in PBS, and were efficiently precipitated in the presence of two specific antibodies: anti-CD3 and anti-CD28 (FIG. 48D). The absence of specific antibodies, or the presence of a non-specific one (e.g., anti-glycophorin) did not result in significant precipitation (FIGS. 48B-C). These results show that only when an appropriate antibody is added together with the modified-Protein A and free streptavidin, an efficient process of cell specific precipitation is generated.

Example 11

Dynamic Incubation Promotes Precipitation

The present inventors have analyzed the effect of dynamic incubation following the addition of streptavidin. It has been surprisingly bnoted, that by applying dynamic conditions the formation of a precipitate is promoted and aggregates are obtained within short incubation times. When no such movement is applied (i.e., rotation or agitation of any kind), the precipitate is generated but with less efficiency and over a longer time scale. Thus for example, following a short rotation/movement step (i.e., 5 min.), the tube was left for additional 3-5 minutes without any movement, so as to allow macro-complexes to precipitate at the bottom of the tube. These technical manipulations were performed throughout this study and were found essential for an efficient positive and negative cell selection.

Example 12

Cell Separation Using Centrifugation

A workable alternative to filtration is centrifugation (e.g., differential centrifugation, density gradient centrifugation, rate zonal centrifugation). The following two examples (FIGS. 49 and 50) demonstrate how T cells can be depleted or selected from peripheral blood mononuclear cells (PBMC). Generally, after all reagents were added to the medium (e.g., desthiobiotinylated-Protein A, mAb, and streptavidin) and some type of rotation/agitation was applied, samples were subjected to centrifugation in the presence of the polysaccharide: Ficoll. Other reagents known to separate cells according to their density and or size (colloidal silica (e.g., Percoll), Iodinated media (e.g., Nycondenz), Sugars (e.g., Sucrose), Ficoll PM 70, Ficoll PM 400) may be used accordingly.

Depletion of T Cells from PBMC FIG. 49

Lymphocytes were separated from total blood using Ficoll Paque Premium. Into the resuspended cells in PBS the anti-CD3 mAb and the desthiobiotinylated-Protein A were added and incubated for 5 min. at room temperature with gentle rotation. A freshly prepared streptavidin solution was slowly added to the medium with constant vortexing (additional vortexing was generally further performed). To the resulting medium, a Ficoll solution was gently added at the bottom of the tube and a short centrifugation step (e.g., 800 g, 7 min.) was applied. After centrifugation, the PBS phase and the upper part of the Ficoll phase were collected and biotin was added to dissociate all macro-complexes/aggregates in the system, generated by the [desthiobiotinylated-Protein A:Streptavidin] macro-complex. Excess of biotin and other reagents were removed by centrifugation (e.g., 1000 g, 2 min.); resuspended cells were stained with anti CD3-FITC (IQ products) and analyzed by FACS. The results shown in FIG. 50 enequivocally show that the majority of T cells were removed and that a highly purified cell mixture containing B and NK cells was obtained.

Positive Cell Selection T Cells from PBMC (FIG. 50)

The protocol for positive selection is similar to the one described above for depletion of T cells from PBMC. In positive selection, after macro-complex formation and centrifugation with Ficoll, the precipitated cells (i.e., pellets) were resuspended in PBS and biotin. An additional centrifugation step was applied to remove unwanted reagents and cells were stained with anti CD3-FITC (IQ products) prior to their FACS analysis. The results demonstrate, that the initial T cell population was enriched in the pellet (Initial=80%, Final=94%) thus, demonstrating the specificity and applicability of the process.

The present approach for cell separation provides several advantages over current methodologies (e.g., the magnetic bead technology) as follows:

a. A fast selection process—the present teachings enabled cell selection within 25-30 minutes, whereas protocols based on the magnetic bead technology generally require 75-90 minutes.

b. The combination of a fast process and the absence of any polymeric particles (either magnetic or non-magnetic), imply that undesired activation/activation during cell isolation may be significantly suppressed or abolished.

c. The fast, simple and mild dissolution process, pave the way for isolation of sub-cell populations as is illustrated in FIG. 51.

Example 13

Molecular Purification Using Composite Ligands Having Two or More Target Recognition Moieties The composite ligand approach is effected to provide a ligand with enhanced avidity by attaching target recognition moieties to a molecular scaffold/platform. Thus, the ligand is a composite (synthetic or natural) entity comprising a basically inert soluble scaffold/platform having active groups (e.g., amines) for chemically attaching the target recognition moieties as well as the target recognition moieties attached thereto. In accordance with an exemplary embodiment of the present invention the scaffold is albumin and the like e.g., BSA, HSA, ovalbumin. The target recognition moieties can be homogeneous (i.e., the same) or heterogeneous (i.e., not the same) exhibiting high affinity (e.g. $K_D<10^{-5}$) binding to the target molecule of interest and as such the two are capable of specifically interacting. Binding of the target can be directly or indirectly (e.g., mediated by a metal). The composite ligand of the present invention is chemically bound to coordinating moieties.

Figure 52:
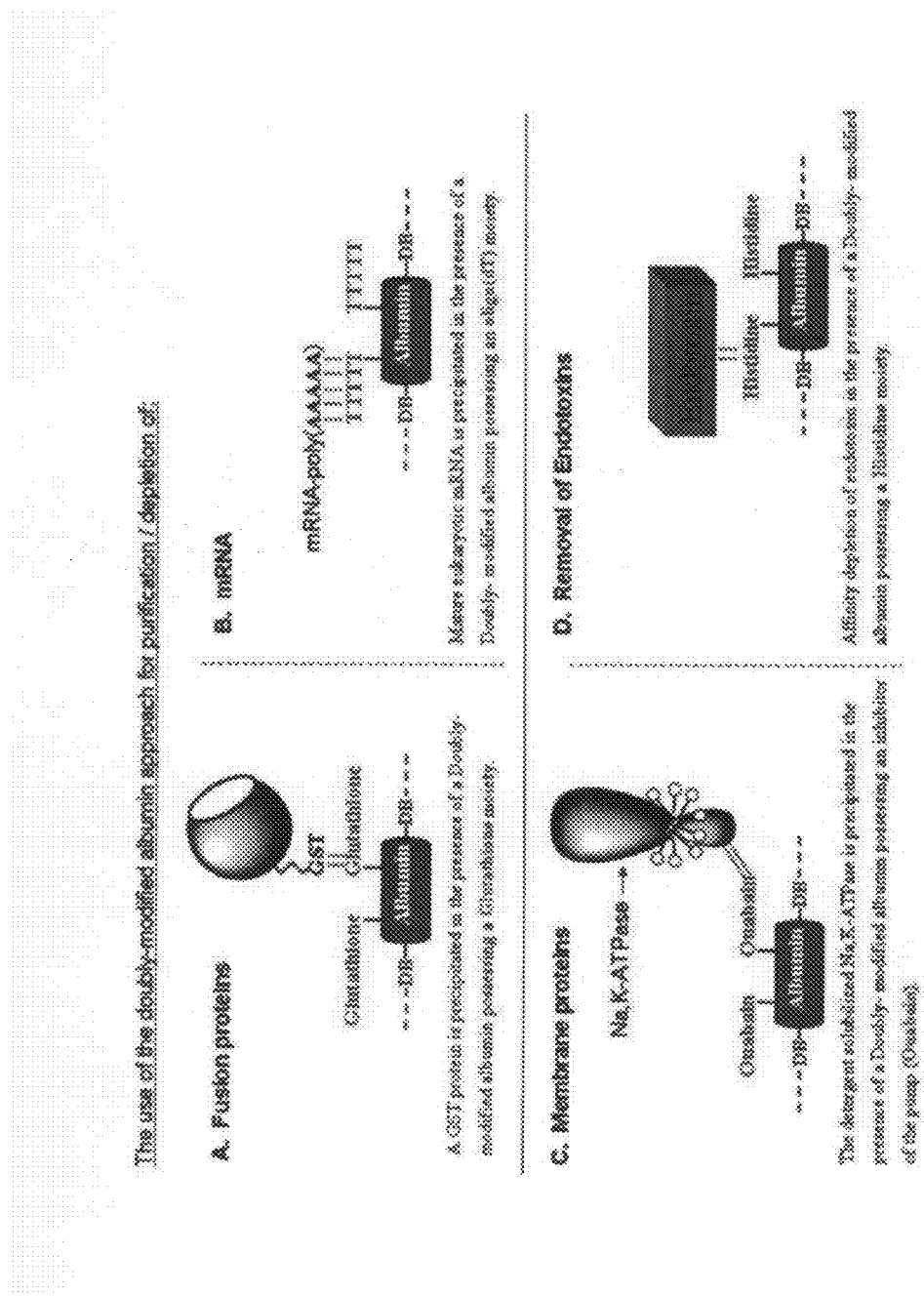

The following provides exemplary application embodiments which can be used in accordance with the composite ligand teachings of the present invention.

a. GST-proteins with a: [Desthiobiotin-Albumin-Glutathione] conjugate (FIG. 52A).

b. Poly($A^+$) mRNA with a: [Desthiobiotin-Albumin-oligo(dT)] conjugate (FIG. 52B).

c. Membrane proteins (e.g., Na,K-ATPase) with a: [Desthiobiotin-Albumin-Ouabain] conjugate (FIG. 52C).

d. Depletion of pyrogens with a: [Desthiobiotin-Albumin-Histidine] conjugate (FIG. 52D).

e. Purification of ribonucleosides with a [Desthiobiotin-Albumin-Boronic acid] conjugate.

f. Isolation of C-reactive protein binding with a [Desthiobiotin-Albumin-p-Aminophenyl phosphoryl choline] conjugate.

g. Isolation of cathepsin D, rennin, pepsin, bacterial aspartic proteinases and HIV proteases with a [Desthiobiotin-Albumin-Pepstatin] conjugate.

h. Purification of nanoparticulates (e.g., protein inclusion bodies as enhanced-expression vehicles, Virus like particles as putative vaccine cores) or plasmid DNA. Plasmid DNA can be isolated with the following general conjugate:

[Desthiobiotin/Catechol:Albumin/or any Other Soluble Protein or Soluble Entity Capable of being Modified:any Moiety Capable of Interacting with Plasmids].

Sequence specific interaction on an oligonucleotide capable of forming a triple helix with the plasmid:

[Desthiobiotin-Albumin—Sequence Specific Oligonucleotide]

Binding to the plasmid via a zinc finger protein recognizing a specific nucleotide sequence which is either naturally present on is inserted to the plasmid.

[Desthiobiotin-Albumin—Zinc Finger Protein]

Utilization of the LacI protein as a ligand:

[Desthiobiotin-Albumin—LacI]

i. For Proteomic applications, simultaneous removal of high abundance proteins (e.g. Albumin, IgG's) from samples prior to their 2D gel electrophoresis analysis, utilizing a mixture of:

[Desthiobiotin-Albumin-Cibacron Blue]+[Desthiobiotinylated-Protein A] conjugates.

Example 14

Purification of His-Tag Molecules with a Double Modified Albumin

Specific Example for the Composite Ligand Approach

One of the most widely used methods for protein isolation is immobilized metal ion affinity chromatography (IMAC) first introduced by Porath et al in 1975 [Nature (1975), 258, 598]. The approach provides a single-step purification process for fusion proteins containing an engineered His-tag, generally attached to the 5' or 3' end of the target gene. The engineered His-tagged protein is applied on a column comprising a non-soluble resin (e.g. agarose, sepharose) first modified with a metal chelator (e.g. IDA, NTA, TED) which is capable of immobilizing different transition metals such as: Ni2+, Co2+, Cu2+, Zn2+ (Porath and Olin, 1983; Porath, 1988; Sulkowski, 1989). The Immobilized metal, serves as a ligand for certain amino acid residues (e.g. Histidine, Cysteine, Tryptohan, Tyrosine) by reversibly binding them. The most common matrix for IMAC purification is iminodiacetic acid (IDA) and Ni2+ serves as the most widely used metal.

Figure 53C:
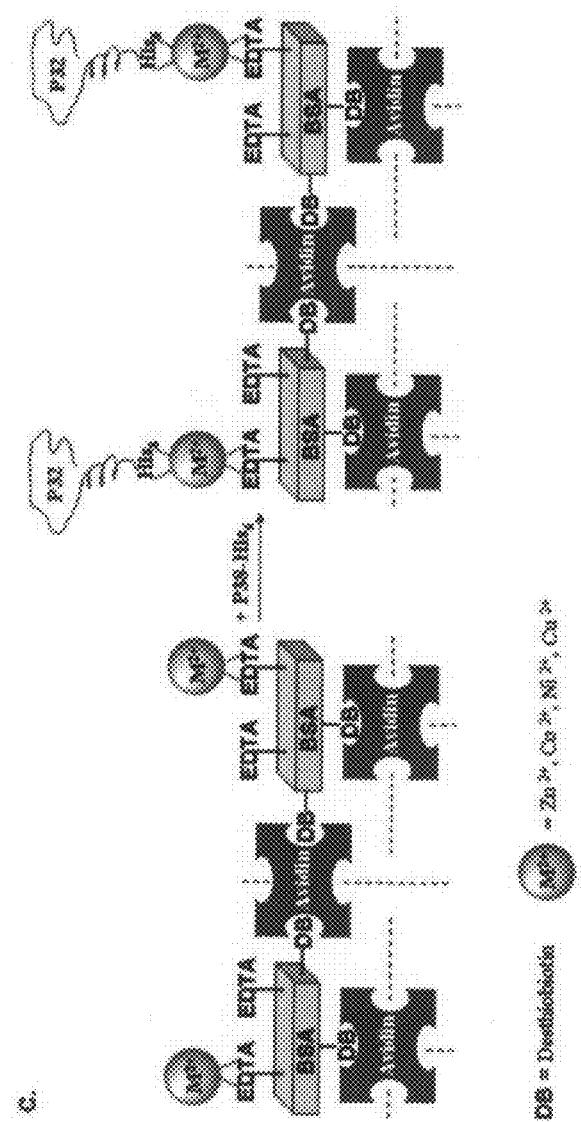

The presented approach is a continuation of our latest study [Patchornik, 2007, J. Biochem. Biophys. Methods, 70 (2007) 671-673] demonstrating how a His-tagged protein (e.g., P38-$His_6$) can be isolated in the absence of a resin. The approach is based on modifying an albumin of choice (e.g., BSA) with a biotin derivative (e.g., Desthiobiotin-NHS) and a metal chelator (e.g., Ethylenediaminetetraacetic dianhydride), where the doubly-modified albumin, [Desthiobiotin-Albumin-EDTA] conjugate, serves as the purification tool (FIG. 53A, left). Thus, incubation of the doubly-modified albumin conjugate with a His-tagged protein and an appropriate metal ion generates a soluble [Doubly-modified albumin:metal ion:His-tagged protein] complex (FIG. 53A, right) which becomes insoluble and precipitate upon addition of free non-immobilized, avidin (FIG. 53B, right). Impurities, left in the supernatant, are removed by centrifugation (or filtration) and the pellet is further washed to remove traces of contaminations. The target His-tagged protein (or any other target possessing a His-tag) is then eluted from the precipitate by (for example) incubation with high concentration of imidazole which competes on binding to the metal, thereby, dissociating the His-tagged protein from the pellet. The purification scenario described (FIGS. 53A-B) is designated as Method A where binding of the His-tagged protein is performed under homogeneous conditions. An alternative scenario referred herein as Method B, include loading of the metal and formation of insoluble macro-complexes prior to binding to the His-tagged protein (FIG. 53 C, left). Such an approach will enable removal of free metal ions prior to the target binding, while binding is obtained under heterogeneous conditions FIG. 53C, right).

Materials and Methods

The General Synthesis of the [Desthiobiotin-Albumin-EDTA] Conjugates

In a medium containing 100 mM NaPi at pH 8, 10 mg/ml of an albumin of choice (e.g. BSA, HSA, ovalbumin) a mixture of: Ethylenediaminetetraacetic dianhydride (~1 mg/ml, Sigma 332046) and desthiobiotin-NHS (3 mg/ml, Berry & associates BT-1070 (both first dissolved in DMSO) was added to a final concentration of 1 mg/ml and 3 mg/ml respectively. Modification was carried out at room temperature for 4 hours with gentle agitation and no precipitate was observed. The medium was dialyzed against 25 mM NaPi at pH 7.2 to remove free derivatives of desthiobiotin and EDTA. Equivalent albumin conjugates (e.g. [Desthiobiotin-Albumin-DTPA], [Desthiobiotin-Albumin-NTA]) were obtained when a similar protocol was applied with other metal chelators such as: a. Diethylenetriaminepentaacetic acid dianhydride (Sigma, D6148), or NTA (e.g. Maleimide-$C_3$—NTA from Dojindo Kumamoto, Japan). It should be noted that the protocol may change according to the chemistry of the moieties involved.

General Purification Protocol Utilizing a Doubly-Modified BSA Conjugate Via Method A (FIG. 53A-B)

P38-$His_6$ was precipitated with a doubly-modified albumin (e.g. DB-BSA-EDTA1) in the presence of: 100 mM NaCl, 1.25 mM $M^{2+}$ (e.g. Ni2+, Co2+, Zn2+, Cu2+), E. coli cell lysate, 50-100 mM Tris at pH 8. The presence of a metal chelator (e.g. EDTA 1-50 mM or imidzole 1-25 mM may be present and this step as well and lead to greater purity). After a short incubation time (1-10 min.) at 4° C. or R.T, a freshly prepared avidin (or streptavidin) solution (0.5-5 mg/ml) was added slowly to the medium with/without vortexing and kept on ice for additional 0-60 minutes. A short spin generated a pellet and the supernatant excluded. Impurities left in the pellet were removed by resuspending it in a buffer (e.g. tris) containing metal chelators (e.g. 1-200 mM EDTA, 0.5-50 mM imidazole or both) at pH 7-9 and an additional centrifugation step was applied. P38-His$_6$ was eluted from the washed pellet by resuspending it in 50-100 mM Tris pH 8 and 0.02-1M of imidazole with/without EDTA at 4° C. or R.T. for 0.5-30 minutes with/without vortexing. A short spin (30 sec. at 14K) allowed removal of the supernatant.

Samples were loaded onto a 10% Bis-Tris SDS-poly-acrylamide gel according to Laemmli and developed for 1 hour at constant 120V. All gels were stained with Coomassie Brilliant Blue R250 and the intensity of bands was measured by densitometry using the Scion Image program. To achieve optimum purity and yield it is recommended to perform an additional short spin (20 sec, 14K) after each centrifugation step, so as to allow removal of traces (0.5-5%) of supernatant.

General Purification Protocol Utilizing a Doubly-Modified BSA Conjugate Via Method B (FIG. 53C):

The general protocol is similar to the one described above, though a macro-complex comprising a: [Doubly-modified albumin:Avidin (or streptavidin):metal] is first generated. The latter is then washed with buffer (e.g., tris) to remove free unbound metal and only then the target His-tagged protein is incubated with the washed macro-complex. All other steps (i.e., binding, washing and elution) are similar to those describe for method A.

Expression and Purification of P38-His$_6$ with a Ni2+-Chelating Sepharose Column Polymerase chain reactions (PCR) were used to introduce six Histidine residues in-frame to the N' of p38α (5' AATAACCATGGCGCATCATCATCATCAT-CATTCTCAGGAGAGGCCCACGT TCTACCG, SEQ ID NO: 25'-ATTGGATCCTCAGGACTCCATCTCTTCT-TGGTC: SEQ ID NO: 3).

The PCR products where digested with NcoI and BamHI and ligated to NcoI/BamHI digested pET-28a (Novagen). The vector plasmids containing the p38α genes were introduced into ROSSETA™ strain of *E. coli* (Novagen). An over-night 25 ml starter culture was inoculated into 1.5 l of fresh Luria-Broth (LB) medium containing ampicillin/chloramphenycol and grown at 37° C. to A600=0.4 and then transferred to 21° C. for 30 min. Protein expression was obtained by supplementing the media with 0.2 mM of Isopropyl-β-D-thiogalactopyranoside (IPTG) for 5 h. The cells were collected by centrifugation and stored at −20° C. For lysis the cell pellets were thawed on ice and suspended in buffer A containing: 0.5 M NaCl, 50 mM Tris-HCl buffer (pH 7.4), 10 mM Imidazole supplemented with proteases inhibitors cocktail (Sigma) and disrupted mechanically using micro-fluidizer (model M-110 EHIS; Microfluidics Corp. Newton, Mass.). The soluble and insoluble phases were separated by centrifugation (40,000 g for 50 min). The supernatant was loaded on a buffer A pre-equilibrated Ni2+-chelating Sepharose column (Amersham), extensively washed and eluted using a linear gradient of imidazole in buffer A. The protein-containing fractions were pooled, dialyzed against 100 mM NaCl, 25 mM Tris-HCl (pH 7.4), 1 mM EDTA and were further dialyzed against 100 mM NaCl, 25 mM Tris-HCl (pH 7.4), 10 mM MgCl$_2$, 1 mM DTT. Consequently, the protein was loaded on a source 15Q anion exchange column (Amersham) equilibrated with 100 mM NaCl, 50 mM Tris-HCl (pH 7.4), 5% (v/v) glycerol, 10 mM MgCl$_2$, 1 mM DTT and then eluted using a linear gradient of NaCl in the same buffer.

Results

The results presented in FIGS. 54A-B demonstrate the ability to purify a His-tagged protein with a doubly-modified BSA (i.e., [Desthiobiotin-Albumin-EDTA] conjugate) via methods A and B. In Method A, presented by gel A, FIG. 54A, lanes 2 and 3 show the difference in migration patterns between the native (lane 2) and the doubly-modified BSA (lane 3). Addition of the latter to a cell lysate containing P38-His$_6$ and either Ni2+ or Co2+ ions was speculated to generate a soluble [doubly-modified BSA:P38-His$_6$:Ni2+ or Co2+] soluble complex. The latter became insoluble and precipitated, upon addition of avidin (or streptavidin). After precipitation, the resulting pellet was washed to remove traces of impurities and the P38-His$_6$ was eluted in the presence of a high imidazole concentration (lanes 5-6). The observed bands at lanes 5 and 6 are likely the target P38-His$_6$ since: Of nore, an identical band was observed when P38-His$_6$ was purified with a commercial Ni2+ Sepharose column (lane 8). In addition, the molecular weight of the recombinant P38-His$_6$ is 43 kDa, which fits well with prestained markers used. Lane 9 demonstrates that the majority of impurities are removed during the precipitation step and that the doubly-modified BSA conjugate, is not preset in the excluded supernatant, as expected. Thus, according to Method A, binding occurs under homogenous solutions and only upon addition of avidin the system becomes heterogeneous.

FIG. 54B shows results derived from applying Method B. The recovered band seen in lane 4, is very similar to the band of the purified P38-His$_6$ obtained with the commercial Shepharose-Ni2+ column from Amersham (lane 1).

P38-His$_6$ samples isolated either via a Sepharose:Ni$^{2+}$ column or via the [Desthiobiotin-BSA-EDTA] conjugate (as described above) were analyzed by ESI, and the results are shown in FIG. 54C. The ESI analysis revealed a high sequence coverage of the two purified His-tagged proteins to the MK14_HUMAN Mitogen-activated protein kinase 14 (EC 2.7.11.24) which was the target protein. Matched peptides are shown in Bold red. Hence, the [Desthiobiotin-BSA-EDTA] approach, provides a viable alternative to the well established IMAC methodology.

Conclusions

The methods described herein can be applied for isolation of His-tagged proteins. Surprisingly, the possibility of washing the pellet with free EDTA (1-200 mM) while retaining the protein in the resusupended precipitate may enable removal of unwanted adsorbed molecules and may provide direct evidence to the unique high-affinity ternary complex generated between the conjugated EDTA, metal ion and the sequence of Histidines. Regeneration of the doubly-modified albumin conjugate was performed in the presence of biotin.

Of note:

a. Albumins other that BSA may be used (e.g., HSA, Ovalbumin), essentially any soluble entity capable of undergoing chemical modification may replace the [Desthiobiotin-Albumin-EDTA] conjugate.

b. Chelators other than EDTA may be used (e.g., DTPA, nitriloacetic acid (NTA), iminodiactetic acid (IDA), Phenanthroline, 8-hydroxyquinoline, carboxymethylated aspartic acid (CM-Asp), tris-carboxymethyl ethylene diamine (TED)).

c. Similar results were obtained when Zn2+ or Cu2+ were used, therefore other metals possessing binding affinity to the metal chelator used can be utilized as well (e.g., Cu+, Fe3+, Hg2+, Ag+).

d. Filtration can be used instead of centrifugation.

e. In order to reduce contamination, albumin (or any other non-modified protein) can be added to the reaction so as to compete with the doubly-modified albumin on binding to the metal. This is expected to increase purity. For example, if a doubly-modified BSA is used, one may add also native BSA to suppress non-specific binding of unwanted molecules.

f. Other pH values (e.g., pH 7) and/or buffers (e.g., NaPi) to the ones described above may be used accordingly.

Example 16

Detection, Quantization and Purification of Biotinylated Molecules

FIG. 55 shows an embodiment of the present invention wherein avidin is the ligand which is used to precipitate biotinylated protein targets. In this case the coordinating moiety is a metal chelator. This configuration can be used for specific precipitation and quantification.

Thus, "Detection Tool" comprises avidin or any of its analogs (e.g., streptavidin, Neutravidin, and their monomeric forms) that has been modified with a strong metal chelator (e.g., Catechol-NHS) (B). After the "Detection Tool" binds to the biotinylated-target (C), the soluble complex, is precipitated in the presence of different metal ions (e.g., $Fe^{3+}$) which interconnect catechol entities in the system, thereby generating insoluble macro-complexes containing the biotinylated-target (D). For quantization purposes, the biotinylated-target is quantified directly within the macro-complex (D) or after a dissolution step in the presence of a competing chelator is (E). For purification purposes, the biotinylated-target can be eluted under conditions which do not dissociate the catechol: $Fe^{3+}$ complex.

Example 17

Sample Preparation Such as for Proteomic Analysis

The following shows depletion of glycoproteins with a desthiobiotinylated-concanavalin A and free avidin Materials and Methods Depletion Protocol:

A synthesized desthiobiotinylated-concanavalin A was added Into a mixture containing *E. coli* cell lysate, porcine thyroglobulin and glucose oxidase and incubated at 0-4° C. for 10 minutes. The two glycoproteins (i.e. porcine thyroglobulin and glucose oxidase) were depleted by addition of a freshly prepared avidin solution. A short centrifugation step was applied (to remove the two precipitated glycoproteins) and the supernatant (devoid the above glycoproteins) was analyzed by SDS-PAGE.

Results

The results presented in FIG. 56 demonstrate that depletion glycoproteins can be achieved with a desthiobiotinylated-ligand (e.g. desthiobiotinylated-concanavalin A) and avidin, thus implying that other desthiobiotinylated ligands can be used accordingly. Moreover, a mixture of several different desthiobiotinylated-ligands can be used for simultaneous depletion of different target molecules. The above can be performed when a ligand/ligands are modified with catechol. Advantages of the above depletion approach:

a. Samples according to the presented approach are not diluted and a re-concentration step generally applied in multi-affinity columns may be circumvented.

b. The process is very fast (e.g. 12 minutes in the above example) therefore, aggregation, degradation or denaturation processes may be significantly suppressed. This may result in better representation of low abundance proteins in the 2D gel analysis.

Example 18

Comparison of T Cell Depletion Efficiency Between the Present Teachings and a Commercial Magnetic Bead Kit (Miltenyi CD3 Microbeads, Cat. 130-050-101)

Materials and Methods

Lymphocytes were separated from total blood using Ficol Paque Premium. PBS, anti-CD3 mAb and desthiobiotinylated-Protein A were added into the resuspended cells and incubated for 5 min. at room temperature with gentle rotation. A freshly prepared streptavidin solution was slowly added to the medium with constant vortexing (additional vortexing was generally further performed). The resultant mixture was then rotated with either a: Mixer-820 from SWELAB instruments, Sweden, or with a Nutating mixer (Gyromini) from LabNet Int. for additional few minutes. A Ficoll solution was gently added at the bottom of eppendorf and a short centrifugation step (e.g., 800 g, 7 min.) was applied. After centrifugation, the PBS phase and the upper part of the Ficoll phase were collected and biotin was added to dissociate all macro-complexes/aggregates in the system, generated by the [desthiobiotinylated-Protein A:Streptavidin] macro-complex. Excess of biotin and other reagents were removed by centrifugation (e.g., 1000 g, 2 min.); resuspended cells were stained with anti CD3-FITC (IQ products) and analyzed by FACS.

Results

The results presented in 57A-B and 58A-C, represent an average of 6-8 independent experiments demostrating the purity and yield obtained by either the magnetic bead technology kit (Miltenyi CD3 Microbeads, cat. 130-050-101), and that of the presented approach.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

REFERENCES

1) Mattiasson, B., Kumar, A., and Galaev, I. Yu. (1998) Affinity precipitation of proteins: design criteria for an efficient polymer. *J. Mol. Recognit.* 11, 211-216.

2) Freitag, R. (1998) Reversible water-soluble affinity macroligands for bioseparation. *Curr. Trends Polymer Sci.* 3, 63-79.

3) Freitag, R., and Horvath, C. (1996) Chromatography in the downstream processing of biotechnological products. *Adv. Biochem. Bioeng.* 53, 17-59.

4) Labrou, N., and Clonis, Y. D. (1994) The affinity technology in downstream processing. *J. Biotechnol.* 36, 95-119.

5) Lowe, C. R., Lowe, A. R., and Gupta, G. (2001) New developments in affinity chromatography with potential application in the production of biopharmaceuticals. *J. Biochem. Biophys. Methods.* 49, 561-574.

6) Cuatrecasas, P., Wilchek, M., and Anfinsen, C. B. (1968) Selective enzyme purification by affinity chromatography. *Proc. Natl. Acad. Sci. USA* 61, 636-643.

7) Cuatrecasas, P., and Wilchek, M. (1968) Single step purification of avidin from egg white by affinity chromatography by biocytin-Sepharose columns. *Biochem. Biophys. Res., Commun.* 33, 235-239.
8) Clonis, Y. D. (1991) Preparative dye-ligand chromatography. In: M. Hearn (Ed.), HPLC of Proteins Peptides and Polynucleotides, VCH, New York, pp. 453-468.
9) Dyr, J. E., and Suttnar, J. (1997) Separation used for purification of recombinant proteins. *J. Chromatogr.* B 699, 383-401.
10) Ohlson, S., Hansson, L., Larsson, P-O., and Mosbach, K. (1978) High performance liquid affinity chromatography (HPLAC) and its application to the separation of enzymes and antigens. *FEBS Lett.* 93, 5-9.
11) Mattiasson, B., and Olson, U, (1986) General chromatographic procedure based on the use of heterobifunctional affinity ligands. *J. Chromatogr.* 370, 21-28.
12) Afeyan, N., Gordonni, N., Mazsaroff, I., Varady, L., Fulton, S., Yang, Y. B., and Regnier, F. (1990) Flow through particles for the high performance liquid chromatographic separation of biomolecules: perfusion chromatography. *J. Chromatogr.* 519, 1-29.
13) Teichberg, V. I. (1990) Affinity repulsion chromatography. *J. Chromatogr.* 510, 49-57.
14) Slinerland, R., and Scouten, W. (1990) Centrifugal affinity chromatography. *J. Chromatogr.* 510, 205-211.
15) Nilsson, J., Ståhl, S., Lundeberg, J., Uhlén, M., and Nygren, P. Å. (1997) Affinity Fusion Strategies for Detection, Purification, and Immobilization of Recombinant Proteins. *Protein Expression Purif.* 11, 1-16.
16) Schneider, M., Guillot, C., and Lamy, B. (1981) The affinity precipitation technique. *Ann. NY Acad. Sci.* 369, 257-263.
17) Pearson, J., Clonis, Y. D., and Lowe, C. R. (1989) Preparative affinity precipitation of 1-lactate dehydrogenase. *J. Biotechnol.* 11, 267-274.
18) Gupta, M. N., and Mattiasson, B. (1994). Affinity precipitation in *Highly Selective Separations in Biotechnology*, ed. By G. Street, pp. 7-33. Chapman and Hall, London.
19) Hilbrig, F., and Freitag, R. (2003) Protein purification by affinity precipitation *J. Chromatogr. B* 790, 79-90.
20) Galaev, I. Yu., Gupta, M. N., and Mattiasson, B. (1996) Use smart polymers for Bioseparation *CHEMTEC* 19-26.
21) Galaev, I. Y. and Mattiasson, B. (1993) Affinity thermoprecipitation: the critical role of polymer in ligand-protein interactions. 6th European Congress on Biotechnology, Florence, 13-17 June, 1993, Italy, Vol. I. MO099.
22) Vaidya, A. A., Lele, B. S., Kulkarni, M. G., and Mashelkar, R. A. (1999) Enhancing ligand-protein binding affinity thermoprecipitation elucidation of spacer effects. *Biothechnol. Bioeng.* 64, 418-425.
23) Garret-Flaudy F. and Freitag, R. (2001) Use of the avidin (imino) biotinsystem as a general approach to affinity precipitation. *Biotechnol Bioeng.* 71, 223-234.
24) Graille, M., Stura, E. A., Corper, A. L., Sutton, B. J., Taussig, M. J., Charbonnier, J. B., Silverman, G. J., (2000) Crystal structure of a *Staphylococcus aureus* protein A domain complexed with the Fab fragment of a human IgM antibody: structural basis for recognition of B-cell receptors and superantigen activity. *Proc. Natl. Acad. Sci. USA* 97, 5399-404.
25) Sharon, N., and L is, H. (1972) Cell-Agglutinating and Sugar Specific Proteins. *Science* 177, 949-959.
26) Goldstein, I., Hollerman, C., and Smith E. (1965) Protein-Carbohydrate Interaction. II Inhibition Studies on the Interaction of Concanavalin A with Polysaccharides. *Biochemistry.* 4, 876-883.
27) Grimaldi, J., and Sykes, B. (1975) Concanavalin A: A Stopped Flow Nuclear Magnetic Resonance Study of Conformational Changes Induced by $Mn^{2+}$, $Ca^{2+}$, and alpha-Methyl-D-Mannoside. *J. Biol. Chem.* 250, 1618-1624.
28) Müller, W., Ringsdorf, H., Rump, E., Wildburg, G., Zhang, X., Angermaier, L., Knoll, W., Liley, M., and Spinke, J. (1993) Attempts to mimic docking processes of the immune system: recognition-induced formation of protein multilayers. *Science* 262, 1706-1708.
29) Hirsch, J. D., Eslamizar, L., Filanoski, B. J., Malekzadeh, N., Haugland, R. P., Beechem, J. M., and Haugland, R. P. (2002) Easily reversible desthiobiotinbinding to streptavidin, avidin, and other biotin-binding proteins: uses for protein labeling detection and isolation. *Anal. Biochem.* 308 (2), 343-357.
30) Kumar, A., and Gupta, M. N. (1994) Affinity precipitation of trypsin with soybean trypsin inhibitor linked Eudragit S-100. *J. Biotechnol.* 37, 185-189.
31) Bradford, M. M., (1976) A rapid sensitive method for the quantitation of micrograms quantities of protein utilizing the principle of protein-dye binding. *Anal. Biochem.* 72, 248-254.
32) Laemmli, U. K. (1970) Cleavage of structural proteins during the assembly of the head of bacteriophage T4. *Nature* 227, 680-685.
33) Bayer, E. D., Wilchek, M., and Skutelsky, E. (1976) Affinity cytochemistry: the localization of lectin and antibody receptors on erythrocytes via the avidin-biotin complex. *FEBS Lett.* 68, 240-244.
34) Patchornik, G., & Albeck, A., *Bioconjugate Chem.* 13, 111-119 (2005).
35) Nilsson, J. et al., *Protein Expr. Purif* 11, 1-16 (1997).
36) Bayer, E. D., Wilchek, M. & Skutelsky, E., *FEBS Lett.* 68, 240-244 (1976).
37) Martell, A. E., & Smith, R. M., in *Critical Stability Constants,* 3, 303-304, Plenum Press, New York (1974).
38) Martell, A. E. & Smith, R. M. in *Critical Stability Constants,* 3, 200-202, Plenum Press, New York (1974).

What is claimed is:

1. A method of purifying at least one His-tagged molecule, the method comprising:
   (a) contacting the His-tagged molecule with a composition comprising a non-immobilized doubly modified albumin molecule covalently attached to a biotin or biotin derivative, and further covalently attached to at least one chelator molecule capable of indirectly binding the His-tagged molecule via a metal ion, wherein said contacting is in the presence of said metal ion and avidin in solution so as to form a precipitate including said composition non-covalently bound to the His-tagged molecule;
   (b) collecting the precipitate; and
   (c) purifying at least one His-tagged molecule.

2. The method of claim 1, wherein said purifying is performed under homogeneous conditions.

3. The method of claim 1, wherein said purifying is performed under heterogeneous conditions.

4. The method of claim 1, wherein said biotin or biotin derivative is desthiobiotin.

5. The method of claim 1, wherein said chelator molecule is selected from the group consisting of EDTA, catechol and catechol derivatives, DTPA, nitriloacetic acid (NTA), iminodiacetic acid (IDA), Phenanthroline, 8-hydroxyquinoline, carboxymethylated aspartic acid (CM-Asp), and tris-carboxymethyl ethylene diamine (TED).

6. The method of claim 1, wherein said chelator molecule is EDTA, and said metal ion is selected from the group consisting of $Ni^{2+}$, $Co^{2+}$, $Cu^{2+}$, and $Zn^{2+}$.

7. The method of claim 1, wherein said chelator molecule is EDTA.

8. The method of claim 1, wherein said composition is desthiobiotin-albumin-EDTA.

* * * * *